(12) United States Patent
Huang

(10) Patent No.: US 8,124,637 B2
(45) Date of Patent: Feb. 28, 2012

(54) ANTHRA [1, 2-D]IMIDAZOLE-6,11-DIONE DERIVATIVES, PREPARATION METHOD AND APPLICATION THEREOF

(75) Inventor: Hsu-Shan Huang, Taipei (TW)

(73) Assignee: National Defense Medical Center, Taipei (TW)

( * ) Notice: Subject to any disclaimer, the term of this patent is extended or adjusted under 35 U.S.C. 154(b) by 53 days.

(21) Appl. No.: 12/712,680

(22) Filed: Feb. 25, 2010

(65) Prior Publication Data

US 2011/0207719 A1 Aug. 25, 2011

(51) Int. Cl.
- *A61K 31/122* (2006.01)
- *A61K 31/4184* (2006.01)
- *C07D 235/02* (2006.01)
- *C07C 50/18* (2006.01)

(52) U.S. Cl. ............ 514/393; 514/625; 548/300.4; 552/208

(58) Field of Classification Search .............. None
See application file for complete search history.

(56) References Cited

FOREIGN PATENT DOCUMENTS

TW 401405 B * 8/2000

OTHER PUBLICATIONS

Chang, et al. J. Het. Chem. 33:367 (1996).*

* cited by examiner

*Primary Examiner* — Yong Chu
*Assistant Examiner* — Michael Barker
(74) *Attorney, Agent, or Firm* — Muncy, Geissler, Olds & Lowe, PLLC

(57) ABSTRACT

A series of novel anthra[1,2-d]imidazole-6,11-dione derivatives, and the preparation method and application of said derivatives, wherein said application includes a pharmaceutical composition containing said derivatives for treating cancer, and said application involves effects of said derivatives for inhibiting telomerase activity, inhibiting the growth of cancer cell, treating cancer and the like.

9 Claims, 11 Drawing Sheets ific therapy, as most tumor cells have high expression of telomerase, whereas most normal somatic cells express low or undetectable levels of telomerase and are therefore an attractive target for the design of anticancer agents.
ANTHRA [1, 2-D]IMIDAZOLE-6,11-DIONE DERIVATIVES, PREPARATION METHOD AND APPLICATION THEREOF

BACKGROUND OF THE INVENTION

1. Field of the Invention

The present invention relates to development of cancer drug, in particular, the development of novel anthra[1,2-d]imidazole-6,11-dione derivatives, preparation method and application thereof.

2. Description of the Prior Art

Telomere

A telomere is a region of repetitive DNA at the end of a chromosome, which protects the end of the chromosome from deterioration, recombination, and end-to-end fusion. A telomere is composed of short and repeated DNA sequences. A high percentage of guanine (G) is present in this DNA sequence from the 5'-end to the 3'-end. The telomere DNA sequence (TTAGGG)n is conserved among vertebrates, including humans.

In a normal somatic cell, the terminal end of the chromosome will lose a part of the RNA primer after each replication, and will shorten off about 50-60 bp after each cell division. When the telomere is shortened to a certain extent, the cell will go to apoptosis. This phenomenon is called an end-replication problem of a cell.

Telomerase

Telomerase is the enzyme that synthesizes telomeric DNA, the terminal DNA at chromosome ends which, together with telomere-binding proteins, confers stability to chromosomes. In most organisms, replication and maintenance of the length of telomere has to rely on telomerase. The telomerase is composed of RNA and protein subunits. At present, part of the important telomerase subunits have been identified. The composition of human telomerase comprises human telomerase reverse transcriptase (hTERT) having reverse transciptase activity, human telomerase RNA component used as a template, and some telomere-binding proteins such as human telomerase-associated protein, p23, hsp90, hsp40, hsp70 and the like.

Many research studies have indicated that the activity of human telomerase can only be detected in cells having a high proliferation ability, for example, germ cells, hemopoietic cells, part of stem cells, most of immortalized cells and most of tumor cells. In the somatic cell, the telomere will be shortened gradually as the number of cell divisions increase, which may be considered as the mitotic clock for counting the number of cell divisions. When a telomere is shortened to a certain extent, the cell will stop division and entering an aging stage, stay at this stage for a period of time, and then go to death. This period of time is called mortality stage 1 (M1 stage). When a tumor suppressor gene such as p53 or Rb is mutated within the M1 stage, the cell might escape from the aging stage and continue cell division in a period of time which is called mortality stage 2 (M2 stage). If a cell lacks telomerase activity during this period, the length of a telomere will be reduced further, and the telomere will not be able to protect the terminal end of the chromosome. This might result into the instability of the chromosome, as well as the cell cannot transfer genetic information completely and enters apoptosis in the end. Therefore, the M2 stage is also called a crisis stage. Most of cells will die in the M2 stage, except a small part of cells with telomerase activity will survive. This small part of cells will continue to divide without limitation and become an immortalized cell (or a cancer cell).

In view of the foregoing, it is thought generally that the activation of telomerase can maintain the length of a telomere so as to prevent a cell from entering the aging stage; or the inhibition of telomerase activity can be used to limit the division of a cancer cell. Both thoughts may become key factors in the development of a cell toward immortalization or cancerization. In summary, using telomerase inhibitors to treat cancer have been considered as a novel cancer-specific therapy, as most tumor cells have high expression of telomerase, whereas most normal somatic cells express low or undetectable levels of telomerase and are therefore an attractive target for the design of anticancer agents.

Anthraquinone-containing extracts from different plant sources such as senna, cascara, aloe, frangula, and rhubarb have been found to have wide variety of pharmacological activities such as anti-inflammatory, wound healing, analgesic, antipyretic, antimicrobial, and antitumor activities. Some of the anthraquinone derivatives have also shown antitumor activity. Therefore, many investigators consider them as highly promising lead candidates in drug design.

In view of the importance of the development of cancer therapy drugs, the invention provides inventive anthra[1,2-d]imidazole-6,11-dione derivatives, preparation method and application thereof.

SUMMARY OF THE INVENTION

One object of the invention is to provide a series of novel anthra[1,2-d]imidazole-6,11-dione derivatives, said anthra[1,2-d]imidazole-6,11-dione derivatives represented by formula I and formula II, wherein $R_1$ and $R_2$ are as defined herein.

Another object of the invention is to provide a method for preparing novel anthra[1,2-d]imidazole-6,11-dione derivatives represented by formula I and formula II, wherein $R_1$ and $R_2$ are as defined herein.

In addition, another object of the invention is to provide a pharmaceutical composition containing said novel anthra[1,2-d]imidazole-6,11-dione derivatives as represented by formula I and formula II (wherein $R_1$ and $R_2$ are as defined herein), said pharmaceutical composition being used to treat cancer.

In order to achieve the above-described objects of the invention, the inventor used commercial 1,2-diaminoanthraquinone as the reaction starting materials to carry out modification on various functional groups through chemical synthetic reaction, so as to produce a series of novel anthra[1,2-d]imidazole-6,11-dione derivatives, namely, compounds CL01 to CL40.

In addition, the invention investigates and evaluates in the following examples whether the derivatives of the invention serve as a target drug or a chemotherapy drug, so as to provide an inhibition effect on the growth of tumor cell or cancer cell, and further treat cancer.

These features and advantages of the present invention will be fully understood and appreciated from the following detailed description of the accompanying drawings.

DETAILED DESCRIPTION OF THE PREFERRED EMBODIMENT

The invention provides a series of novel anthra[1,2-d]imidazole-6,11-dione derivatives, preparation method and application thereof, wherein said application includes said derivatives with therapeutically effective amount are prepared into pharmaceutical compositions for treating cancer, wherein said pharmaceutical composition comprises at least one compound selected from the group consisting of therapeutically effective amount of compounds represented by general formula I and II, and a pharmaceutically acceptable excipient, wherein $R_1$ and $R_2$ are defined herein:

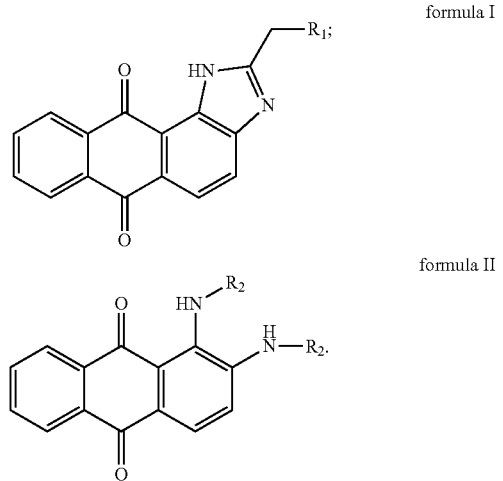

formula I formula II

Said pharmaceutical composition with therapeutically effective amount is used to treat cancer and inhibit the growth of cancer cell, wherein said cancer includes, but is not limited to, leukemia, non-small cell lung cancer and the like.

The excipient that can be used in the invention comprises, but is not limited to, diluent, filler, binder, disintegrating agent, lubricant and the like. Further, said excipient includes, but is not limited to microcrystalline cellulose, polyvinylpyrrolidone (PVP), corn starch, modified starches, sodium carboxymethylstarch, resin, gelatinized starches, sugars, polyethylene glycol (PEG), polyvinyl alcohol, hydroxypropyl cellulose, methyl cellulose, hydroxymethyl cellulose, hydroxypropyl methyl cellulose and the like.

The term "therapeutically effective amount" or "pharmaceutically effective dosage" refers to the amount of a compound or a combination of compounds used to treat disease (such as cancer), to improve, attenuate or eliminate one or more symptoms of a particular disease (such as cancer), or to inhibit or delay the outbreak of one or more symptoms caused by growth or proliferation of cancer cells.

The term "pharmaceutically acceptable" is intended to mean that a substance or a combination has to be compatible with other components in the same formulation, and also has to be not harmful or cause no other side effect to a patient. The term "relative cell survival rate" is intended to mean that comparing to drug-untreated group or the placebo group (control), the relative cell survival rate of the drug-treated group (or test group) at least having 40% to 50%.

The invention will be illustrated with the examples as follows, without the intention that the invention is limited thereto. The substance or material herein are easily obtained, the source of material is not limited to following examples.

EXAMPLE 1

Chemical Synthesis

Figure 1:
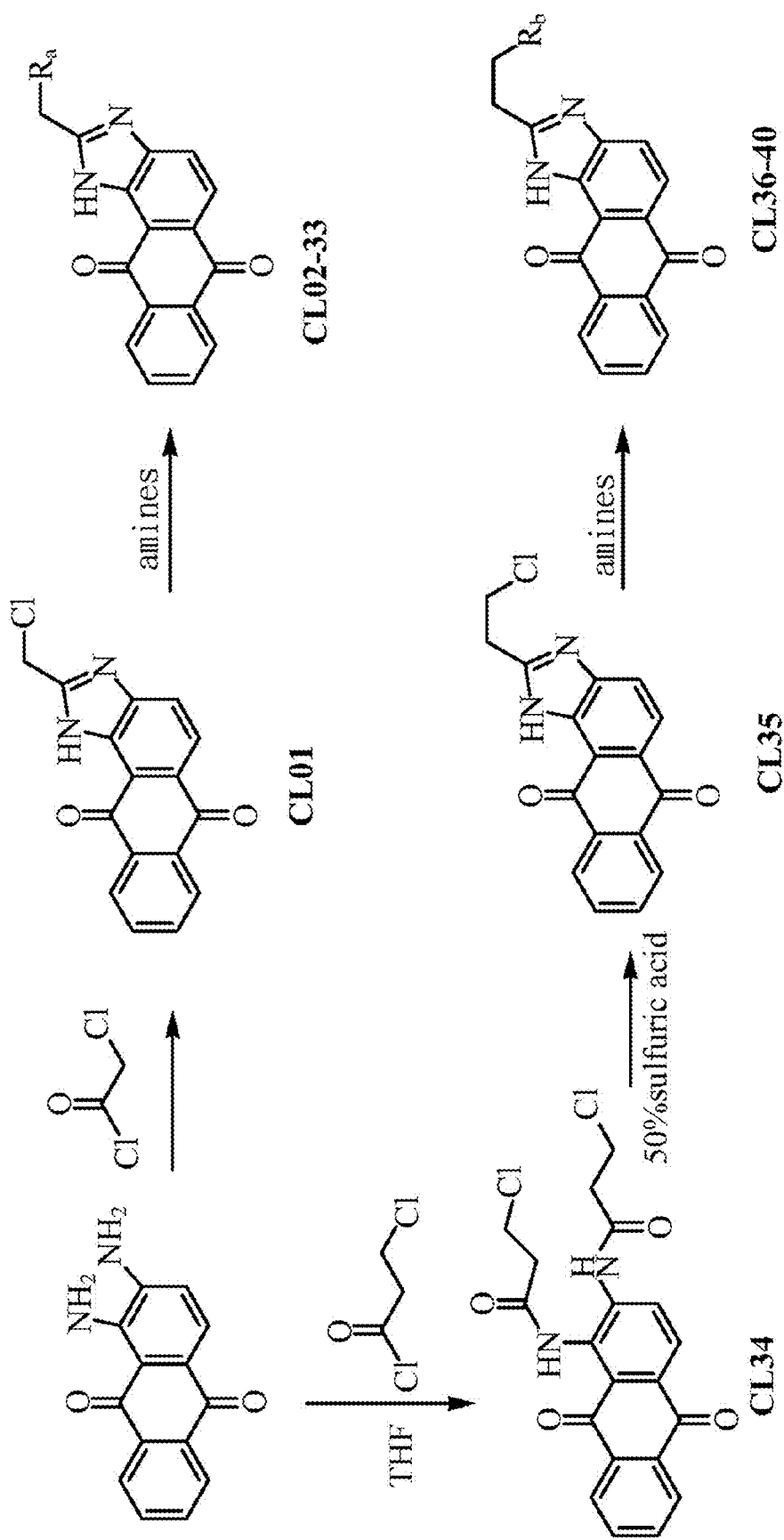
FIG. 1 depicts the preparation process of compound CL01 to CL40.

Referring to FIG. 1:

1. General Procedure A: Preparation of Compound CL01

Compound 1,2-diaminoanthraquinone was dissolved in N—N-dimethylformamide (DMF), and thereto was added with chloroacetyl chloride under stirring. After completion of reaction, the mixed solution was cooled down, filtered to collect precipitate, and finally, the precipitate was washed with ethanol to obtain a compound CL01.

2. General Procedure B: Preparation of Compound CL02 to CL33

Compound CL01 and N,N-Diisopropylethylamine (DIPEA) or triethylamine (TEA) were stirred in tetrahydrofuran (THF). Then, a series of amines was added dropwise into the THF mixture under stirring. The mixed solution was heated under reflux. After completion of reaction, the mixed solution was concentrated under reduced pressure, extracted with ethyl acetate, dried by $MgSO_4$, and recrystallized in n-hexane and ethyl acetate (EA). The product was collected by filtering and washed with acetone to obtain compounds CL02 to CL33.

3. General Procedure C: Preparation of Compound CL34

Compound 1,2-diaminoanthraquinone was dissolved in N,N-dimethylformamide, and thereto was added successively with triethylamine (TEA) and 3-chloropropionyl chloride under stirring. After completion of reaction, the mixed solution was cooled down, filtered to collect the precipitate, and finally, the precipitate was washed with ethanol to obtain a compound CL34.

4. General Procedure D: Preparation of Compound CL35

Compound CL34 was dissolved in 50% sulfuric acid at 0° C., and the solution was reacted in an oil bath at a temperature of about 110° C. under stirring. After completion of reaction, the mixed solution was extrated with dichloromethane, dried by $MgSO_4$, concentrated under reduced pressure and filtered. The precipitate thus obtained was washed with acetone, and evaporated to dryness in vacuum to obtain a compound CL35.

5. General Procedure E: Preparation of Compound CL36 to CL40

Compound CL35, DIPEA and a series of amine was stirred in tetrahydrofuran (THF). The mixed solution was heated under reflux. After completion of reaction, the mixed solution was concentrated under reduced pressure, extracted with ethyl acetate. The extract was dried by $MgSO_4$ and concentrated under reduced pressure to obtain a crude product. The crude product was recrystallized in ethyl hexane and EA. The mixture was filtered to collect the crystal which was washed with acetone to obtain compounds CL36 to CL40.

EXAMPLE 2

Telomerase Activity Assays

Compounds CL-01 to CL-40 (total 40 compounds) chemically synthesized above were subjected to following four sections of telomerase activity assays: 2-1. Telomere repeat amplification protocol (TRAP) assays; 2-2. Secreted alkaline phosphatase assay (SEAP assay); 2-3. MTT assay and 2-4. The United State National Cancer Institute (NCI) had selected 6 compounds from the invention, which were subjected to cell toxicity assay against 60 kinds of cancer cell lines.

2-1. Telomere Repeat Amplification Protocol (TRAP) Assay:

Telomerase activity was detected by a modified version of the general TRAP protocol. Telomerase products were resolved by 10% polyacrylamide gel electrophoresis and visualized by staining with SYBER Green. As a source of telomerase, the total cell lysates derived from lung cancer cell line H1299 cells were used. Protein concentration of the lysates was assayed using Bio-Rad protein assay kit using BSA standards.

2-2. SEAP Assay

Cell Culture and Assessment of hTERT:

H1299 is a non-small-cell lung cancer cell strain and possesses telomerase activity, therefore, is suitable to be used as a model cell strain for screen telomerase inhibitor. H1299 were grown in RPMI 1640 media supplemented with 10% fetal bovine serum, 100 units/mL penicillin and 100 mg/mL streptomycin in a humidified atmosphere with 5% $CO_2$ at 37° C. Culture media were changed every three days. To establish stable cell lines that the expression of hTERT could be monitored by a reporter system, a about 3.3 kbp DNA fragment ranging from −3338 to +1 bp of the hTERT gene (hTERT promoter, $P_{hTERT}$) was subcloned upstream to a secreted alkaline phosphatase gene (SEAP) and transfected into H1299 bp electroporation. The stable clones were selected using G418. The stable clones derived from H1299 were cultured using conditions that are similar to their parental cells.

SEAP Assay:

Secreted alkaline phosphatase was used as the reporter system to monitor the transcriptional activity of hTERT. Here, about $10^4$ cells each were grown in 96-well plates and incubated at 37° C. for 24 hours and changed with fresh media. Varying amounts of drugs were added and cells were incubated for another 24 hours. Culture media were collected and heated at 65° C. for 10 min to inactivate heat-labile phosphatases. An equal amount of SEAP buffer (2 M diethanolamine, 1 mM $MgCl_2$, and 20 mM $_L$-homoarginine) was added to the media and p-nitrophenyl phosphate was added to a final concentration of 12 mM. Absorptions at 405 nm were taken, and the rate of absorption increase is determined (the increasing rate of absorbance at 405 nm was used to represent the activity of SEAP).

Further, cells were subjected to MTT assay to compare the relative toxicity or effect of each compound on cell proliferation and activity.

2-3. MTT Assay

MTT assay is a method often used to determine cell survival rate or proliferation, which is described briefly as follows:

The above-described cells are cultured in a 96-well plate, to which was added with 25 μl MTT solution, and cultured in a 37° C. carbon dioxide incubator for 4 hours. Then, 100 μl Lysis buffer is added and incubated in a 37° C. carbon dioxide incubator overnight. An ELISA reader (Bio-Rad Model 450) is used to read optical density (O.D.) at 550 nm.

2-4. The National Cancer Institute (NCI)'s Anticancer Drug Screen

In brief, cellular protein levels were determined after 48 hours of drug exposure by sulforhodamine B colorimetry. Through the use of a time 0 cell control, the cell growth can be determined for each cell line thus allowing calculations of the 50% growth inhibitory concentration ($GI_{50}$), the total growth inhibition (TGI), and the 50% lethal concentration ($LC_{50}$). Comparison to plates not exposed to drug permits determination of concentration and times of exposure conferring 50% net growth inhibition ($GI_{50}$), TGI, and 50% cell kill ($LC_{50}$). These data are then plotted as mean bar graphs and as dose-response curves.

Figure 2:
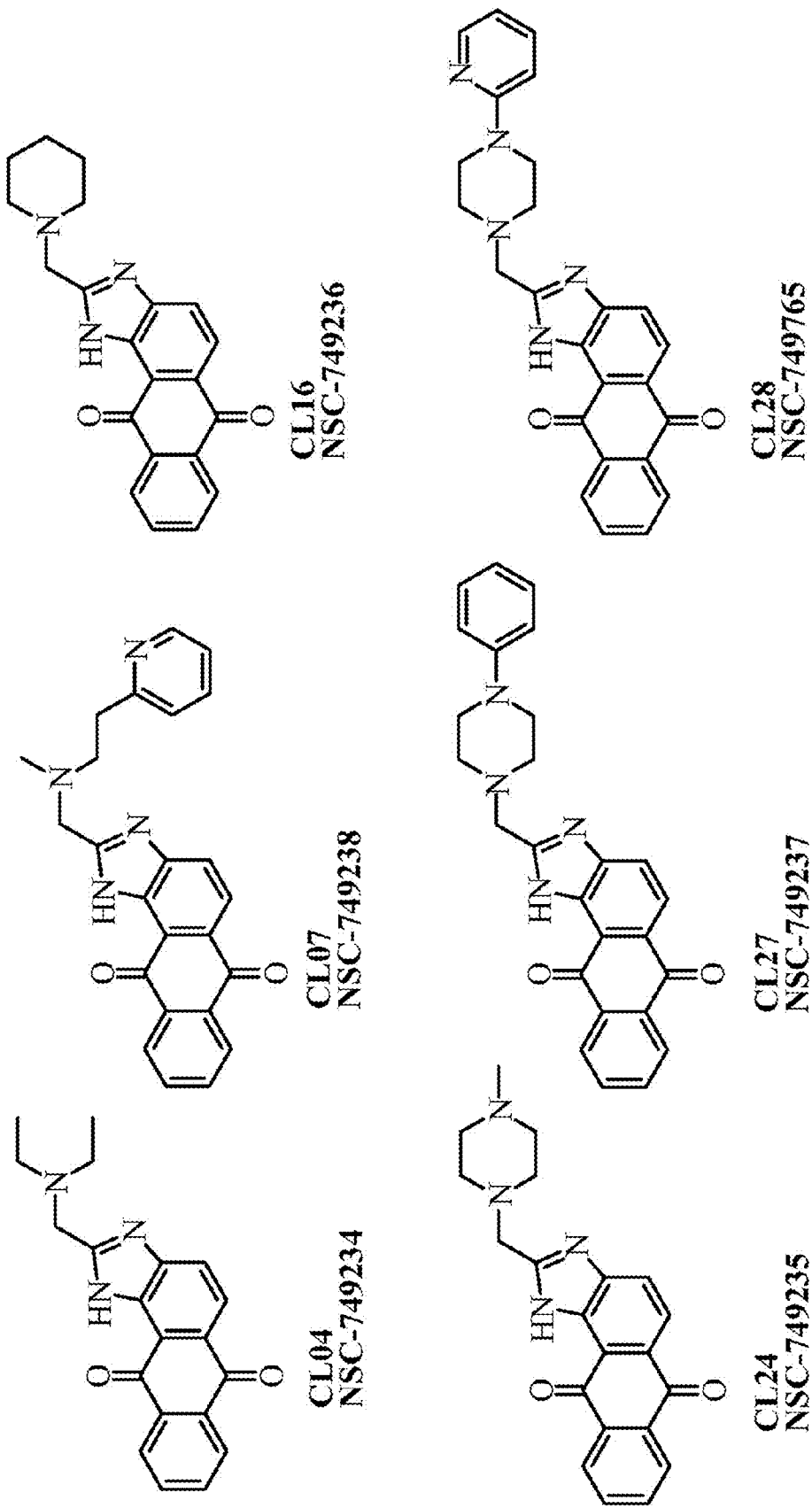
FIG. 2 depicts the compounds selected by National Cancer Institute (NCI) for NCI Developmental Therapeutics Program (DTP) in-vitro screen of 60 human derived cancer cell lines.

From the data analysis it follows that approximately 95% of the actives (potent anticancer drugs) from the 60 cell line screen can be identified. By these criteria, 6 compounds (each with its certification number, refer to FIG. 2) of the invention were reported that having anticancer activity.

Synthesis and Analysis of Each Compound:

The chemical synthetic procedure of anthra[1,2-d]imidazole-6,11-dione derivatives described in Example 1 was disclosed further in following examples.

Testing Instruments:

Melting point determination was carried out on a Büch±545 melting point tester. High resolution mass-spectroscopy comprises FINNIGAN MAT-95XL in National Tsing Hua University Instrument Center, FININGAN MAT 95S MS in National Taiwan University Instrument Center. $^1$H-NMR and $^{13}$C-NMR were recoded on Varian GEMINI-300 (300 MHz).

EXAMPLE 3

2-(chloromethyl)-1H-anthra[1,2-d]imidazole-6,11-dione (CL01)

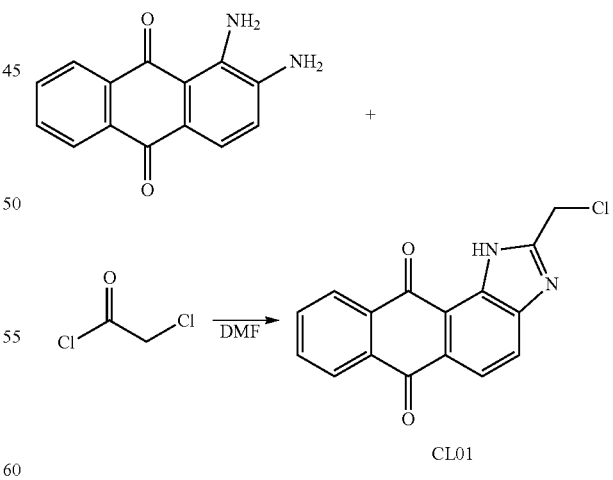

CL01

Compound 1,2-diaminoanthraquinone (1.19 g, 5 mmole) was dissolved in 20 mL N,N-dimethylformamide. Chloroacetyl chloride (0.5 mL, 6 mmole) was added and the resulted solution was reacted by heating at 80° C. under stirring for 10 hours. After completion of reaction, the mixed solution was poured into ice-water (200 mL). Then, the mixture was filtered to collect the precipitate. Finally, the precipitate was rinsed with hot ethanol to obtain a yellowish brown compound.

Mol. Wt.: 296.7079 ($C_{16}H_9N_2O_2Cl$); Yield: 65%; Mp: 209-210° C.; $R_f$: 0.62 (ethyl acetate:dichloromethane=1:1); HRMS (EI) m/z calcd for $C_{16}H_9N_2O_2Cl^+[M]^+$: 296.0353. Found: 296.0344. $^1$H-NMR (300 MHz, $CDCl_3$) δ (ppm): 4.93 (s, 2H, —CH2Cl), 7.81-7.83 (m, 2H, Ar—$H_{8,9}$), 8.09 (1H, d, J=8.7 Hz, Ar—H5), 8.24 (1H, d, J=9 Hz, Ar—H4), 8.29-8.35 (2H, m, Ar—H7,10); $^{13}$C-NMR (75 MHz, $CDCl_3$) δ (ppm): 37.81, 118.61, 122.02, 126.28, 126.69, 127.74, 129.43, 132.75, 133.28, 134.01, 134.62, 138.34, 154.56, 182.81, 185.02.

EXAMPLE 4

2-((dimethylamino)methyl)-1H-anthra[1,2-d]imidazole-6,11-dione (CL02)

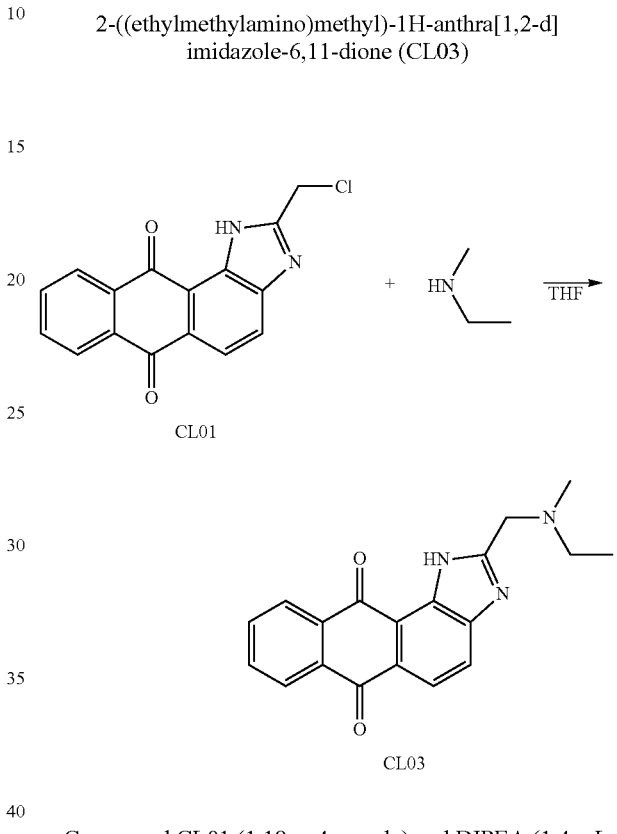

Compound CL01 (1.18 g, 4 mmole) and DIPEA (1.4 mL, 8 mmole) were stirred in 30 mL anhydrous tetrahydrofuran (THF) for 10 minutes. Then, dimethylamine (0.8 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 305.3306 ($C_{18}H_{15}N_3O_2$); Yield: 40%; Mp: 171-172° C.; $R_f$: 0.50 (ethyl acetate:dichloromethane:methanol=2:2:1); HRMS (ESI) m/z calcd for $C_{18}H_{15}N_3O_2^+[M]^+$: 305.1164. Found: $[M+H]^+$=306.1264, $[M+Na]^+$=328.1803. $^1$H-NMR (300 MHz, $CDCl_3$) δ (ppm): 2.53 (s, 6H, —N—$CH_3$), 4.02 (s, 2H, —$CH_2$—), 7.76-7.80 (m, 2H, Ar—$H_{8,9}$), 7.95 (d, J=8.4 Hz, 1H, Ar—$H_4$), 8.13 (d, J=8.4 Hz, 1H, Ar—$H_5$), 8.18-8.32 (m, 2H, Ar—$H_{7,10}$); $^{13}$C-NMR (75 MHz, $CDCl_3$) δ (ppm): 44.94, 56.69, 117.86, 120.92, 124.98, 126.01, 126.98, 128.25, 131.93, 132.80, 133.23, 133.41, 133.74, 148.21, 156.80, 182.34, 184.08.

EXAMPLE 5

2-((ethylmethylamino)methyl)-1H-anthra[1,2-d]imidazole-6,11-dione (CL03)

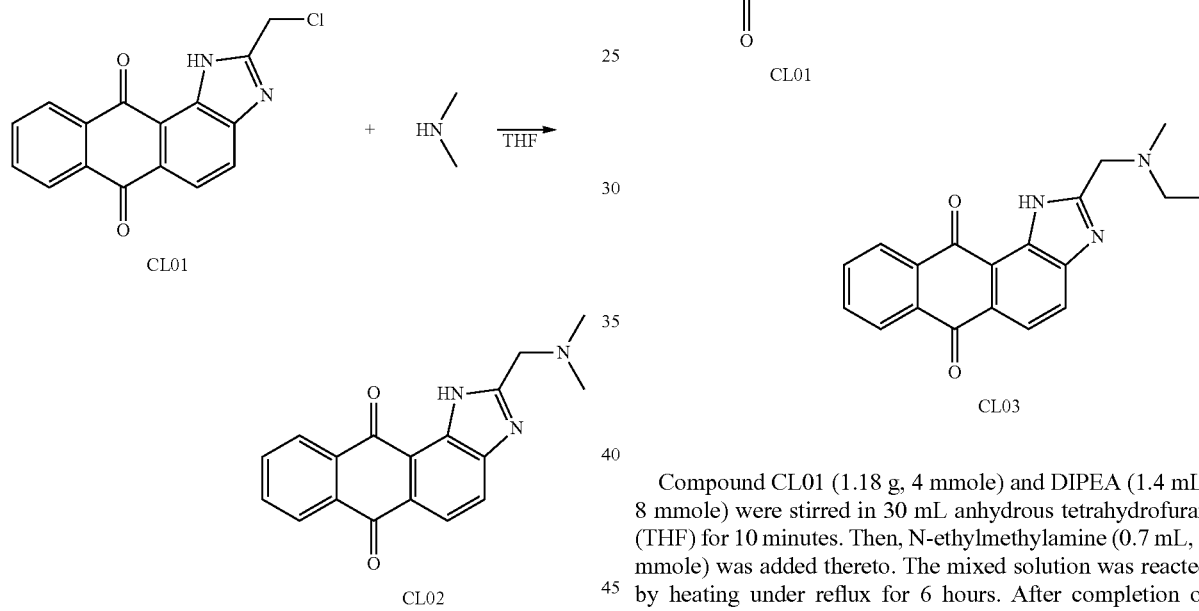

Compound CL01 (1.18 g, 4 mmole) and DIPEA (1.4 mL, 8 mmole) were stirred in 30 mL anhydrous tetrahydrofuran (THF) for 10 minutes. Then, N-ethylmethylamine (0.7 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 319.3572 ($C_{19}H_{12}N_3O_2$); Yield: 51%; Mp: 160-161° C.; $R_f$: 0.62 (ethyl acetate: dichloromethane: methanol=2:2:1); HRMS (ESI) m/z calcd for $C_{19}H_{17}N_3O_2^+[M]^+$: 319.1321. Found: $[M+H]^+$=320.1423, $[M+Na]^+$=342.1245. $^1$H-NMR (300 MHz, $CDCl_3$) δ (ppm): 1.21 (t, J=7.2 Hz, 3H, —$CH_3$), 2.43 (s, 3H, —N—$CH_3$), 2.69 (q, J=7.2 Hz, 2H, —$CH_2$—), 4.00 (s, 2H, —$CH_2$—), 7.76-7.79 (m, 2H, Ar—$H_{8,9}$), 7.98 (d, J=8.4 Hz, 1H, Ar—$H_4$), 8.15 (d, J=8.4 Hz, 1H, Ar—$H_5$), 8.21-8.31 (m, 2H, Ar—$H_{7,10}$); $^{13}$C-NMR (75 MHz, $CDCl_3$) δ (ppm): 11.38, 30.09, 41.45, 51.32, 54.74, 117.80, 120.90, 124.88, 126.00, 128.12, 131.90, 132.89, 132.45, 133.20, 133.48, 133.70, 148.45, 182.37, 184.25.

EXAMPLE 6

2-((diethylamino)methyl)-1H-anthra[1,2-d]imidazole-6,11-dione (CL04)

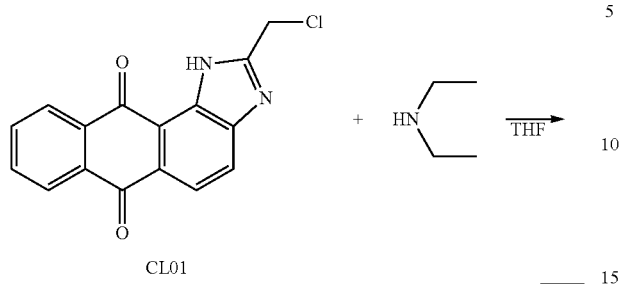

Compound CL01 (1.18 g, 4 mmole) and DIPEA (1.4 mL, 8 mmole) were stirred in 30 mL anhydrous tetrahydrofuran (THF) for 10 minutes. Then, diethylamine (0.7 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 333.3838 ($C_{20}H_{19}N_3O_2$); Yield: 45%; Mp: 159-160° C.; $R_f$: 0.71 (ethyl acetate:dichloromethane:methanol=2:2:1); HRMS (ESI) m/z calcd for $C_{20}H_{19}N_3O_2^+[M]^+$: 333.1477. Found: $[M+H]^+=334.1580$, $[M+Na]^+=356.1407$. $^1$H-NMR (300 MHz, $CDCl_3$) δ (ppm): 1.15 (t, J=7.2 Hz, 6H, —$CH_3$), 2.74 (q, J=7.1 Hz, 4H, —$CH_2$—), 4.03 (s, 2H, —$CH_2$—), 7.76-7.79 (m, 2H, Ar—$H_{8,9}$), 7.99 (d, J=8.4 Hz, 1H, Ar—$H_4$), 8.17 (d, J=8.4 Hz, 1H, Ar—$H_5$), 8.23-8.32 (m, 2H, Ar—$H_{7,10}$); $^{13}$C-NMR (75 MHz, $CDCl_3$) δ (ppm): 11.73, 48.17, 51.95, 118.34, 121.49, 125.35, 126.59, 127.56, 128.61, 132.35, 133.50, 133.79, 134.09, 134.29, 149.30, 183.00, 184.90.

EXAMPLE 7

2-((methylpropylamino)methyl)-1H-anthra[1,2-d]imidazole-6,11-dione (CL05)

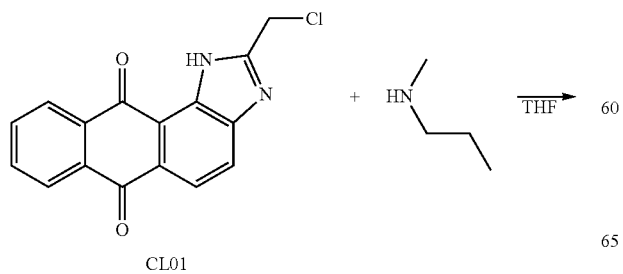

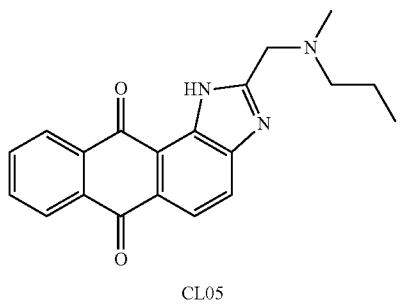

Compound CL01 (1.18 g, 4 mmole) and DIPEA (1.4 mL, 8 mmole) were stirred in 30 mL anhydrous tetrahydrofuran (THF) for 10 minutes. Then, N-methylpropylamine (0.8 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 333.3838 ($C_{20}H_{19}N_3O_2$); Yield: 43%; Mp: 141-142° C.; $R_f$: 0.74 (ethyl acetate: dichloromethane: methanol=2:2:1); HRMS (ESI) m/z calcd for $C_{20}H_{19}N_3O_2^+[M]^+$: 333.1477. Found: $[M+H]^+=334.1579$, $[M+Na]^+=356.1405$. $^1$H-NMR (300 MHz, $CDCl_3$) δ (ppm): 0.97 (t, J=7.4 Hz, 3H, —$CH_3$), 1.59-1.61 (m, 2H, —$CH_2$—), 2.42 (s, 3H, —N—$CH_3$), 2.55 (t, J=7.5 Hz, 2H, —$CH_2$—), 3.98 (s, 2H, —$CH_2$—), 7.76-7.79 (m, 2H, Ar—$H_{8,9}$), 7.99 (d, J=8.4 Hz, 1H, Ar—$H_4$), 8.16 (d, J=8.4 Hz, 1H, Ar—$H_5$), 8.24-8.31 (m, 2H, Ar—$H_{7,10}$); $^{13}$C-NMR (75 MHz, $CDCl_3$) δ (ppm): 11.54, 20.22, 42.64, 55.90, 59.87, 118.34, 121.49, 125.44, 126.60, 127.56, 128.67, 132.45, 133.46, 133.80, 134.04, 134.30, 149.06, 158.76, 182.98, 184.84.

EXAMPLE 8

2-((ethylisopropylamino)methyl)-1H-anthra[1,2-d]imidazole-6,11-dione (CL06)

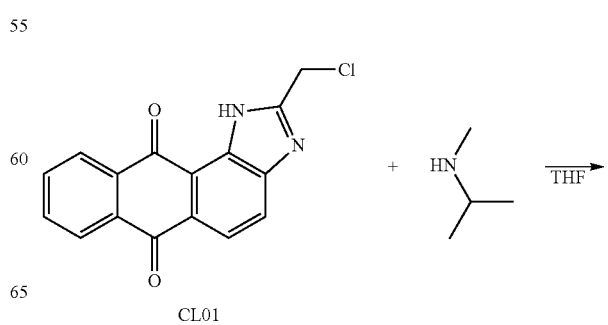

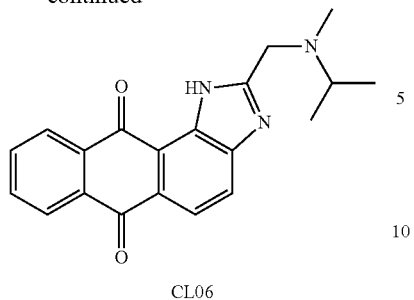

CL06

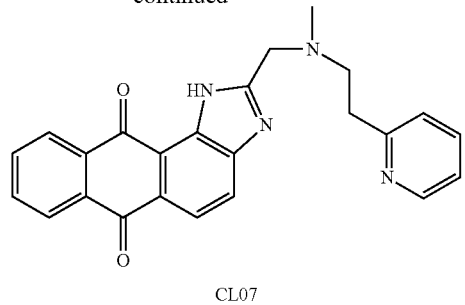

CL07

Compound CL01 (1.18 g, 4 mmole) and DIPEA (1.4 mL, 8 mmole) were stirred in 30 mL anhydrous tetrahydrofuran (THF) for 10 minutes. Then, N-ethylisopropylamino (0.8 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 333.3838 ($C_{20}H_{19}N_3O_2$); Yield: 47%; Mp: 165-166° C.; $R_f$: 0.69 (ethyl acetate:dichloromethane:methanol=2:2:1); HRMS (ESI) m/z calcd for $C_{20}H_{19}N_3O_2{}^+[M]^+$: 333.1477. Found: $[M+H]^+$=334.1578, $[M+Na]^+$=356.1402. $^1$H-NMR (300 MHz, $CDCl_3$) δ (ppm): 1.15 (d, J=6.4 Hz, 6H, —$CH_3$), 2.33 (s, 3H, —N—$CH_3$), 2.96-3.04 (m, 1H, —CH—), 3.96 (s, 2H, —$CH_2$—), 7.76-7.81 (m, 2H, Ar—$H_{8,9}$), 7.99 (d, J=8.4 Hz, 1H, Ar—$H_4$), 8.16 (d, J=8.4 Hz, 1H, Ar—$H_5$), 8.22-8.31 (m, 2H, Ar—$H_{7,10}$); $^{13}$C-NMR (75 MHz, $CDCl_3$) δ (ppm): 17.78, 37.29, 51.88, 54.42, 118.49, 121.54, 125.43, 126.66, 127.58, 128.78, 132.52, 133.55, 133.83, 134.12, 134.30, 149.18, 183.03, 184.84.

EXAMPLE 9

2-((N-methyl-2-(pyridin-2-yl)ethanamino)methyl)-1H-anthra[1,2-d]imidazole-6,11-dione (CL07)

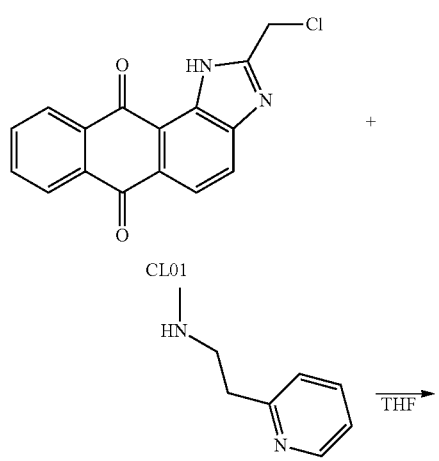

Compound CL01 (1.18 g, 4 mmole) and DIPEA (1.4 mL, 8 mmole) were stirred in 30 mL anhydrous tetrahydrofuran (THF) for 10 minutes. Then, 2-(2-methylaminoethyl)pyridine (1.1 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 396.4412 ($C_{24}H_{20}N_4O_2$); Yield: 48%; Mp: 150-151° C.; $R_f$: 0.56 (ethyl acetate:dichloromethane:methanol=2:2:1); HRMS (EI) m/z calcd for $C_{24}H_{20}N_4O_2{}^+[M]^+$: 396.1586. Found: 396.1584. $^1$H-NMR (300 MHz, $CDCl_3$) δ (ppm): 2.44 (s, 3H, —N—$CH_3$), 3.01-3.11 (m, 4H, —$CH_2$—), 4.00 (s, 2H, —$CH_2$—), 7.13-7.17 (m, 1H, Ar'—$H_5$), 7.21 (d, J=7.5 Hz, 1H, Ar'—$H_3$), 7.61-7.67 (m, 1H, Ar'—$H_4$), 7.76-7.80 (m, 2H, Ar—$H_{8,9}$), 7.99 (d, J=8.4 Hz, 1H, Ar—$H_4$), 8.16 (d, J=8.7 Hz, 1H, Ar—$H_5$), 8.25-8.32 (m, 2H, Ar—$H_{7,10}$), 8.63-8.65 (m, 1H, Ar'—$H_6$); $^{13}$C-NMR (75 MHz, $CDCl_3$) δ (ppm): 36.17, 42.99, 55.51, 57.49, 118.34, 121.41, 121.44, 123.28, 125.37, 126.54, 127.54, 128.59, 132.56, 133.50, 133.77, 134.04, 134.26, 136.61, 149.08, 149.67, 159.35, 160.11, 183.06, 184.73.

EXAMPLE 10

2-(((1,3-dioxolan-2-yl)-N-methylmethanamino)methyl)-1H-anthra[1,2-d]imidazole-6,11-dione (CL08)

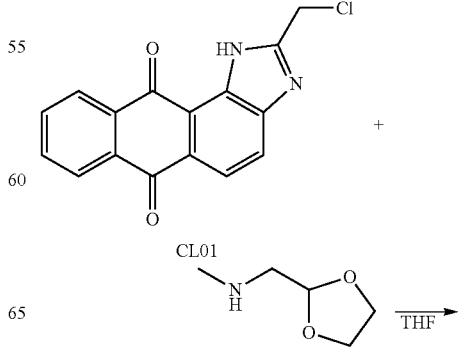

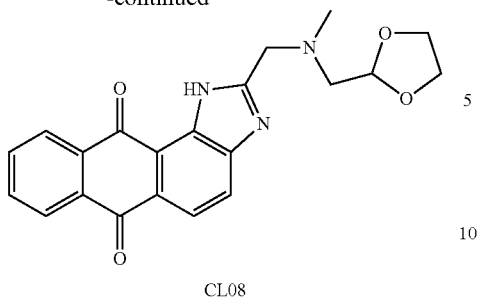

CL08

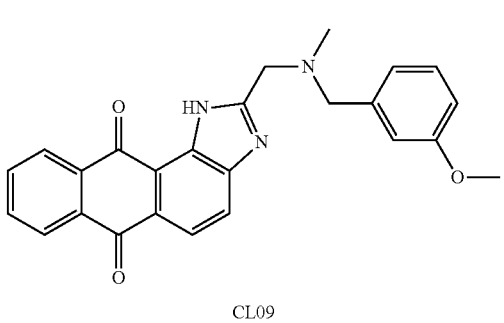

CL09

Compound CL01 (1.18 g, 4 mmole) and DIPEA (1.4 mL, 8 mmole) were stirred in 30 mL anhydrous tetrahydrofuran (THF) for 10 minutes. Then, 2-methylaminomethyl-1,3-dioxolane (0.91 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 377.3933 (C$_{21}$H$_{19}$N$_3$O$_4$); Yield: 59%; Mp: 161-162° C.; R$_f$: 0.76 (ethyl acetate:dichloromethane:methanol=2:2:1); HRMS (EI) m/z calcd for C$_{21}$H$_{19}$N$_3$O$_4^+$[M]$^+$: 397.1376. Found: 377.1395. $^1$H-NMR (300 MHz, CDCl$_3$) δ (ppm): 2.56 (s, 3H, —N—CH$_3$), 2.79 (d, J=4.2 Hz, 2H, —CH$_2$—), 3.97-4.16 (m, 4H, —CH$_2$—), 4.10 (s, 2H, —CH$_2$—), 5.14 (t, J=4.1 Hz, 1H, —CH—), 7.23-7.76 (m, 2H, Ar—H$_{8,9}$), 7.97 (d, J=8.4 Hz, 1H, Ar—H$_4$), 8.14 (d, J=8.4 Hz, 1H, Ar—H$_5$), 8.21-8.29 (m, 2H, Ar—H$_{7,10}$); $^{13}$C-NMR (75 MHz, CDCl$_3$) δ (ppm): 44.50, 56.03, 59.41, 65.09, 102.96, 118.39, 121.36, 125.24, 126.50, 127.46, 128.50, 132.33, 133.48, 133.67, 133.98, 134.15, 149.20, 158.92, 183.03, 184.57.

EXAMPLE 11

2-((3-methoxy-N-methybenzylamino)methyl)-1H-anthra[1,2-d]imidazole-6,11-dione (CL09)

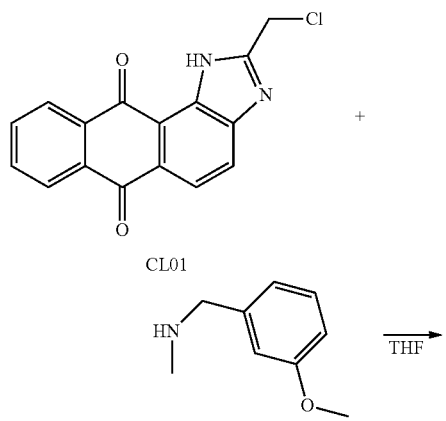

Compound CL01 (1.18 g, 4 mmole) and DIPEA (1.4 mL, 8 mmole) were stirred in 30 mL anhydrous tetrahydrofuran (THF) for 10 minutes. Then, 3-methoxy-N-methybenzylamine (1.19 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 411.4525 (C$_{25}$H$_{21}$N$_3$O$_3$); Yield: 39%; Mp: 150-151° C.; R$_f$: 0.79 (ethyl acetate:dichloromethane:methanol=2:2:1); HRMS (ESI) m/z calcd for C$_{25}$H$_{21}$N$_3$O$_3^+$[M]$^+$: 411.1583. Found: [M+H]$^+$=412.1701, [M+Na]$^+$=434.1519. $^1$H-NMR (300 MHz, CDCl$_3$) δ (ppm): 2.44 (s, 3H, —N—CH$_3$), 3.74 (s, 2H, —CH$_2$—), 3.86 (s, 3H, —O—CH$_3$), 4.01 (s, 2H, —CH$_2$—), 6.83 (d, J=7.8 Hz, 1H, Ar'—H), 7.03-7.00 (m, 2H, Ar'—H), 7.27 (t, J=6.9 Hz, 1H, Ar'—H), 7.77-7.80 (m, 2H, Ar—H$_{8,9}$), 7.99 (d, J=8.4 Hz, 1H, Ar—H$_4$), 8.17 (d, J=8.1 Hz, 1H, Ar—H$_5$), 8.23-8.32 (m, 2H, Ar—H$_{7,10}$); $^{13}$C-NMR (75 MHz, CDCl$_3$) δ (ppm): 29.15, 42.87, 54.97, 55.27, 62.17, 113.85, 114.55, 118.40, 121.54, 121.64, 125.53, 126.63, 127.62, 128.82, 129.74, 130.13, 132.61, 133.53, 133.82, 134.13, 134.33, 149.00, 160.23, 182.99, 184.88.

EXAMPLE 12

2-((di-(2-picolyl)amino)methyl)-1H-anthra[1,2-d]imidazole-6,11-dione (CL10)

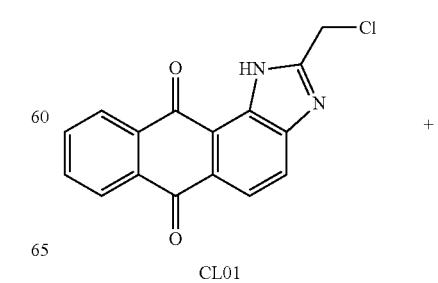

CL01

15
-continued

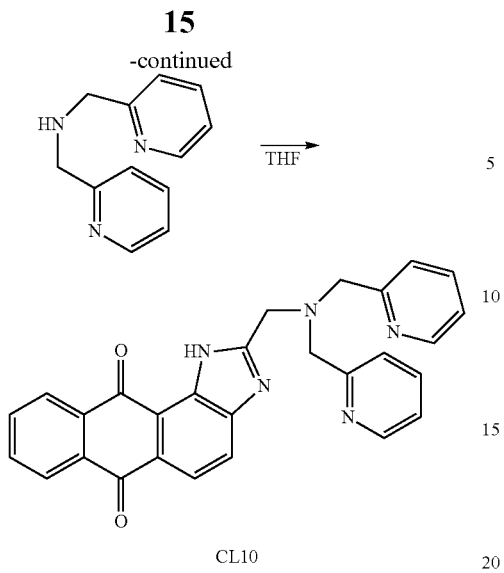

CL10

Compound CL01 (1.18 g, 4 mmole) and DIPEA (1.4 mL, 8 mmole) were stirred in 30 mL anhydrous tetrahydrofuran (THF) for 10 minutes. Then, di-(2-picolyl)amine (1.44 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 459.4986 (C$_{28}$H$_{21}$N$_5$O$_2$); Yield: 45%; Mp: 175-176° C.; R$_f$: 0.59 (ethyl acetate:dichloromethane:methanol=2:2:1); HRMS (Et) m/z calcd for C$_{28}$H$_{21}$N$_5$O$_2$$^+$[M]$^+$: 459.1695. Found: 459.1700. $^1$H-NMR (300 MHz, CDCl$_3$) δ (ppm): 4.04 (s, 4H, —N—CH$_2$—), 4.20 (s, 2H, —CH$_2$—), 7.25-7.29 (m, 2H, Ar'—H), 7.46 (d, J=7.5 Hz, 2H, Ar'—H), 7.67-7.73 (m, 2H, Ar'—H), 7.78-7.81 (m, 2H, Ar—H$_{8,9}$), 8.03 (d, J=8.4 Hz, 1H, Ar—H$_4$), 8.21 (d, J=8.4 Hz, 1H, Ar—H$_5$), 8.31-8.39 (m, 2H, Ar—H$_{7,10}$), 8.85-8.87 (m, 2H, Ar'—H); $^{13}$C-NMR (75 MHz, CDCl$_3$) δ (ppm): 51.87, 59.73, 118.92, 121.32, 122.71, 123.86, 124.01, 125.02, 126.68, 127.43, 128.64, 132.61, 133.68, 134.02, 134.06, 137.25, 149.03, 149.26, 149.58, 158.07, 159.30, 183.315, 184.44.

EXAMPLE 13

2-(((anthracen-10-yl)-N-methylmethanamino)methyl)-1H-anthra[1,2-d]imidazole-6,11-dione (CL11)

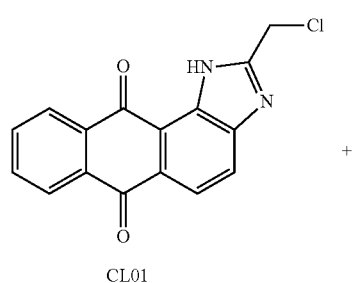

CL01

16
-continued

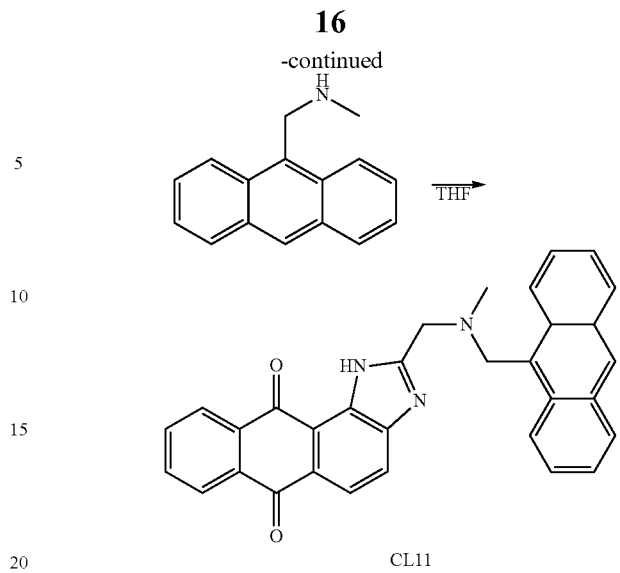

CL11

Compound CL01 (1.18 g, 4 mmole) and DIPEA (1.4 mL, 8 mmole) were stirred in 30 mL anhydrous tetrahydrofuran (THF) for 10 minutes. Then, 9-(methylaminomethyl)anthracene (0.88 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 481.5439 (C$_{32}$H$_{23}$N$_3$O$_2$); Yield: 66%; Mp: 189-190° C.; R$_f$: 0.45 (ethyl acetate:dichloromethane=1:1); HRMS (EI) m/z calcd for C$_{32}$H$_{23}$N$_3$O$_2$$^+$[M]$^+$: 481.1790. Found: 481.1790. $^1$H-NMR (300 MHz, CDCl$_3$) δ (ppm): 2.55 (s, 3H, —N—CH$_3$), 3.97 (s, 2H, —CH$_2$—), 4.69 (s, 2H, —CH$_2$—), 7.42-7.47 (m, 2H, Ar'—H), 7.60-7.66 (m, 2H, Ar'—H), 7.45 (d, J=7.8 Hz, 2H, Ar'—H), 7.73-7.76 (m, 2H, Ar—H$_{8,9}$), 7.85 (d, J=8.4 Hz, 1H, Ar—H$_4$), 7.92 (d, J=8.4 Hz, 2H, Ar'—H), 8.07 (d, J=8.1 Hz, 1H, Ar—H$_5$), 8.19-8.27 (m, 2H, Ar—H$_{7,10}$), 8.32 (s, 1H, Ar'—H), 8.51 (d, J=9.3 Hz, 2H, Ar'—H); $^{13}$C-NMR (75 MHz, CDCl$_3$) δ (ppm): 43.60, 53.72, 54.42, 118.00, 121.27, 124.29, 125.09, 126.50, 126.55, 127.46, 128.24, 128.39, 129.25, 131.37, 131.46, 132.22, 133.38, 133.68, 133.93, 134.15, 148.78, 158.99, 182.59, 184.37.

EXAMPLE 14

2-((2-(trifluoromethyl)benzylamino)methyl)-1H-anthra[1,2-d]imidazole-6,11-dione (CL12)

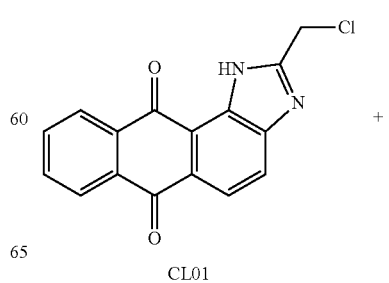

CL01

-continued

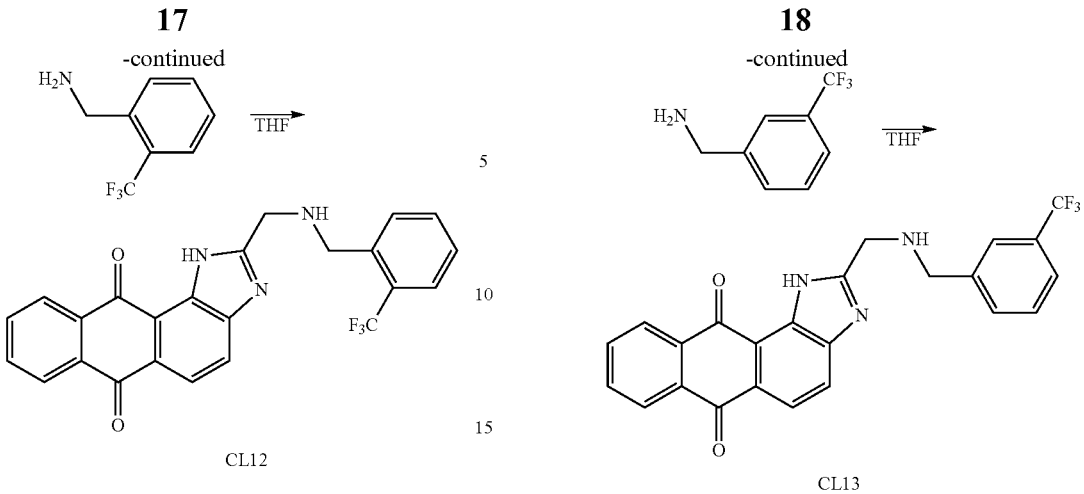

Compound CL01 (1.18 g, 4 mmole) and TEA (1.2 mL, 8 mmole) were stirred in 30 mL anhydrous tetrahydrofuran (THF) for 10 minutes. Then, 2-(trifluoromethyl)benzylamine (1.1 mL, 8 mmole) was added thereto. The mixed solution was reacted by heating under reflux for 8 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 435.3979 ($C_{24}H_{16}F_3N_3O_2$); Yield: 33%; Mp: 143-144° C.; $R_f$: 0.78 (ethyl acetate:dichloromethane:methanol=2:2:1); HRMS (EI) m/z calcd for $C_{24}H_{16}F_3N_3O_2{}^+[M]^+$: 435.1195. Found: 435.1189. $^1$H-NMR (300 MHz, $CDCl_3$) δ (ppm): 4.11 (s, 2H, —$CH_2$—), 4.23 (s, 2H, —$CH_2$—), 7.39 (t, J=7.5 Hz, 1H, Ar'—H), 7.57 (t, J=7.6 Hz, 1H, Ar'—H), 7.66-7.69 (m, 2H, Ar'—H), 7.76-7.80 (m, 2H, Ar—$H_{8,9}$), 7.97 (d, J=8.7 Hz, 1H, Ar—$H_4$), 8.14 (d, J=8.4 Hz, 1H, Ar—$H_5$), 8.20-8.30 (m, 2H, Ar—$H_{7,10}$); $^{13}$C-NMR (75 MHz, $CDCl_3$) δ (ppm): 46.83, 49.92, 53.24, 118.29, 121.58, 122.77, 125.13, 125.43, 126.34, 126.41, 126.59, 127.56, 128.66, 130.97, 132.24, 132.36, 133.39, 133.78, 134.03, 134.34, 148.94, 182.87, 184.84.

Compound CL01 (1.18 g, 4 mmole) and TEA (1.2 mL, 8 mmole) were stirred in 30 mL anhydrous tetrahydrofuran (THF) for 10 minutes. Then, 3-(trifluoromethyl)benzylamine (1.1 mL, 8 mmole) was added thereto. The mixed solution was reacted by heating under reflux for 8 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 435.3979 ($C_{24}H_{16}F_3N_3O_2$); Yield: 38%; Mp: 155-156° C.; $R_f$: 0.83 (ethyl acetate:dichloromethane:methanol=2:2:1); HRMS (EI) m/z calcd for $C_{24}H_{16}F_3N_3O_2{}^+[M]^+$: 435.1195. Found: 435.1190. $^1$H-NMR (300 MHz, $CDCl_3$) δ (ppm): 4.00 (s, 2H, —$CH_2$—), 4.23 (s, 2H, —$CH_2$—), 7.47-7.52 (m, 2H, Ar'—H), 7.60 (d, J=7.2 Hz, 1H, Ar'—H), 7.66 (s, 1H, Ar'—H), 7.79-7.82 (m, 2H, Ar—$H_{8,9}$), 8.02 (d, J=8.1 Hz, 1H, Ar—$H_4$), 8.20 (d, J=8.4 Hz, 1H, Ar—$H_5$), 8.26-8.35 (m, 2H, Ar—$H_{7,10}$); $^{13}$C-NMR (75 MHz, $CDCl_3$) δ (ppm): 46.98, 53.35, 53.24, 118.27, 121.60, 124.37, 124.41, 125.04, 125.10, 125.50, 126.59, 127.61, 128.69, 131.71, 132.40, 133.43, 133.82, 134.10, 134.38, 140.28, 149.03, 159.17, 182.92, 184.97.

EXAMPLE 15

2-((3-(trifluoromethyl)benzylamino)methyl)-1H-anthra[1,2-d]imidazole-6,11-dione (CL13)

EXAMPLE 16

2-((4-(trifluoromethyl)benzylamino)methyl)-1H-anthra[1,2-d]imidazole-6,11-dione (CL14)

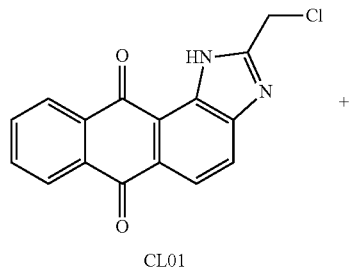

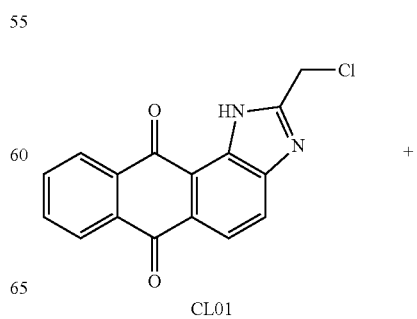

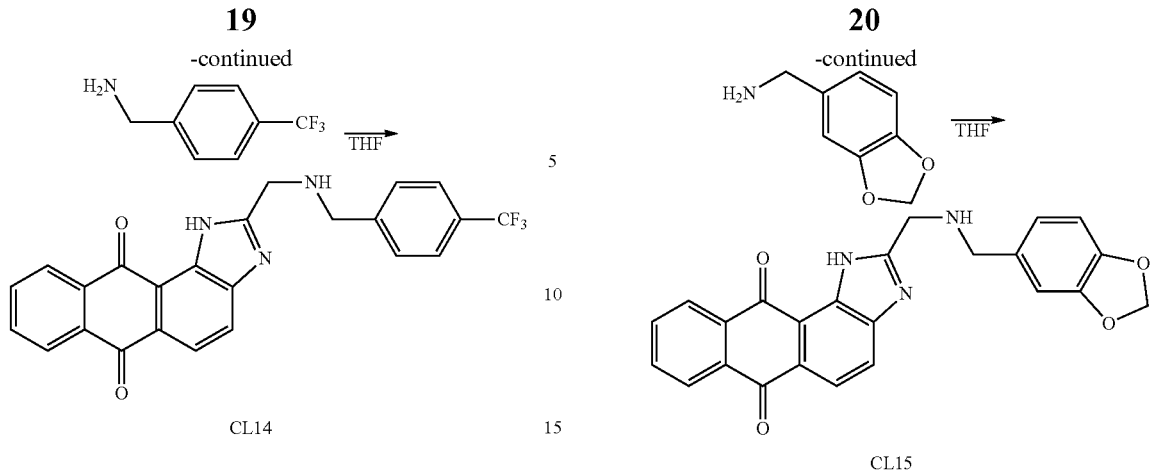

Compound CL01 (1.18 g, 4 mmole) and TEA (1.2 mL, 8 mmole) were stirred in 30 mL anhydrous tetrahydrofuran (THF) for 10 minutes. Then, 4-(trifluoromethyl)benzylamine (1.1 mL, 8 mmole) was added thereto. The mixed solution was reacted by heating under reflux for 8 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 435.3979 (C$_{24}$H$_{16}$F$_3$N$_3$O$_2$); Yield: 40%; Mp: 158-159° C.; R$_f$: 0.90 (ethyl acetate:dichloromethane:methanol=2:2:1); HRMS (ESI) m/z calcd for C$_{24}$H$_{16}$F$_3$N$_3$O$_2{}^+$[M]$^+$: 435.1195. Found: [M+H]$^+$=436.1318, [M+Na]$^+$=458.1143. $^1$H-NMR (300 MHz, CDCl$_3$) δ (ppm): 4.00 (s, 2H, —CH$_2$—), 4.22 (s, 2H, —CH$_2$—), 7.52 (d, J=7.8 Hz, 2H, Ar'—H), 7.60 (d, J=8.1 Hz, 2H, Ar'—H), 7.78-7.84 (m, 2H, Ar—H$_{8,9}$), 8.03 (d, J=8.4 Hz, 1H, Ar—H$_4$), 8.21 (d, J=8.1 Hz, 1H, Ar—H$_5$), 8.25-8.37 (m, 2H, Ar—H$_{7,10}$); $^{13}$C-NMR (75 MHz, CDCl$_3$) δ (ppm): 46.98, 53.35, 53.24, 118.27, 121.60, 124.37, 124.41, 125.04, 125.10, 125.50, 126.59, 127.61, 128.69, 131.71, 132.40, 133.43, 133.82, 134.10, 134.38, 140.28, 149.03, 159.17, 182.92, 184.97.

Compound CL01 (1.18 g, 4 mmole) and TEA (1.2 mL, 8 mmole) were stirred in 30 mL anhydrous tetrahydrofuran (THF) for 10 minutes. Then, piperonylamine (1 mL, 8 mmole) was added thereto. The mixed solution was reacted by heating under reflux for 8 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 411.4095 (C$_{24}$H$_{17}$N$_3$O$_4$); Yield: 50%; Mp: 166-167° C.; R$_f$: 0.71 (ethyl acetate:dichloromethane:methanol=2:2:1); HRMS (EI) m/z calcd for C$_{24}$H$_{17}$N$_3$O$_4{}^+$[M]$^+$: 435.1219. Found: 435.1218. $^1$H-NMR (300 MHz, CDCl$_3$) δ (ppm): 3.83 (s, 2H, —CH$_2$—), 4.18 (s, 2H, —CH$_2$—), 5.92 (s, 2H, —O—CH$_2$—), 6.74-7.94 (m, 2H, Ar'—H), 6.89 (s, 1H, Ar'—H), 7.78-7.80 (m, 2H, Ar—H$_{8,9}$), 8.00 (d, J=8.1 Hz, 1H, Ar—H$_4$), 8.18 (d, J=8.4 Hz, 1H, Ar—H$_5$), 8.24-8.33 (m, 2H, Ar—H$_{7,10}$); $^{13}$C-NMR (75 MHz, CDCl$_3$) δ (ppm): 46.74, 53.71, 101.03, 108.31, 108.81, 118.26, 121.55, 121.61, 125.44, 126.60, 127.62, 128.62, 132.42, 133.28, 133.52, 133.79, 134.17, 134.35, 147.10, 148.13, 149.23, 159.86, 182.98, 184.99.

EXAMPLE 17

2-((piperonylamino)methyl)-1H-anthra[1,2-d]imidazole-6,11-dione (CL15)

EXAMPLE 18

2-((piperidin-1-yl)methyl)-1H-anthra[1,2-d]imidazole-6,11-dione (CL16)

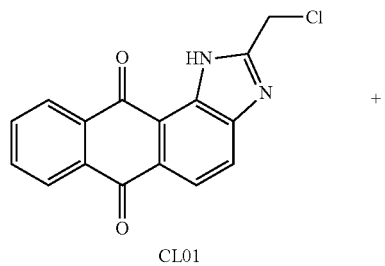

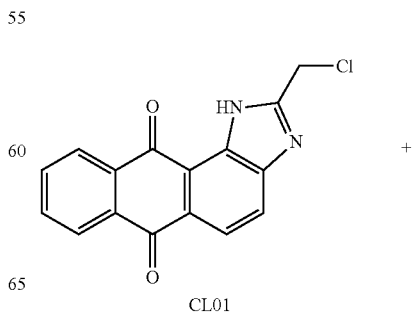

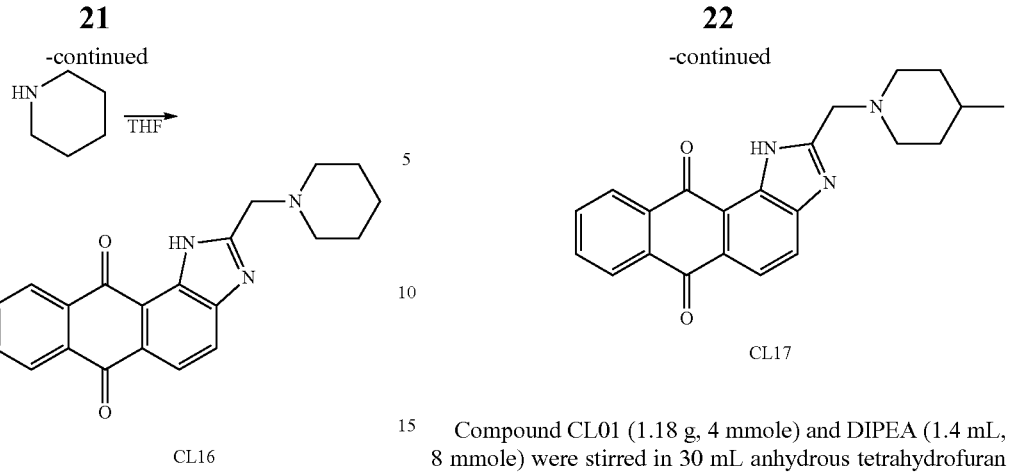

Compound CL01 (1.18 g, 4 mmole) and DIPEA (1.4 mL, 8 mmole) were stirred in 30 mL anhydrous tetrahydrofuran (THF) for 10 minutes. Then, piperidine (0.79 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 345.3945 (C$_{21}$H$_{19}$N$_3$O$_2$); Yield: 58%; Mp: 204-205° C.; R$_f$: 0.69 (ethyl acetate:dichloromethane:methanol=2:2:1); HRMS (EI) m/z calcd for C$_{21}$H$_{19}$N$_3$O$_2{}^+$[M]$^+$: 345.1477. Found: 345.1468. $^1$H-NMR (300 MHz, CDCl$_3$) δ (ppm): 1.52-1.54 (m, 2H, —CH$_2$—), 1.68-1.75 (m, 4H, —CH$_2$—), 2.16 (s, 4H, —CH$_2$—), 3.94 (s, 2H, —CH$_2$—), 7.77-7.80 (m, 2H, Ar—H$_{8,9}$), 8.09 (d, J=8.4 Hz, 1H, Ar—H$_4$), 8.18 (d, J=8.4 Hz, 1H, Ar—H$_5$), 8.24-8.32 (m, 2H, Ar—H$_{7,10}$); $^{13}$C-NMR (75 MHz, CDCl$_3$) δ (ppm): 23.66, 25.62, 54.98, 56.92, 118.44, 121.51, 125.51, 126.65, 127.59, 128.79, 132.61, 133.55, 133.82, 134.12, 134.32, 149.07, 158.11, 183.03, 184.92.

Compound CL01 (1.18 g, 4 mmole) and DIPEA (1.4 mL, 8 mmole) were stirred in 30 mL anhydrous tetrahydrofuran (THF) for 10 minutes. Then, 4-methylpiperidine (0.95 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 359.4210 (C$_{22}$H$_{21}$N$_3$O$_2$); Yield: 63%; Mp: 208-209° C.; R$_f$: 0.74 (ethyl acetate:dichloromethane:methanol=2:2:1); HRMS (ESI) m/z calcd for C$_{22}$H$_{21}$N$_3$O$_2{}^+$[M]$^+$: 359.1634. Found: [M+H]$^+$=360.1742, [M+Na]$^+$=382.1562. $^1$H-NMR (300 MHz, CDCl$_3$) δ (ppm): 0.98 (d, J=5.1 Hz, 3H, —CH$_3$), 1.47 (s, 3H, —CH$_2$—, —CH—), 1.70-1.73 (m, 2H, —CH$_2$—), 3.35 (t, 2H, J=10.4 Hz, N—CH$_2$—), 3.02 (d, 2H, J=10.8 Hz, N—CH$_2$—), 4.02 (s, 2H, —CH$_2$—), 7.78-7.81 (m, 2H, Ar—H$_{8,9}$), 8.01 (d, J=8.4 Hz, 1H, Ar—H$_4$), 8.19 (d, J=8.4 Hz, 1H, Ar—H$_5$), 8.27-8.34 (m, 2H, Ar—H$_{7,10}$); $^{13}$C-NMR (75 MHz, CDCl$_3$) δ (ppm): 21.21, 29.81, 30.60, 32.99, 44.00, 53.97, 55.84, 115.55, 121.61, 125.53, 126.83, 127.54, 129.15, 132.71, 133.53, 133.87, 134.02, 134.27, 183.04, 184.54.

EXAMPLE 19

2-((4-methylpiperidin-1-yl)methyl)-1H-anthra[1,2-d]imidazole-6,11-dione (CL17)

EXAMPLE 20

2-((azepan-1-yl)methyl)-1H-anthra[1,2-d]imidazole-6,11-dione (CL18)

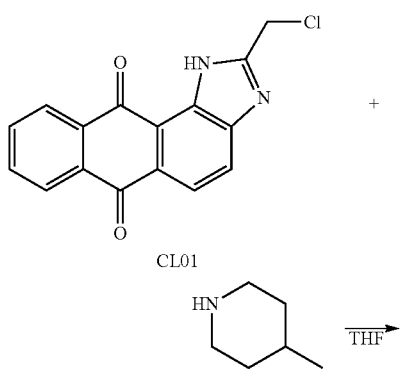

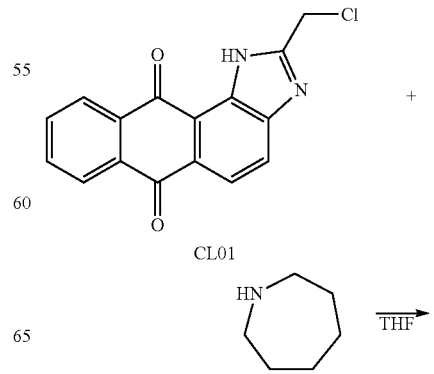

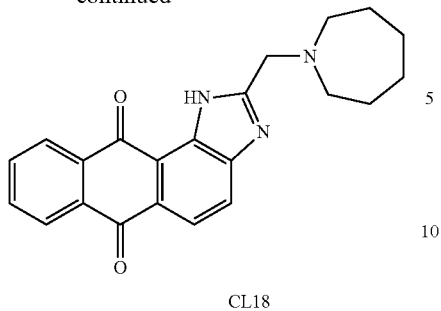

CL18

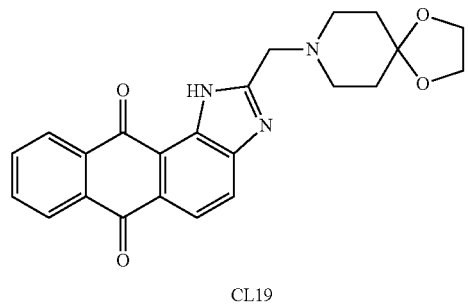

CL19

Compound CL01 (1.18 g, 4 mmole) and DIPEA (1.4 mL, 8 mmole) were stirred in 30 mL anhydrous tetrahydrofuran (THF) for 10 minutes. Then, hexamethyleneimine (0.90 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 359.4210 (C$_{22}$H$_{21}$N$_3$O$_2$); Yield: 53%; Mp: 183-184° C.; R$_f$: 0.67 (ethyl acetate:dichloromethane:methanol=2:2:1); HRMS (ESI) m/z calcd for C$_{22}$H$_{21}$N$_3$O$_2{}^+$[M]$^+$: 359.1634. Found: [M+H]$^+$=360.1746, [M+Na]$^+$=382.1559. $^1$H-NMR (300 MHz, CDCl$_3$) δ (ppm): 1.72-1.81 (m, 8H, —CH$_2$—), 2.92 (t, 4H, J=5.3 Hz, N—CH$_2$—), 4.19 (s, 2H, —CH$_2$—), 7.77-7.80 (m, 2H, Ar—H$_{8,9}$), 8.00 (d, J=8.4 Hz, 1H, Ar—H$_4$), 8.18 (d, J=8.4 Hz, 1H, Ar—H$_5$), 8.27-8.33 (m, 2H, Ar—H$_{7,10}$); $^{13}$C-NMR (75 MHz, CDCl$_3$) δ (ppm): 26.81, 28.15, 56.33, 56.50, 118.16, 121.42, 125.37, 126.55, 127.54, 128.49, 132.37, 133.42, 133.76, 134.02, 134.28, 149.19, 159.78, 182.96, 184.96.

EXAMPLE 21

2-((1,4-dioxa-8-azaspiro[4.5]decane-8-yl)methyl)-1H-anthra[1,2-d]imidazole-6,11-dione (CL19)

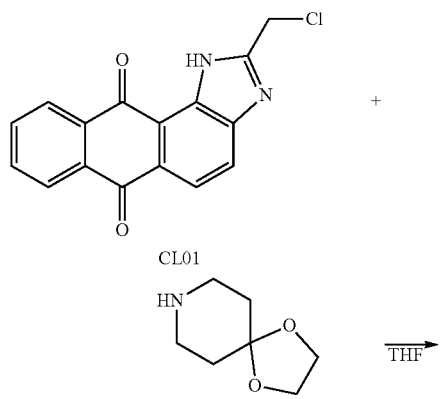

Compound CL01 (1.18 g, 4 mmole) and DIPEA (1.4 mL, 8 mmole) were stirred in 30 mL anhydrous tetrahydrofuran (THF) for 10 minutes. Then, 1,4-dioxa-8-azaspiro[4.5]decane (1.03 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 403.4305 (C$_{23}$H$_{21}$N$_3$O$_4$); Yield: 60%; Mp: 219-220° C.; R$_f$: 0.68 (ethyl acetate:dichloromethane:methanol=2:2:1); HRMS (EI) m/z calcd for C$_{23}$H$_{21}$N$_3$O$_4{}^+$[M]$^+$: 403.1532. Found: 403.1530. $^1$H-NMR (300 MHz, CDCl$_3$) δ (ppm): 1.87 (t, J=5.6 Hz, 4H, —CH$_2$—), 2.78 (t, J=5.4 Hz, 4H, N—CH$_2$—), 3.97 (s, 4H, O—CH$_2$—), 4.01 (s, 2H, —CH$_2$—), 7.76-7.79 (m, 2H, Ar—H$_{8,9}$), 7.99 (d, J=8.4 Hz, 1H, Ar—H$_4$), 8.16 (d, J=8.4 Hz, 1H, Ar—H$_5$), 8.22-8.31 (m, 2H, Ar—H$_{7,10}$); $^{13}$C-NMR (75 MHz, CDCl$_3$) δ (ppm): 34.47, 51.92, 55.77, 64.37, 116.36, 118.48, 121.54, 125.57, 126.66, 127.57, 128.87, 132.60, 133.45, 133.85, 134.03, 134.33, 148.88, 182.97, 184.81.

EXAMPLE 22

2-((4-(3-(piperidin-4-yl)propyl)piperidin-1-yl)methyl)-1H-anthra[1,2-d]imidazole-6,11-dione (CL20)

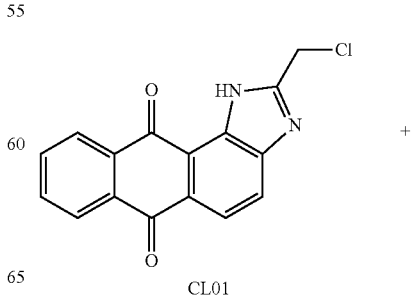

CL01

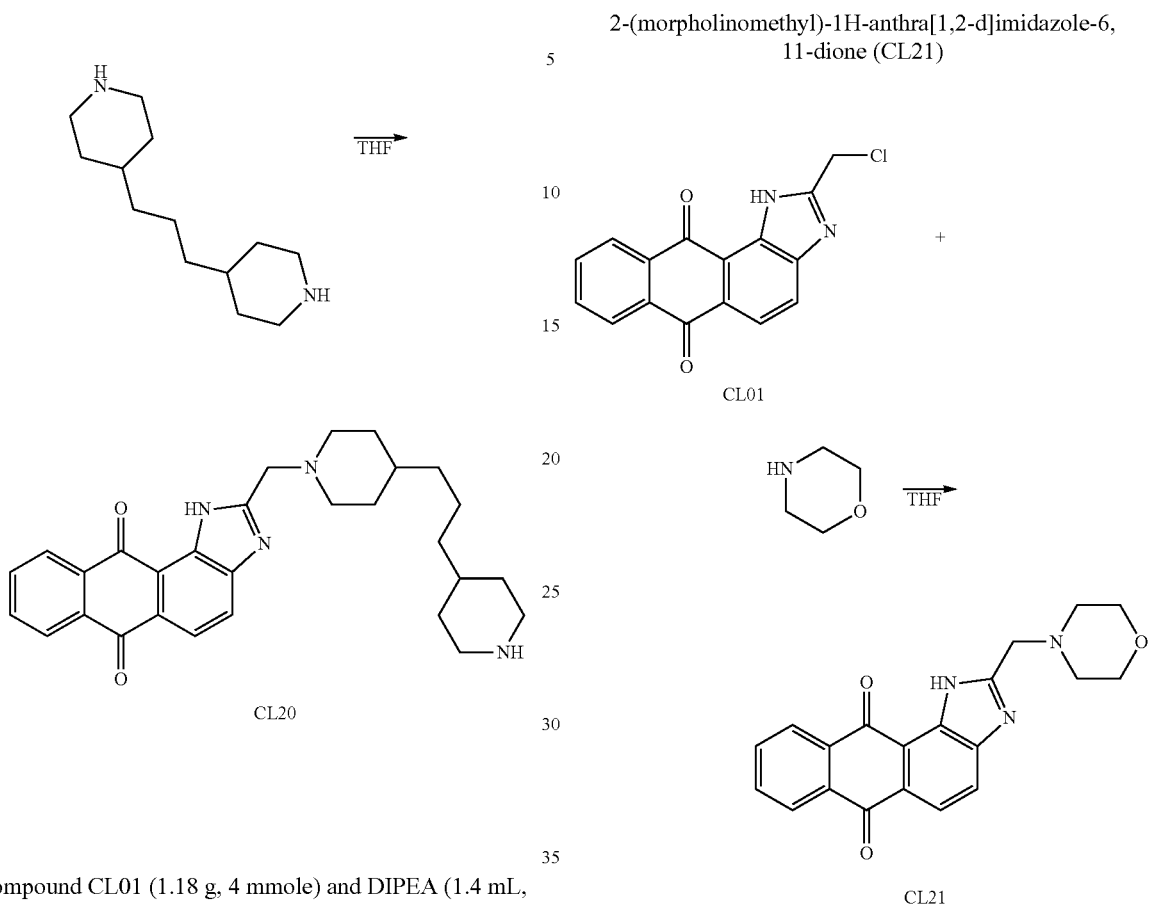

Compound CL01 (1.18 g, 4 mmole) and DIPEA (1.4 mL, 8 mmole) were stirred in 30 mL anhydrous tetrahydrofuran (THF) for 10 minutes. Then, 4,4'-trimethylenebis-(1-methylpiperidine) (1.68 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 470.6059 (C$_{29}$H$_{34}$N$_4$O$_2$); Yield: 40%; Mp: 172-173° C.; R$_f$: 0.60 (ethyl acetate:dichloromethane:methanol=2:2:1); HRMS (EI) m/z calcd for C$_{29}$H$_{34}$N$_4$O$_2{}^+$[M]$^+$: 470.2682. Found: 470.2689. $^1$H-NMR (300 MHz, CDCl$_3$) δ (ppm): 1.04-1.28 (m, 12H, —CH$_2$—, —CH—), 1.64-1.68 (m, 4H, —CH$_2$—), 2.14-2.21 (m, 2H, N—CH$_{2(axial)}$—), 2.54-2.62 (m, 2H, N—CH$_{2(axial)}$—), 2.90 (d, 2H, J=11.4 Hz, N—CH$_{2(equatorial)}$—), 3.07 (d, 2H, J=12.3 Hz, N—CH$_{2(equatorial)}$—), 3.86 (s, 2H, —CH$_2$—), 7.74-7.81 (m, 2H, Ar—H$_{8,9}$), 8.00 (d, J=8.4 Hz, 1H, Ar—H$_4$), 8.17 (d, J=8.4 Hz, 1H, Ar—H$_5$), 8.20-8.32 (m, 2H, Ar—H$_{7,10}$); $^{13}$C-NMR (75 MHz, CDCl$_3$) δ (ppm): 23.49, 32.34, 33.26, 35.29, 36.02, 36.56, 37.22, 46.53, 54.60, 56.86, 118.20, 121.44, 125.46, 126.52, 127.59, 128.57, 132.51, 133.44, 133.80, 134.05, 134.33, 149.10, 159.17, 182.99, 185.05.

EXAMPLE 23

2-(morpholinomethyl)-1H-anthra[1,2-d]imidazole-6,11-dione (CL21)

Compound CL01 (1.18 g, 4 mmole) and DIPEA (1.4 mL, 8 mmole) were stirred in 30 mL anhydrous tetrahydrofuran (THF) for 10 minutes. Then, morpholine (0.69 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 347.3673 (C$_{20}$H$_{17}$N$_3$O$_3$); Yield: 55%; Mp: 241-242° C.; R$_f$: 0.75 (ethyl acetate:dichloromethane:methanol=2:2:1); HRMS (ESI) m/z calcd for C$_{20}$H$_{17}$N$_3$O$_3{}^+$[M]$^+$: 347.1270. Found: [M+H]$^+$=348.1379, [M+Na]$^+$=370.1198. $^1$H-NMR (300 MHz, CDCl$_3$) δ (ppm): 2.64 (t, J=4.5 Hz, 4H, N—CH$_2$—), 3.81 (t, J=4.7 Hz, 4H, O—CH$_2$—), 3.93 (s, 2H, —CH$_2$—), 7.76-7.80 (m, 2H, Ar—H$_{8,9}$), 8.00 (d, J=8.4 Hz, 1H, Ar—H$_4$), 8.16 (d, J=8.4 Hz, 1H, Ar—H$_5$), 8.21-8.31 (m, 2H, Ar—H$_{7,10}$); $^{13}$C-NMR (75 MHz, CDCl$_3$) δ (ppm): 53.90, 56.74, 66.72, 118.26, 121.57, 121.65, 126.54, 127.61, 128.77, 132.52, 133.35, 133.85, 134.00, 134.42, 148.84, 157.44, 182.87, 185.02.

EXAMPLE 24

2-(thiomorpholinomethyl)-1H-anthra[1,2-d]imidazole-6,11-dione (CL22)

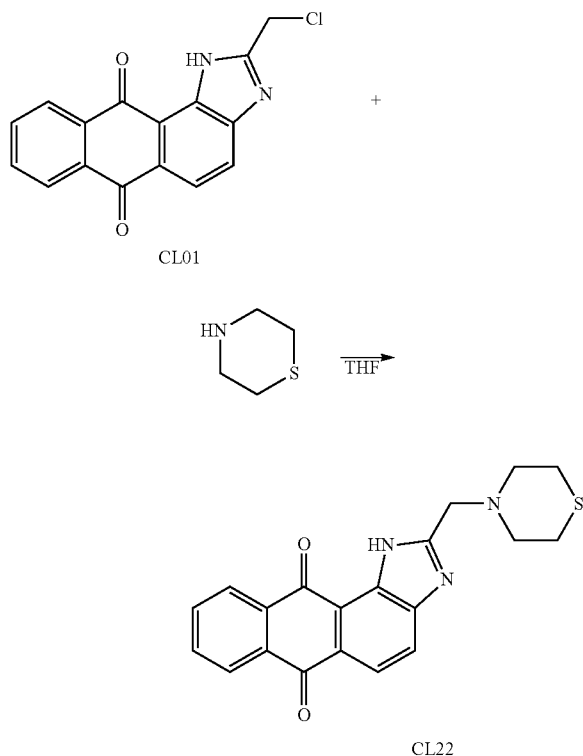

Compound CL01 (1.18 g, 4 mmole) and DIPEA (1.4 mL, 8 mmole) were stirred in 30 mL anhydrous tetrahydrofuran (THF) for 10 minutes. Then, thiomorpholine (0.80 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 363.4329 (C$_{20}$H$_{17}$N$_3$O$_2$S); Yield: 59%; Mp: 216-217° C.; R$_f$: 0.76 (ethyl acetate:dichloromethane:methanol=2:2:1); HRMS (ESI) m/z calcd for C$_{20}$H$_{17}$N$_3$O$_2$S$^+$[M]$^+$: 363.1041. Found: [M+H]$^+$=364.1141, [M+Na]$^+$=386.0907. $^1$H-NMR (300 MHz, CDCl$_3$) δ (ppm): 2.82 (t, J=4.7 Hz, 4H, S—CH$_2$—), 2.96 (t, J=4.8 Hz, 4H, N—CH$_2$—), 4.02 (s, 2H, —CH$_2$—), 7.78-7.81 (m, 2H, Ar—H$_{8,9}$), 8.01 (d, J=8.4 Hz, 1H, Ar—H$_4$), 8.18 (d, J=8.7 Hz, 1H, Ar—H$_5$), 8.23-8.33 (m, 2H, Ar—H$_{7,10}$); $^{13}$C-NMR (75 MHz, CDCl$_3$) δ (ppm): 27.56, 55.32, 56.93, 118.45, 121.64, 125.67, 126.65, 127.64, 128.95, 132.59, 133.44, 133.89, 134.06, 134.42, 148.87, 156.97, 182.91, 184.96.

EXAMPLE 25

2-((thiazolidin-3-yl)methyl)-1H-anthra[1,2-d]imidazole-6,11-dione (CL23)

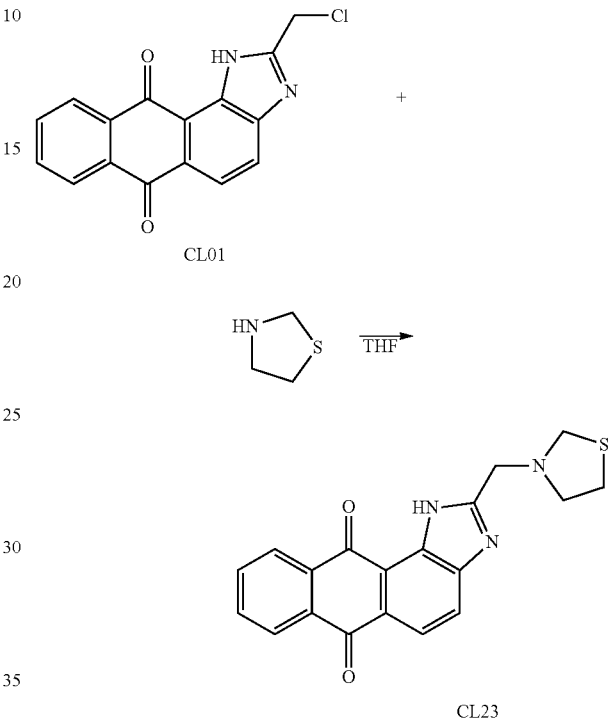

Compound CL01 (1.18 g, 4 mmole) and DIPEA (1.4 mL, 8 mmole) were stirred in 30 mL anhydrous tetrahydrofuran (THF) for 10 minutes. Then, thiazolidine (0.63 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/H$_2$O. The extract was dried by MgSO$_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 349.4063 (C$_{19}$H$_{15}$N$_3$O$_2$S); Yield: 48%; Mp: 195-196° C.; R$_f$: 0.28 (ethyl acetate:dichloromethane=1:1); HRMS (ESI) m/z calcd for C$_{19}$H$_{15}$N$_3$O$_2$S$^+$[M]$^+$: 349.0885. Found: [M+H]$^+$=350.0999, [M+Na]$^+$=372.0816. $^1$H-NMR (300 MHz, CDCl$_3$) δ (ppm): 3.10 (t, J=6.5 Hz, 2H, S—CH$_2$—), 3.31 (t, J=6.5 Hz, 2H, N—CH$_2$—), 4.13 (s, 2H, —CH$_2$—), 4.24 (s, 2H, —CH$_2$—), 7.79-7.83 (m, 2H, Ar—H$_{8,9}$), 8.01 (d, J=8.4 Hz, 1H, Ar—H$_4$), 8.19 (d, J=8.4 Hz, 1H, Ar—H$_5$), 8.23-8.35 (m, 2H, Ar—H$_{7,10}$); $^{13}$C-NMR (75 MHz, CDCl$_3$) δ (ppm): 52.11, 58.09, 60.86, 118.41, 121.69, 125.79, 126.69, 127.69, 128.92, 132.60, 133.49, 133.86, 134.16, 134.31, 134.45, 140.07, 158.11, 182.92, 185.12.

EXAMPLE 26

2-((4-methylpiperazin-1-yl)methyl)-1H-anthra[1,2-d]imidazole-6,11-dione (CL24)

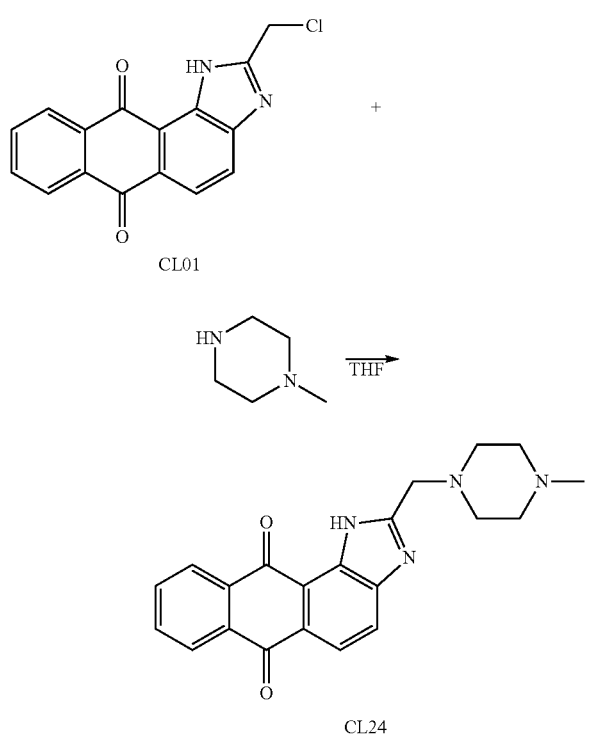

Compound CL01 (1.18 g, 4 mmole) and DIPEA (1.4 mL, 8 mmole) were stirred in 30 mL anhydrous tetrahydrofuran (THF) for 10 minutes. Then, N-methylpiperazine (0.88 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 360.4091 ($C_{21}H_{20}N_4O_2$); Yield: 70%; Mp: 231-232° C.; $R_f$: 0.20 (ethyl acetate:dichloromethane:methanol=1:1:1); HRMS (EI) m/z calcd for $C_{21}H_{20}N_4O_2^+[M]^+$: 360.1586. Found: 360.1585. $^1$H-NMR (300 MHz, $CDCl_3$) δ (ppm): 2.37 (s, 3H, N—$CH_3$), 2.61-2.69 (m, 8H, N—$CH_2$—), 3.92 (s, 2H, —$CH_2$—), 7.76-7.79 (m, 2H, Ar—$H_{8,9}$), 8.00 (d, J=8.4 Hz, 1H, Ar—$H_4$), 8.16 (d, J=8.4 Hz, 1H, Ar—$H_5$), 8.22-8.32 (m, 2H, Ar—$H_{7,10}$); $^{13}$C-NMR (75 MHz, $CDCl_3$) δ (ppm): 45.64, 53.27, 54.85, 56.28, 118.26, 121.54, 125.66, 126.53, 127.63, 128.75, 132.55, 133.47, 133.80, 134.06, 134.38, 149.07, 158.18, 182.89, 185.10.

EXAMPLE 27

2-((4-ethylpiperazin-1-yl)methyl)-1H-anthra[1,2-d]imidazole-6,11-dione (CL25)

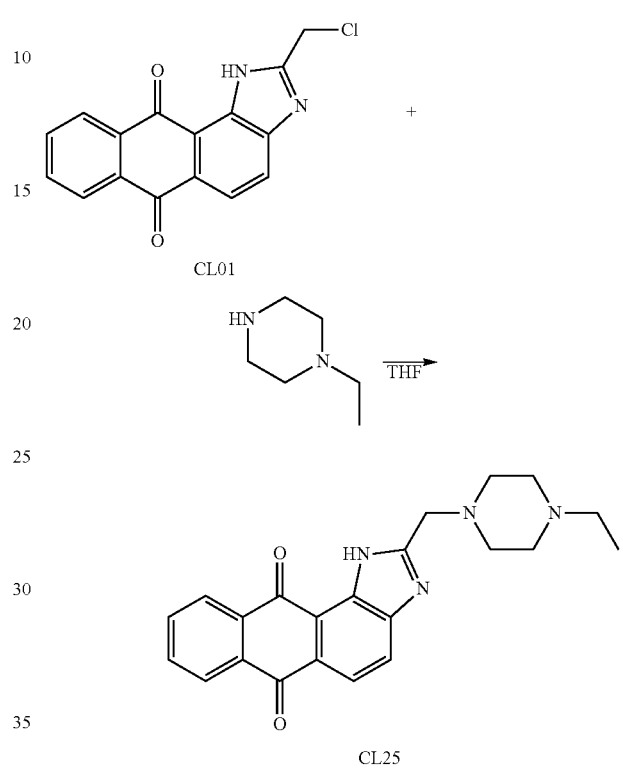

Compound CL01 (1.18 g, 4 mmole) and DIPEA (1.4 mL, 8 mmole) were stirred in 30 mL anhydrous tetrahydrofuran (THF) for 10 minutes. Then, 1-ethylpiperazine (1.02 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 374.4357 ($C_{22}H_{22}N_4O_2$); Yield: 64%; Mp: 204-205° C.; $R_f$: 0.18 (ethyl acetate:dichloromethane:methanol=2:2:1); HRMS (EI) m/z calcd for $C_{22}H_{22}N_4O_2^+[M]^+$: 374.1743. Found: 374.1736. $^1$H-NMR (300 MHz, $CDCl_3$) δ (ppm): 1.09 (t, J=7.2 Hz, 3H, —$CH_3$), 2.46 (q, J=7.2 Hz, 2H, N—$CH_2$—), 2.58-2.67 (m, 8H, N—$CH_2$—), 3.91 (s, 2H, —$CH_2$—), 7.75-7.77 (m, 2H, Ar—$H_{8,9}$), 7.99 (d, J=8.4 Hz, 1H, Ar—$H_4$), 8.14 (d, J=8.4 Hz, 1H, Ar—$H_5$), 8.19-8.29 (m, 2H, Ar—$H_{7,10}$); $^{13}$C-NMR (75 MHz, $CDCl_3$) δ (ppm): 11.75, 52.13, 52.55, 53.49, 56.35, 118.17, 121.48, 125.57, 126.49, 127.57, 128.62, 132.48, 133.36, 133.79, 134.00, 134.35, 148.97, 158.31, 182.88, 185.01.

EXAMPLE 28

2-((4-allylpiperazin-1-yl)methyl)-1H-anthra[1,2-d]imidazole-6,11-dione (CL26)

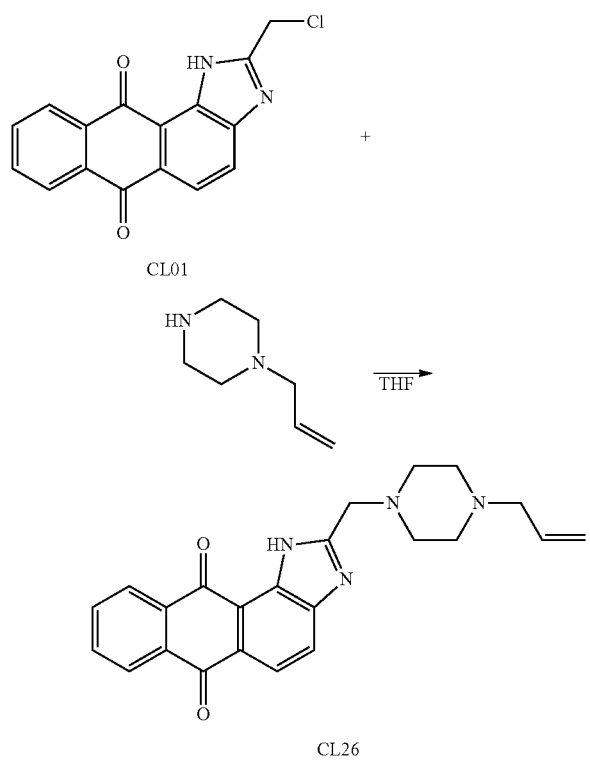

Compound CL01 (1.18 g, 4 mmole) and DIPEA (1.4 mL, 8 mmole) were stirred in 30 mL anhydrous tetrahydrofuran (THF) for 10 minutes. Then, 1-allylpiperazine (1.12 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 386.4464 ($C_{23}H_{22}N_4O_2$); Yield: 54%; Mp: 175-176° C.; $R_f$: 0.45 (ethyl acetate:dichloromethane:methanol=2:2:1); HRMS (EI) m/z calcd for $C_{23}H_{22}N_4O_2^+[M]^+$: 386.1743. Found: 386.1734. $^1$H-NMR (300 MHz, $CDCl_3$) δ (ppm): 2.81 (s, 8H, N—$CH_2$—), 3.22 (d, J=6.6 Hz, 2H, C=$CH_2$), 3.97 (s, 2H, —$CH_2$—), 5.32 (d, J=6.9 Hz, 2H, —$CH_2$—), 5.97 (m, 1H, C=CH—), 7.77-7.84 (m, 2H, Ar—$H_{8,9}$), 8.04 (d, J=8.4 Hz, 1H, Ar—$H_4$), 8.21 (d, J=8.7 Hz, 1H, Ar—$H_5$), 8.23-8.35 (m, 2H, Ar—$H_{7,10}$); $^{13}$C-NMR (75 MHz, $CDCl_3$) δ (ppm): 29.60, 52.37, 52.62, 56.10, 61.02, 118.34, 120.25, 125.76, 126.57, 127.69, 128.86, 132.58, 133.46, 133.86, 134.00, 134.13, 134.46, 149.03, 157.66, 182.93, 185.16.

EXAMPLE 29

2-((4-phenylpiperazin-1-yl)methyl)-1H-anthra[1,2-d]imidazole-6,11-dione (CL27)

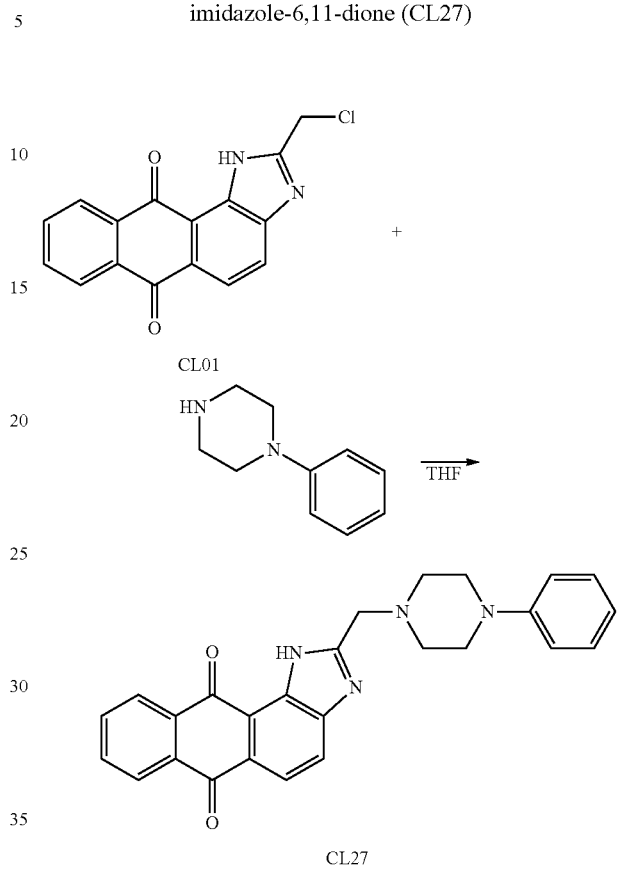

Compound CL01 (1.18 g, 4 mmole) and DIPEA (1.4 mL, 8 mmole) were stirred in 30 mL anhydrous tetrahydrofuran (THF) for 10 minutes. Then, N-phenylpiperazine (1.22 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 422.4785 ($C_{26}H_{22}N_4O_2$); Yield: 68%; Mp: 212-213° C.; $R_f$: 0.44 (ethyl acetate:dichloromethane=1:1); HRMS (Et) m/z calcd for $C_{26}H_{22}N_4O_2^+[M]^+$: 422.1743. Found: 422.1744. $^1$H-NMR (300 MHz, $CDCl_3$) δ (ppm): 2.82 (t, J=4.8 Hz, 4H, N—$CH_2$—), 3.01 (t, J=4.8 Hz, 4H, N—$CH_2$—), 4.02 (s, 2H, —$CH_2$—), 6.88-6.95 (m, 3H, Ar'—H), 7.24-7.30 (m, 2H, Ar'—H), 7.76-7.79 (m, 2H, Ar—$H_{8,9}$), 8.07 (d, J=8.7 Hz, 1H, Ar—$H_4$), 8.17 (d, J=8.1 Hz, 1H, Ar—$H_5$), 8.20-8.31 (m, 2H, Ar—$H_{7,10}$); $^{13}$C-NMR (75 MHz, $CDCl_3$) δ (ppm): 49.06, 52.52, 56.30, 116.35, 118.28, 120.15, 121.54, 125.60, 126.54, 127.57, 128.74, 129.22, 132.52, 133.33, 133.84, 133.96, 134.38, 148.85, 151.12, 157.58, 182.88, 184.93.

EXAMPLE 30

2-((4-(pyridin-2-yl)piperazin-1-yl)methyl)-1H-anthra[1,2-d]imidazole-6,11-dione (CL28)

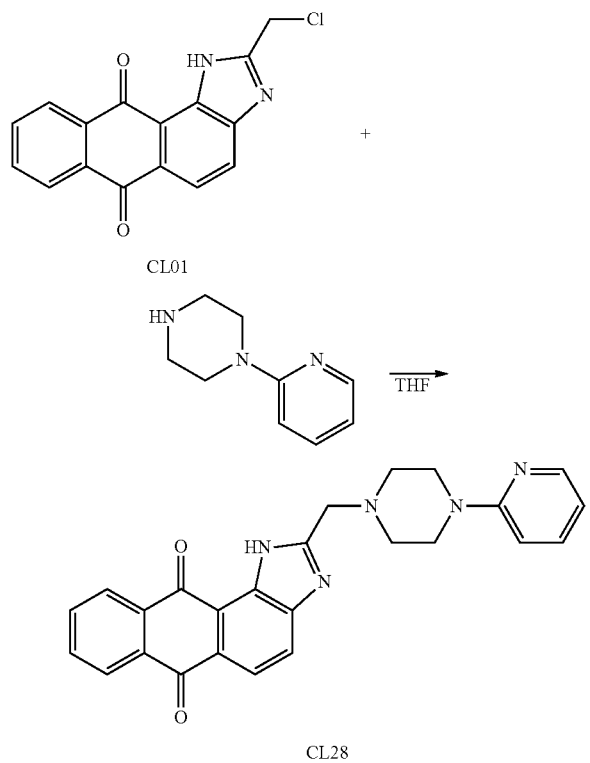

Compound CL01 (1.18 g, 4 mmole) and DIPEA (1.4 mL, 8 mmole) were stirred in 30 mL anhydrous tetrahydrofuran (THF) for 10 minutes. Then, 1-(2-pyridyl)piperazine (1.21 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 423.4665 ($C_{25}H_{21}N_5O_2$); Yield: 63%; Mp: 200-201° C.; $R_f$: 0.23 (ethyl acetate:dichloromethane=1:1); HRMS (EI) m/z calcd for $C_{25}H_{21}N_5O_2^+$[M]$^+$: 423.1695. Found: 423.1694. $^1$H-NMR (300 MHz, $CDCl_3$) δ (ppm): 2.80 (t, J=4.8 Hz, 4H, N—$CH_2$—), 3.69 (t, J=5.0 Hz, 4H, N—$CH_2$—), 4.04 (s, 2H, —$CH_2$—), 6.64-6.68 (m, 2H, Ar'—H), 7.48-7.51 (m, 1H, Ar'—H), 7.77-7.80 (m, 2H, Ar—$H_{8,9}$), 8.03 (d, J=8.4 Hz, 1H, Ar—$H_4$), 8.33-8.17 (m, 3H, Ar—$H_5$, Ar—$H_{7,10}$); $^{13}$C-NMR (75 MHz, $CDCl_3$) δ (ppm): 45.17, 53.36, 56.42, 107.23, 113.64, 118.34, 121.57, 125.64, 126.57, 127.60, 128.82, 132.58, 133.42, 133.83, 133.06, 134.38, 137.67, 148.00, 148.96, 157.66, 159.37, 182.90, 184.99.

EXAMPLE 31

2-((4-(pyrimidin-2-yl)piperazin-1-yl)methyl)-1H-anthra[1,2-d]imidazole-6,11-dione (CL29)

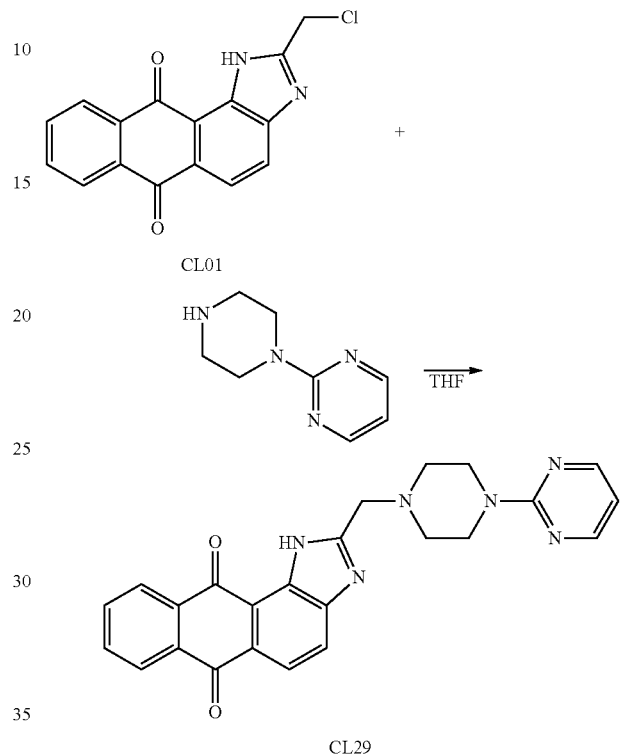

Compound CL01 (1.18 g, 4 mmole) and DIPEA (1.4 mL, 8 mmole) were stirred in 30 mL anhydrous tetrahydrofuran (THF) for 10 minutes. Then, 1-(2-pyrimidyl)piperazine (1.13 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 424.4546 ($C_{24}H_{20}N_6O_2$); Yield: 59%; Mp: 223-224° C.; $R_f$: 0.21 (ethyl acetate:dichloromethane=1:1); HRMS (EI) m/z calcd for $C_{24}H_{20}N_6O_2^+$[M]$^+$: 424.1648. Found: 424.1652. $^1$H-NMR (300 MHz, $CDCl_3$) δ (ppm): 2.70 (t, J=5.0 Hz, 4H, N—$CH_2$—), 3.95 (t, J=5.0 Hz, 4H, N—$CH_2$—), 3.99 (s, 2H, —$CH_2$—), 6.51 (t, J=4.8 Hz, 1H, Ar'—H), 7.79-7.82 (m, 2H, Ar—$H_{8,9}$), 8.06 (d, J=8.4 Hz, 1H, Ar—$H_4$), 8.22 (d, J=8.7 Hz, 1H, Ar—$H_5$), 8.26-8.35 (m, 4H, Ar—$H_{7,10}$, Ar'—H); $^{13}$C-NMR (75 MHz, $CDCl_3$) δ (ppm): 43.58, 53.48, 56.56, 110.18, 118.34, 121.60, 125.67, 126.59, 127.65, 128.82, 132.61, 133.44, 133.87, 134.07, 134.43, 148.97, 157.85, 161.82, 182.96, 185.10.

EXAMPLE 32

2-((4-(2-fluorophenyl)piperazin-1-yl)methyl)-1H-anthra[1,2-d]imidazole-6,11-dione (CL30)

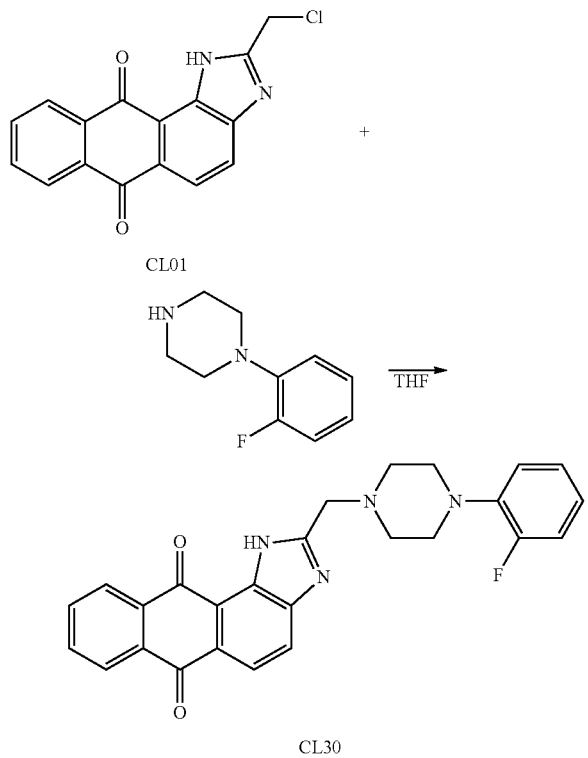

EXAMPLE 33

2-((4-(2-cyanophenyl)piperazin-1-yl)methyl)-1H-anthra[1,2-d]imidazole-6,11-dione (CL31)

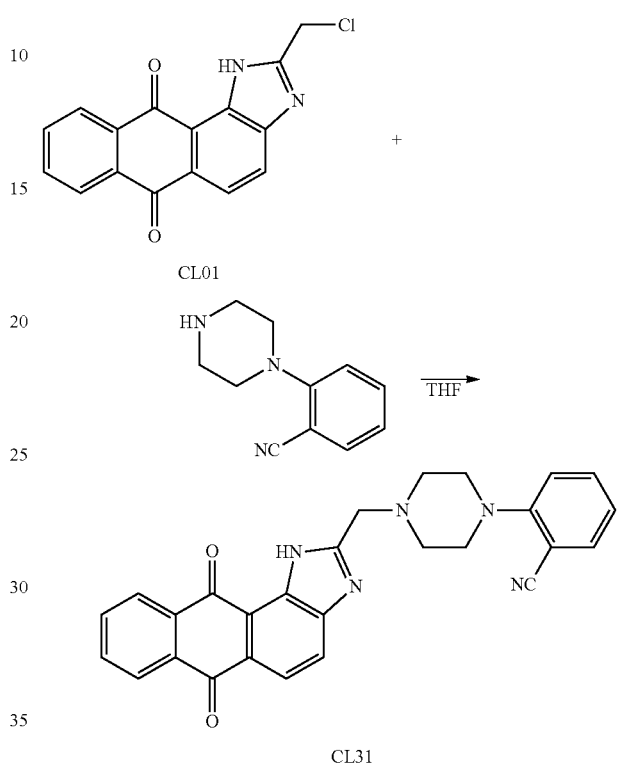

Compound CL01 (1.18 g, 4 mmole) and DIPEA (1.4 mL, 8 mmole) were stirred in 30 mL anhydrous tetrahydrofuran (THF) for 10 minutes. Then, 1-(2-fluorophenyl)piperazine (1.26 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 440.4689 ($C_{26}H_{21}FN_4O_2$); Yield: 67%; Mp: 163-164° C.; $R_f$: 0.46 (ethyl acetate:dichloromethane=1:1); HRMS (EI) m/z calcd for $C_{26}H_{21}FN_4O_2^+[M]^+$: 424.1649. Found: 440.1643. $^1$H-NMR (300 MHz, $CDCl_3$) δ (ppm): 2.89 (t, J=4.4 Hz, 4H, N—$CH_2$—), 3.25 (t, J=4.7 Hz, 4H, N—$CH_2$—), 4.08 (s, 2H, —$CH_2$—), 6.94-7.07 (m, 4H, Ar'—H), 7.77-7.80 (m, 2H, Ar—$H_{8,9}$), 8.03 (d, J=8.4 Hz, 1H, Ar—$H_4$), 8.18 (d, J=8.4 Hz, 1H, Ar—$H_5$), 8.23-8.33 (m, 4H, Ar—$H_{7,10}$, Ar'—H); $^{13}$C-NMR (75 MHz, $CDCl_3$) δ (ppm): 50.17, 53.61, 56.23, 116.13, 116.40, 118.39, 119.21, 119.25, 121.59, 122.82, 122.92, 124.55, 124.60, 125.67, 126.59, 127.61, 128.85, 132.58, 133.41, 133.84, 134.03, 134.39, 148.90, 154.29, 157.56, 182.91, 184.96.

Compound CL01 (1.18 g, 4 mmole) and DIPEA (1.4 mL, 8 mmole) were stirred in 30 mL anhydrous tetrahydrofuran (THF) for 10 minutes. Then, 1-(2-cyanophenyl)piperazine (1.35 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 447.4879 ($C_{27}H_{21}N_5O_2$); Yield: 45%; Mp: 230-231° C.; $R_f$: 0.41 (ethyl acetate:dichloromethane=1:1); HRMS (EI) m/z calcd for $C_{27}H_{21}N_5O_2^+[M]^+$: 447.1695. Found: 447.1712. $^1$H-NMR (300 MHz, $CDCl_3$) δ (ppm): 2.94 (t, J=4.2 Hz, 4H, N—$CH_2$—), 3.37 (t, J=4.7 Hz, 4H, N—$CH_2$—), 4.10 (s, 2H, —$CH_2$—), 7.47-7.59 (m, 2H, Ar'—H), 7.77-7.80 (m, 2H, Ar—$H_{8,9}$), 8.02 (d, J=8.4 Hz, 1H, Ar—$H_4$), 8.18 (d, J=8.4 Hz, 1H, Ar—$H_5$), 8.22-8.32 (m, 4H, Ar—$H_{7,10}$, Ar'—H); $^{13}$C-NMR (75 MHz, $CDCl_3$) δ (ppm): 51.15, 53.53, 56.09, 106.59, 118.22, 118.48, 119.03, 121.67, 122.37, 125.81, 126.63, 127.67, 129.00, 132.65, 133.48, 133.87, 133.91, 134.12, 134.43, 134.47, 148.94, 155.35, 182.93, 185.03.

EXAMPLE 34

2-((4-(3-methoxyphenyl)piperazin-1-yl)methyl)-1H-anthra[1,2-d]imidazole-6,11-dione (CL32)

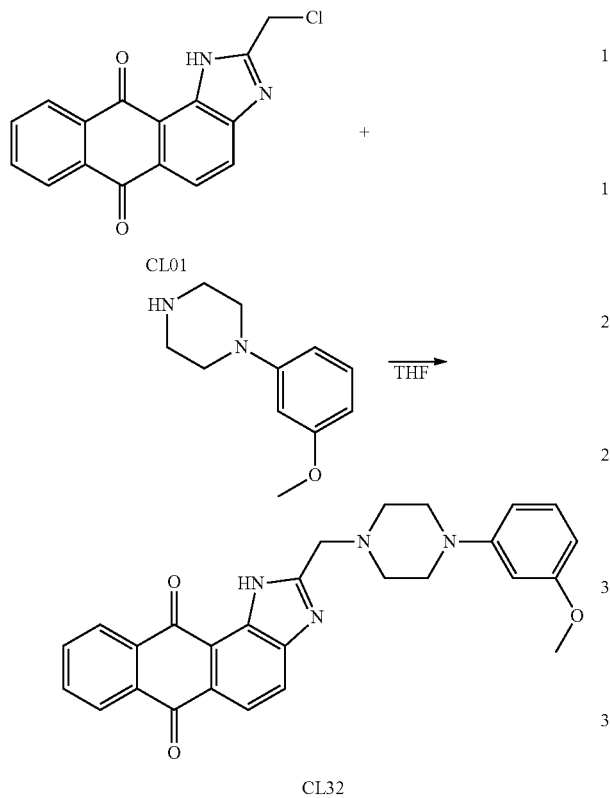

EXAMPLE 35

2-((4-benzylpiperazin-1-yl)methyl)-1H-anthra[1,2-d]imidazole-6,11-dione (CL33)

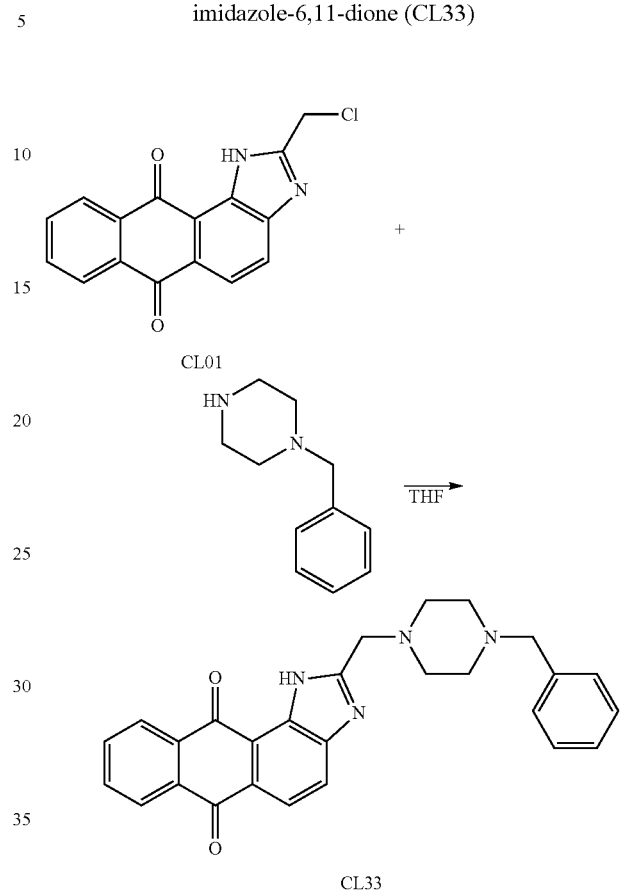

Compound CL01 (1.18 g, 4 mmole) and DIPEA (1.4 mL, 8 mmole) were stirred in 30 mL anhydrous tetrahydrofuran (THF) for 10 minutes. Then, 1-(3-methoxyphenyl)piperazine (1.38 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 452.5045 ($C_{22}H_{24}N_4O_3$); Yield: 58%; Mp: 150-151° C.; $R_f$: 0.42 (ethyl acetate:dichloromethane=1:1); HRMS (EI) m/z calcd for $C_{22}H_{24}N_4O_3^+[M]^+$: 442.1848. Found: 452.1846. $^1$H-NMR (300 MHz, $CDCl_3$) δ (ppm): 2.89 (s, 4H, N—$CH_2$—), 3.35 (t, J=4.8 Hz, 4H, N—$CH_2$—), 3.79 (s, 3H, O—$CH_3$), 4.13 (s, 2H, —$CH_2$—), 6.43-6.56 (m, 3H, Ar'—H), 7.18 (t, J=8.1 Hz, 1H, Ar'—H), 7.77-7.80 (m, 2H, Ar—$H_{8,9}$), 8.02 (d, J=8.1 Hz, 1H, Ar—$H_4$), 8.19 (d, J=8.4 Hz, 1H, Ar—$H_5$), 8.23-8.33 (m, 4H, Ar—$H_{7,10}$, Ar'—H); $^{13}$C-NMR (75 MHz, $CDCl_3$) δ (ppm): 48.80, 53.36, 55.18, 56.09, 103.06, 105.21, 109.23, 118.51, 121.63, 125.68, 126.67, 127.61, 128.97, 129.99, 132.63, 133.42, 133.88, 134.03, 134.39, 148.80, 152.35, 160.88, 182.94, 184.86.

Compound CL01 (1.18 g, 4 mmole) and DIPEA (1.4 mL, 8 mmole) were stirred in 30 mL anhydrous tetrahydrofuran (THF) for 10 minutes. Then, 1-benzylpiperazine (1.39 mL, 8 mmole) was added thereto. The mixed solution was reacted by heating under reflux for 6 hours. After completion of reaction, the mixed solution was concentrated under reduced pressure (by reduced pressure concentrator such as Vacuum Evaporator). Then the concentrated mixture was extracted with ethyl acetate/$H_2O$. The extract was dried by $MgSO_4$ and concentrated under reduced pressure to obtain a crude product. The crude product was recrystallized in ethyl acetate/n-hexane, the mixture was filtered to collect the crystal which was rinsed with acetone to obtain a yellowish brown compound.

Mol. Wt.: 436.5051 ($C_{27}H_{24}N_4O_2$); Yield: 62%; Mp: 194-195° C.; $R_f$: 0.81 (ethyl acetate:dichloromethane:methanol=2:2:1); HRMS (EI) m/z calcd for $C_{27}H_{24}N_4O_2^+[M]^+$: 436.1899. Found: 436.1902. $^1$H-NMR (300 MHz, $CDCl_3$) δ (ppm): 2.64-2.69 (m, 8H, N—$CH_2$—), 3.60 (s, 2H, —$CH_2$—), 3.92 (s, 2H, —$CH_2$—), 7.27-7.36 (m, 5H, Ar'—H), 7.76-7.80 (m, 2H, Ar—$H_{8,9}$), 8.00 (d, J=8.1 Hz, 1H, Ar—$H_4$), 8.16 (d, J=8.4 Hz, 1H, Ar—$H_5$), 8.22-8.31 (m, 4H, Ar—$H_{7,10}$, Ar'—H); $^{13}$C-NMR (75 MHz, $CDCl_3$) δ (ppm): 52.84, 53.50, 56.32, 62.81, 118.17, 121.48, 125.55, 126.49, 127.27, 127.57, 128.34, 128.61, 129.26, 132.46, 133.36, 133.78, 134.00, 134.35, 137.78, 148.98, 158.34, 182.87, 185.00.

EXAMPLE 36

1,2-bis(3-chloropropionamido)anthraquinone (CL34)

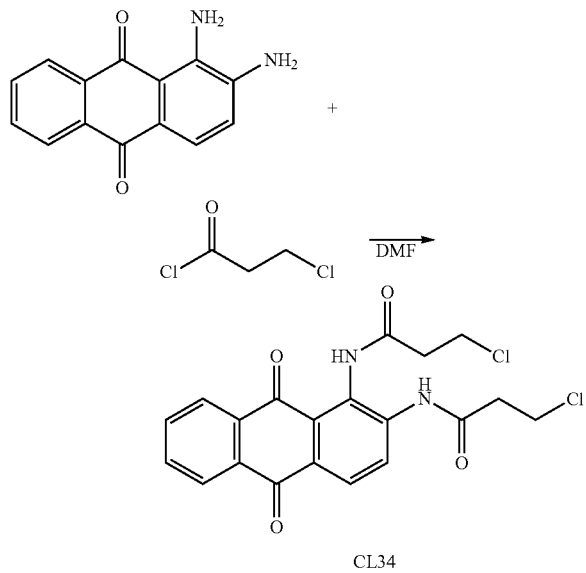

CL34

Compound 1,2-diaminoanthraquinone (0.95 g, 4 mmole) was dissolved in 30 mL anhydrous N,N-dimethylformamide. Nitrogen gas was filled into the reaction flask at room temperature. To the reaction solution, triethylamine (1.2 mL, 8 mmole) and 3-chloropropionyl chloride (1.2 mL, 12 mmole) were added successively. The mixture was stirred at room temperature for 24 hours. After completion of reaction, the mixed solution was poured into an ice-water bath (200 mL) and stood still for 10 to 20 minutes. Precipitation occurred at this time. The mixture was filtered to collect precipitate which was rinsed with ethanol to obtain a yellowish brown compound.

Mol. Wt.: 419.2580 ($C_{20}H_{16}Cl_2N_2O_4$); $R_f$: 0.23 (ethyl acetate:n-hexane=1:2); Yield: 51%; mp: 179-180° C.; HRMS (EI) m/z: calcd for $C_{20}H_{16}Cl_2N_2O_4{}^+[M]^+$ 418.0487. Found: 418.0494. $^1$H-NMR (300 MHz, DMSO-$d_6$) δ (ppm): 2.94-3.03 (m, 4H, —$CH_2$—), 3.86-3.94 (m, 4H, —$CH_2Cl$), 7.88-7.90 (m, 2H, Ar—H), 8.10-8.15 (m, 2H, Ar—H), 8.08 (d, J=8.1 Hz, 1H, Ar—H), 8.42 (d, J=8.7 Hz, 1H, Ar—H), 9.50 (s, 1H, Ar—NH—), 10.02 (s, 1H, Ar—NH—); $^{13}$C-NMR (75 MHz, DMSO-$d_6$) δ (ppm): 40.20, 40.26, 125.94, 126.29, 126.87, 127.61, 127.79, 128.33, 129.79, 132.27, 134.26, 134.36, 134.52, 140.28, 168.86, 169.43, 181.63, 183.22.

EXAMPLE 37

2-(2-chloroethyl)-1H-anthra[1,2-d]imidazole-6,11-dione (CL35)

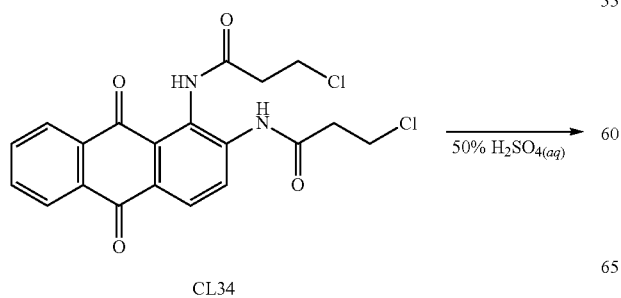

CL34

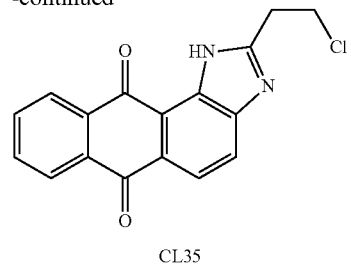

CL35

Compound CL34 (2.10 g, 5 mmole) was dissolved in 50% sulfuric acid (10 mL) at 0° C. The solution was reaction by stirring within a sealed mini-reactor apparatus. The apparatus was placed in an oil bath at a temperature of about 110° C. for 2 hours. After completion of reaction, the mixed solution was extracted several times with dichloromethane/$H_2O$. The combined extract was dried on $MgSO_4$ and concentrated under reduced pressure to obtain a crude product which was rinsed with acetone to obtain a brown compound.

Mol. Wt.: 310.7344 ($C_{12}H_{11}ClN_2O_2$); Yield: 68%; Mp: 261-262° C.; $R_f$: 0.51 (ethyl acetate:dichloromethane=1:1); HRMS (EI) m/z calcd for $C_{17}H_{11}ClN_2O_2{}^+[M]^+$: 310.0509. Found: 310.0511. $^1$H-NMR (300 MHz, CDCl$_3$) δ (ppm): 3.54 (t, J=6.5 Hz, 2H, —$CH_2$—), 4.07 (t, J=6.5 Hz, 2H, —$CH_2Cl$), 7.80-7.82 (m, 2H, Ar—$H_{8,9}$), 8.08 (d, J=8.4 Hz, 1H, Ar—$H_4$), 8.23 (d, J=8.4 Hz, 1H, Ar—$H_5$), 8.35-8.25 (m, 2H, Ar—$H_{7,10}$); $^{13}$C-NMR (75 MHz, DMSO-$d_6$) δ (ppm): 28.54, 28.86, 122.56, 126.32, 126.92, 129.01, 132.82, 132.99, 134.48, 134.77, 182.08, 183.07.

EXAMPLE 38

2-(2-(4-methylpiperazin-1-yl)ethyl)-1H-anthra[1,2-d]imidazole-6,11-dione (CL36)

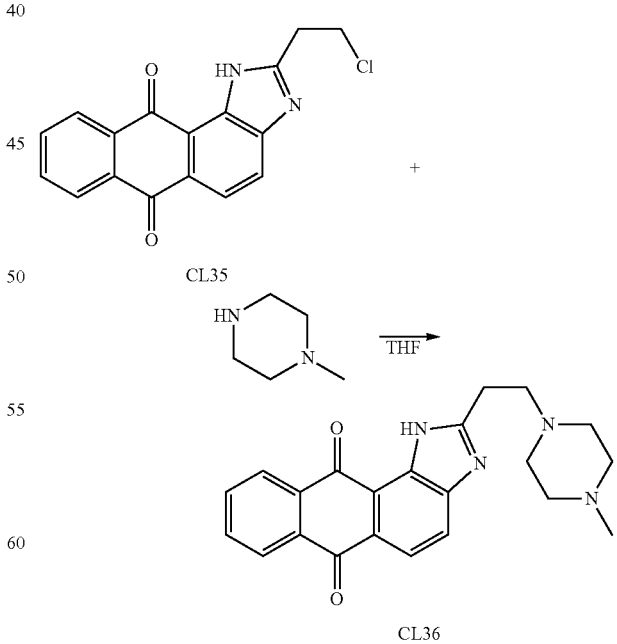

CL36

Compound CL35 (1.24 g, 4 mmole) and DIPEA (1.4 mL, 8 mmole) were stirred in 30 mL anhydrous THF for 10 minutes, and then, N-methylpiperazine (0.88 mL, 8 mmole) was added thereto. The mixed solution was reacted by heating under reflux for 6 hours. After completion of reaction, the mixed solution was concentrated under reduced pressure. The concentrated mixture was extracted with ethyl acetate/H$_2$O. The extract was dried on MgSO$_4$ and then concentrated under reduced pressure to obtain a crude product. The crude product was recrystallized in ethyl acetate/n-hexane. The mixture was filtered to collect the crystal which was rinsed with acetone to obtain a yellowish brown compound.

Mol. Wt.: 374.7344 (C$_{22}$H$_{22}$N$_4$O$_2$); Yield: 71%; Mp: 190-191° C.; R$_f$: 0.15 (ethyl acetate:dichloromethane:methanol=2:2:1); HRMS (EI) m/z calcd for C$_{22}$H$_{22}$N$_4$O$_2{}^+$[M]$^+$: 374.1743. Found: 374.1740. $^1$H-NMR (300 MHz, CDCl$_3$) δ (ppm): 2.54 (s, 3H, N—CH$_3$), 2.70 (s, 4H, N—CH$_2$—), 2.89 (s, 4H, N—CH$_2$—), 2.93 (t, J=6.0 Hz, 2H, —CH$_2$—), 3.20 (t, J=5.7 Hz, 2H, —CH$_2$—), 7.75-7.78 (m, 2H, Ar—H$_{8,9}$), 7.96 (d, J=8.4 Hz, 1H, —CH$_4$), 8.15 (d, J=8.1 Hz, 1H, Ar—H$_5$), 8.16-8.31 (m, 2H, Ar—H$_{7,10}$); $^{13}$C-NMR (75 MHz, CDCl$_3$) δ (ppm): 25.26, 45.79, 52.43, 54.74, 54.90, 118.17, 121.31, 124.91, 126.57, 127.49, 128.23, 132.35, 133.62, 134.13, 148.78, 160.55, 183.19, 184.48.

EXAMPLE 39

2-(2-(4-phenylpiperazin-1-yl)ethyl)-1H-anthra[1,2-d]imidazole-6,11-dione (CL37)

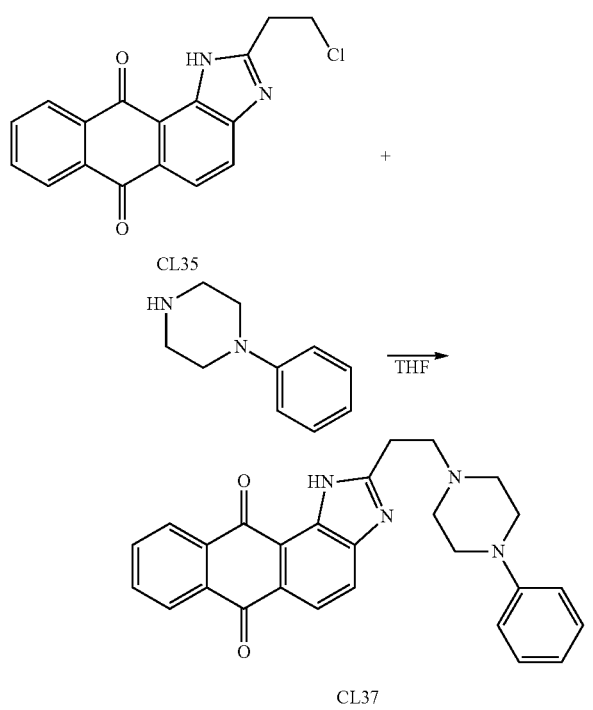

Compound CL35 (1.24 g, 4 mmole) and DIPEA (1.4 mL, 8 mmole) were stirred in 30 mL anhydrous THF for 10 minutes, and then, N-phenylpiperazine (1.22 mL, 8 mmole) was added thereto. The mixed solution was reacted by heating under reflux for 6 hours. After completion of reaction, the mixed solution was concentrated under reduced pressure. The concentrated mixture was extracted with ethyl acetate/H$_2$O. The extract was dried on MgSO$_4$ and then concentrated under reduced pressure to obtain a crude product. The crude product was recrystallized in ethyl acetate/n-hexane. The mixture was filtered to collect the crystal which was rinsed with acetone to obtain a yellowish brown compound.

Mol. Wt.: 436.5051 (C$_{27}$H$_{24}$N$_4$O$_2$); Yield: 67%; Mp: 211-212° C.; R$_f$: 0.52 (ethyl acetate:dichloromethane=1:1); HRMS (EI) m/z calcd for C$_{27}$H$_{24}$N$_4$O$_2{}^+$[M]$^+$: 436.1899. Found: 436.1896. $^1$H-NMR (300 MHz, CDCl$_3$) δ (ppm): 2.95 (s, 4H, N—CH$_2$—), 3.09 (s, 2H, —CH$_2$—), 3.33 (t, J=5.6 Hz, 2H, —CH$_2$—), 3.56 (t, J=4.8 Hz, 4H, N—CH$_2$—), 6.93 (t, J=7.4 Hz, 1H, Ar'—H), 7.05 (d, J=7.8 Hz, 2H, Ar'—H), 7.31-7.37 (m, 2H, Ar'—H), 7.73-7.77 (m, 2H, Ar—H$_{8,9}$), 7.93 (d, J=8.4 Hz, 1H, Ar—H$_4$), 8.14 (d, J=8.4 Hz, 1H, Ar—H$_5$), 8.18-8.31 (m, 2H, Ar—H$_{7,10}$); $^{13}$C-NMR (75 MHz, CDCl$_3$) δ (ppm): 25.34, 49.22, 52.93, 55.07, 116.47, 117.39, 118.25, 120.02, 121.34, 124.89, 126.75, 127.43, 128.30, 129.30, 129.49, 132.39, 133.57, 133.65, 134.11, 148.77, 151.36, 183.19, 184.50.

EXAMPLE 40

2-(2-(4-(pyridin-2-yl)piperazin-1-yl)ethyl)-1H-anthra[1,2-d]imidazole-6,11-dione (CL38)

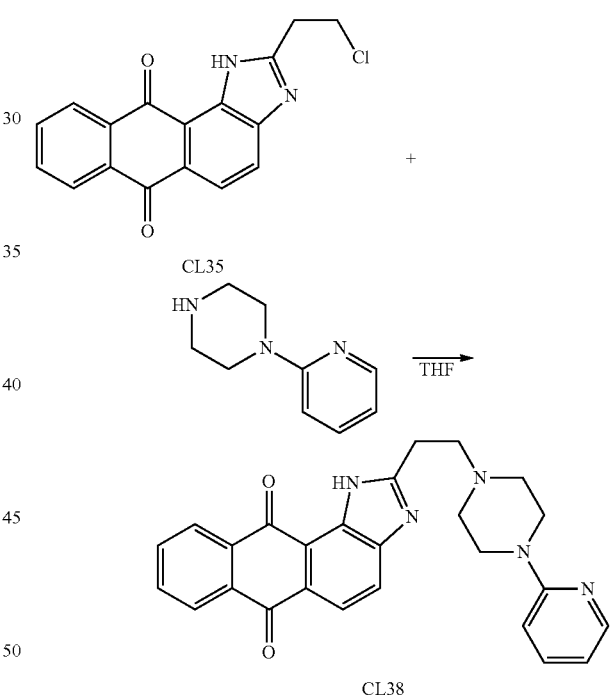

Compound CL35 (1.24 g, 4 mmole) and DIPEA (1.4 mL, 8 mmole) were stirred in 30 mL anhydrous THF for 10 minutes, and then, 1-(2-pyridyl)piperazine (1.21 mL, 8 mmole) was added thereto. The mixed solution was reacted by heating under reflux for 6 hours. After completion of reaction, the mixed solution was concentrated under reduced pressure. The concentrated mixture was extracted with ethyl acetate/H$_2$O. The extract was dried on MgSO$_4$ and then concentrated under reduced pressure to obtain a crude product. The crude product was recrystallized in ethyl acetate/n-hexane. The mixture was filtered to collect the crystal which was rinsed with acetone to obtain a yellowish brown compound.

Mol. Wt.: 437.4931 (C$_{26}$H$_{23}$N$_5$O$_2$); Yield: 65%; Mp: 234-235° C.; R$_f$: 0.42 (ethyl acetate:dichloromethane=1:1);

HRMS (EI) m/z calcd for $C_{26}H_{23}N_5O_2{}^+[M]^+$: 437.1852. Found: 437.1856. $^1$H-NMR (300 MHz, CDCl$_3$) δ (ppm): 2.87 (s, 4H, N—CH$_2$—), 3.02 (t, J=5.3 Hz, 2H, —CH$_2$—), 3.31 (t, J=5.9 Hz, 2H, —CH$_2$—), 3.93 (s, 4H, N—CH$_2$—), 6.69 (t, J=6 Hz, 1H, Ar'—H), 6.76 (d, J=8.4 Hz, 1H, Ar'—H), 7.53-7.58 (m, 1H, Ar'—H), 7.73-7.77 (m, 2H, Ar—H$_{8,9}$), 7.99 (d, J=8.4 Hz, 1H, Ar—H$_4$), 8.17 (d, J=8.4 Hz, 1H, Ar—H$_5$), 8.22-8.32 (m, 3H, Ar'—H, Ar—H$_{7,10}$); $^{13}$C-NMR (75 MHz, CDCl$_3$) δ (ppm): 25.21, 45.05, 52.68, 55.10, 107.28, 113.63, 118.26, 121.37, 124.92, 126.76, 127.46, 128.32, 132.39, 133.54, 133.68, 134.07, 134.14, 137.80, 148.08, 148.72, 159.32, 183.20, 184.51.

EXAMPLE 41

2-(2-(4-(pyrimidin-2-yl)piperazin-1-yl)ethyl)-1H-anthra[1,2-d]imidazole-6,11-dione (CL39)

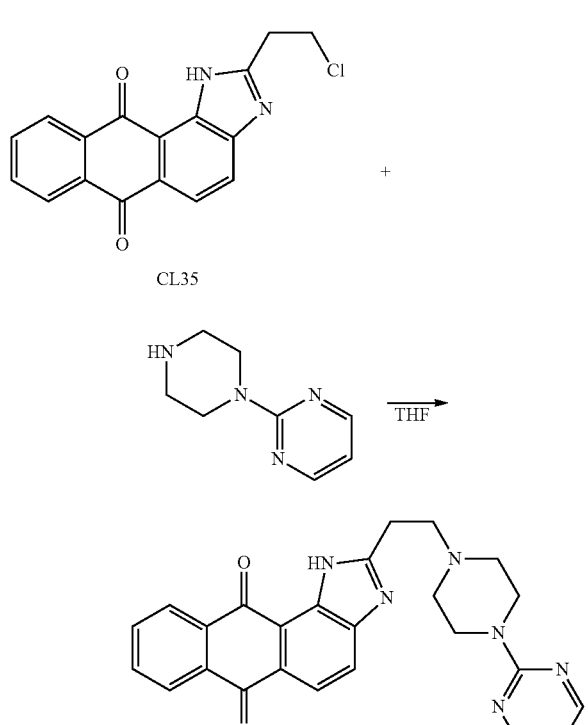

Compound CL35 (1.24 g, 4 mmole) and DIPEA (1.4 mL, 8 mmole) were stirred in 30 mL anhydrous THF for 10 minutes, and then, 1-(2-pyrimidyl)piperazine (1.13 mL, 8 mmole) was added thereto. The mixed solution was reacted by heating under reflux for 6 hours. After completion of reaction, the mixed solution was concentrated under reduced pressure. The concentrated mixture was extracted with ethyl acetate/H$_2$O. The extract was dried on MgSO$_4$ and then concentrated under reduced pressure to obtain a crude product. The crude product was recrystallized in ethyl acetate/n-hexane. The mixture was filtered to collect the crystal which was rinsed with acetone to obtain a yellowish brown compound.

Mol. Wt.: 438.4812 ($C_{25}H_{22}N_6O_2$); Yield: 61%; Mp: 230-231° C.; $R_f$: 0.44 (ethyl acetate:dichloromethane=1:1); HRMS (EI) m/z calcd for $C_{25}H_{22}N_6O_2{}^+[M]^+$: 438.1804. Found: 438.1806. $^1$H-NMR (300 MHz, CDCl$_3$) δ (ppm): 2.81 (s, 4H, N—CH$_2$—), 3.01 (t, J=5.6 Hz, 2H, —CH$_2$—), 3.30 (t, J=5.6 Hz, 2H, —CH$_2$—), 4.20 (s, 4H, N—CH$_2$—), 6.54 (t, J=4.7 Hz, 1H, Ar'—H), 7.73-7.76 (m, 2H, Ar—H$_{8,9}$), 7.97 (d, J=8.4 Hz, 1H, Ar—H$_4$), 8.16 (d, J=8.4 Hz, 1H, Ar—H$_5$), 8.22-8.31 (m, 2H, Ar—H$_{7,10}$), 8.36 (d, J=4.8 Hz, 2H, Ar'—H); $^{13}$C-NMR (75 MHz, CDCl$_3$) δ (ppm): 25.20, 43.57, 52.77, 55.10, 110.15, 118.22, 121.34, 124.89, 126.72, 127.45, 128.27, 132.35, 133.55, 133.66, 134.06, 134.13, 148.71, 157.93, 160.27, 161.81, 183.19, 184.51.

EXAMPLE 42

2-(2-(4-benzylpiperazin-1-yl)ethyl)-1H-anthra[1,2-d]imidazole-6,11-dione (CL40)

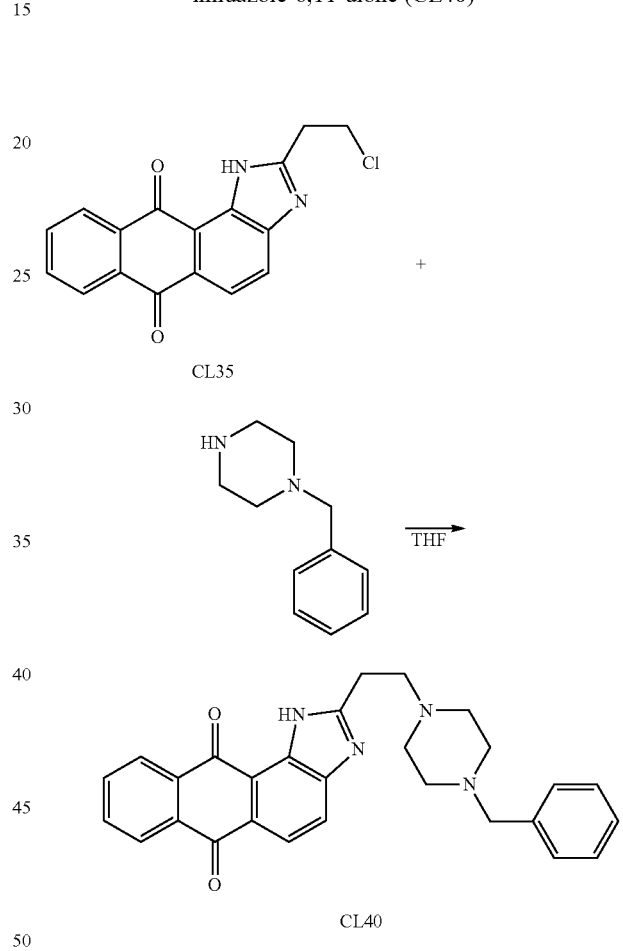

Compound CL35 (1.24 g, 4 mmole) and DIPEA (1.4 mL, 8 mmole) were stirred in 30 mL anhydrous THF for 10 minutes, and then, 1-benzylpiperazine (1.39 mL, 8 mmole) was added thereto. The mixed solution was reacted by heating under reflux for 6 hours. After completion of reaction, the mixed solution was concentrated under reduced pressure. The concentrated mixture was extracted with ethyl acetate/H$_2$O. The extract was dried on MgSO$_4$ and then concentrated under reduced pressure to obtain a crude product. The crude product was recrystallized in ethyl acetate/n-hexane. The mixture was filtered to collect the crystal which was rinsed with acetone to obtain a yellowish brown compound.

Mol. Wt.: 450.5316 ($C_{28}H_{26}N_4O_2$); Yield: 51%; Mp: 177-178° C.; $R_f$: 0.19 (ethyl acetate:dichloromethane=1:1); HRMS (EI) m/z calcd for $C_{28}H_{26}N_4O_2{}^+[M]^+$: 450.2056. Found: 450.2050. $^1$H-NMR (300 MHz, CDCl$_3$) δ (ppm): 2.74

(s, 4H, N—CH$_2$—), 2.83 (s, 4H, N—CH$_2$—), 2.90 (t, J=6.0 Hz, 2H, —CH$_2$—), 3.19 (t, J=6.0 Hz, 2H, —CH$_2$—), 3.71 (s, 2H, —CH$_2$—), 7.28-7.44 (m, 5H, Ar'—H), 7.77-7.80 (m, 2H, Ar—H$_{8,9}$), 7.96 (d, J=8.4 Hz, 1H, Ar—H$_4$), 8.15 (d, J=8.4 Hz, 1H, Ar—H$_5$), 8.28-8.32 (m, 2H, Ar—H$_{7,10}$); $^{13}$C-NMR (75 MHz, CDCl$_3$) δ (ppm): 25.22, 52.21, 52.61, 54.71, 62.68, 118.19, 121.32, 124.91, 126.59, 127.50, 127.68, 128.26, 128.55, 129.09, 129.66, 132.36, 133.58, 133.63, 134.11, 134.16, 148.75, 160.29, 183.16, 184.48.

EXAMPLE 43

Figure 3A:
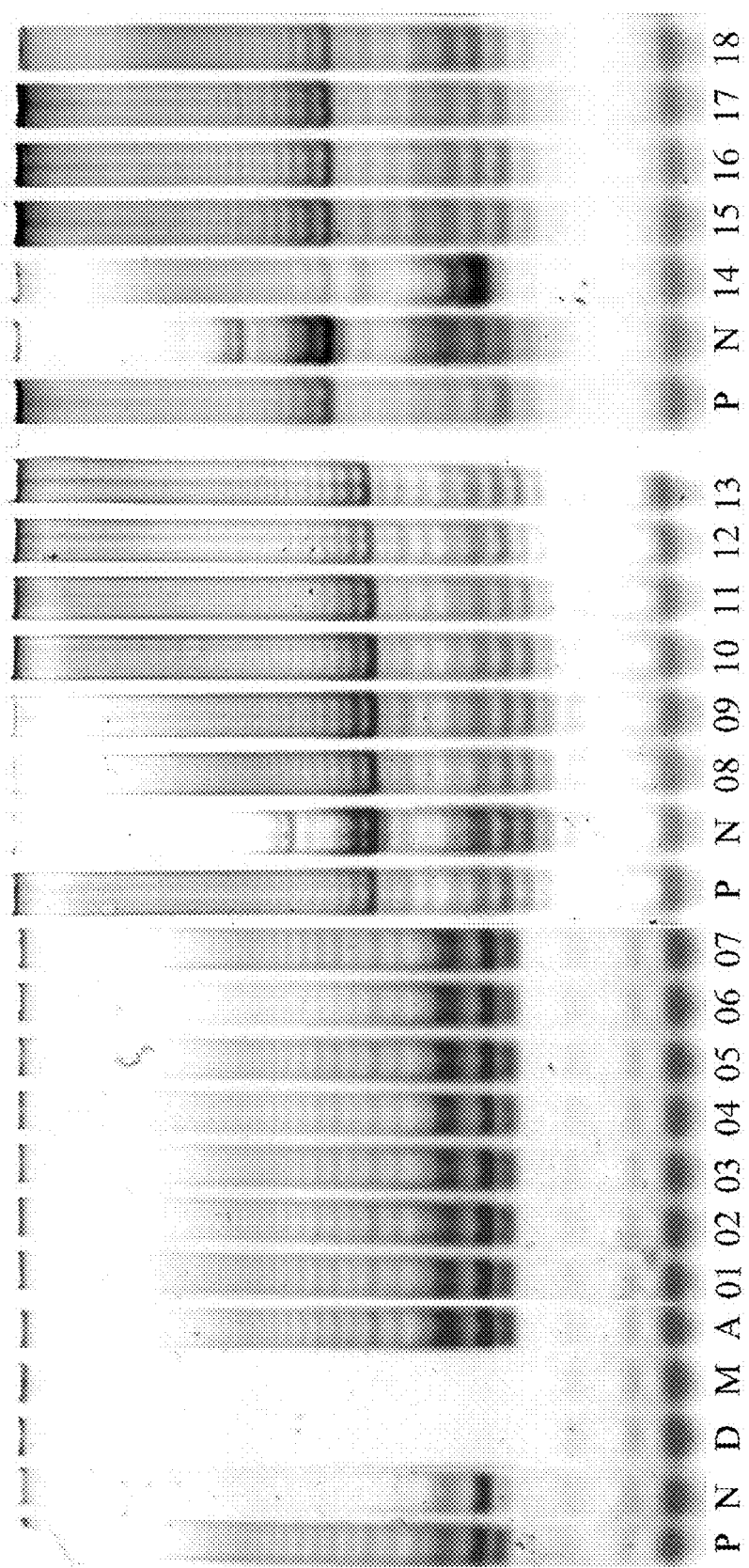
FIG. 3A depicts the result of the compound CL01 to CL18 in TRAP assay.
Figure 3B:
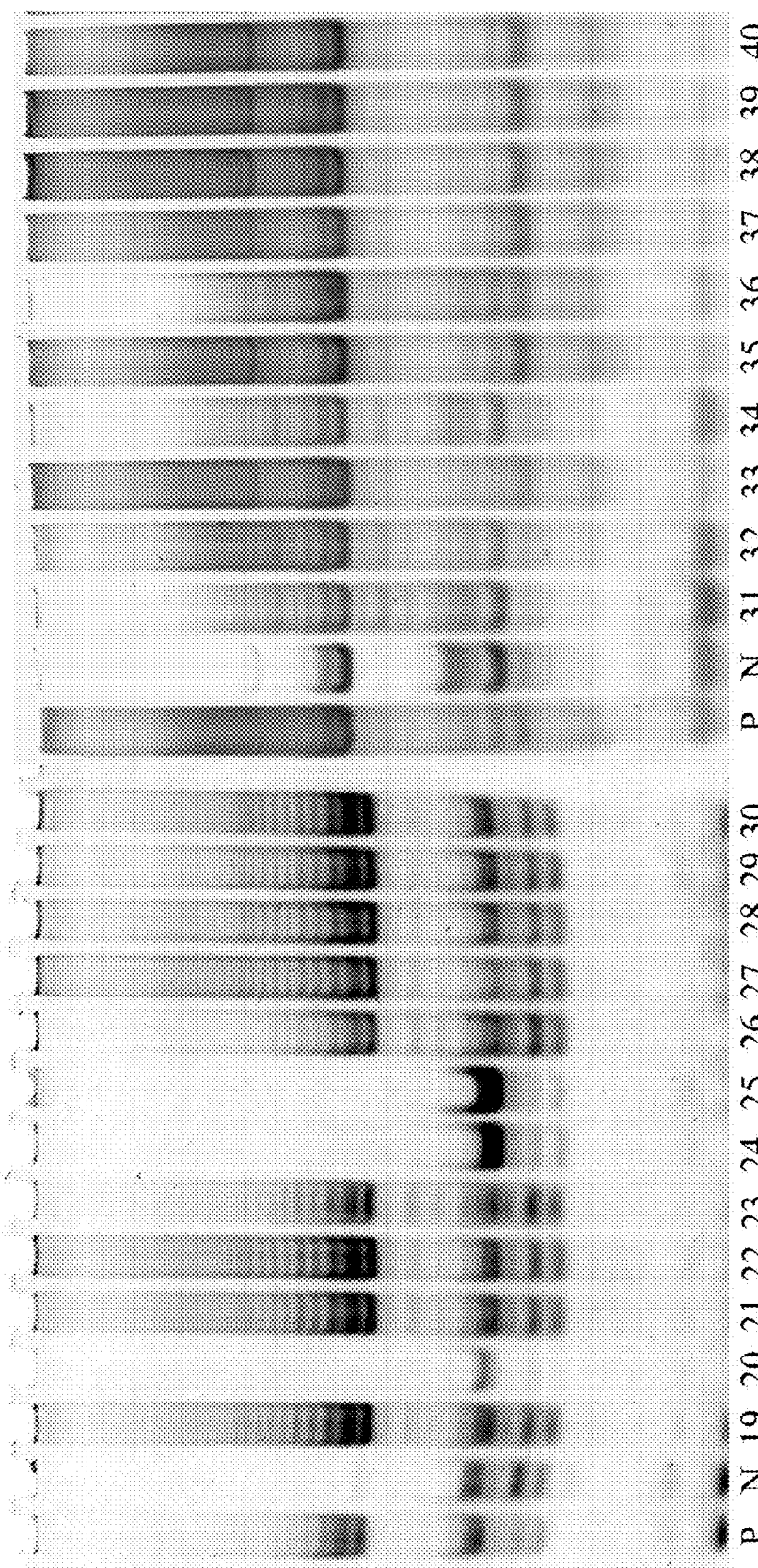
FIG. 3B depicts the result of the compound CL19 to CL40 in TRAP assay. P represents positive control, N represents negative control, D represents doxorubicin, M represents mitoxantrone, A represents 1,2-diaminoanthrquione.
Figure 4:
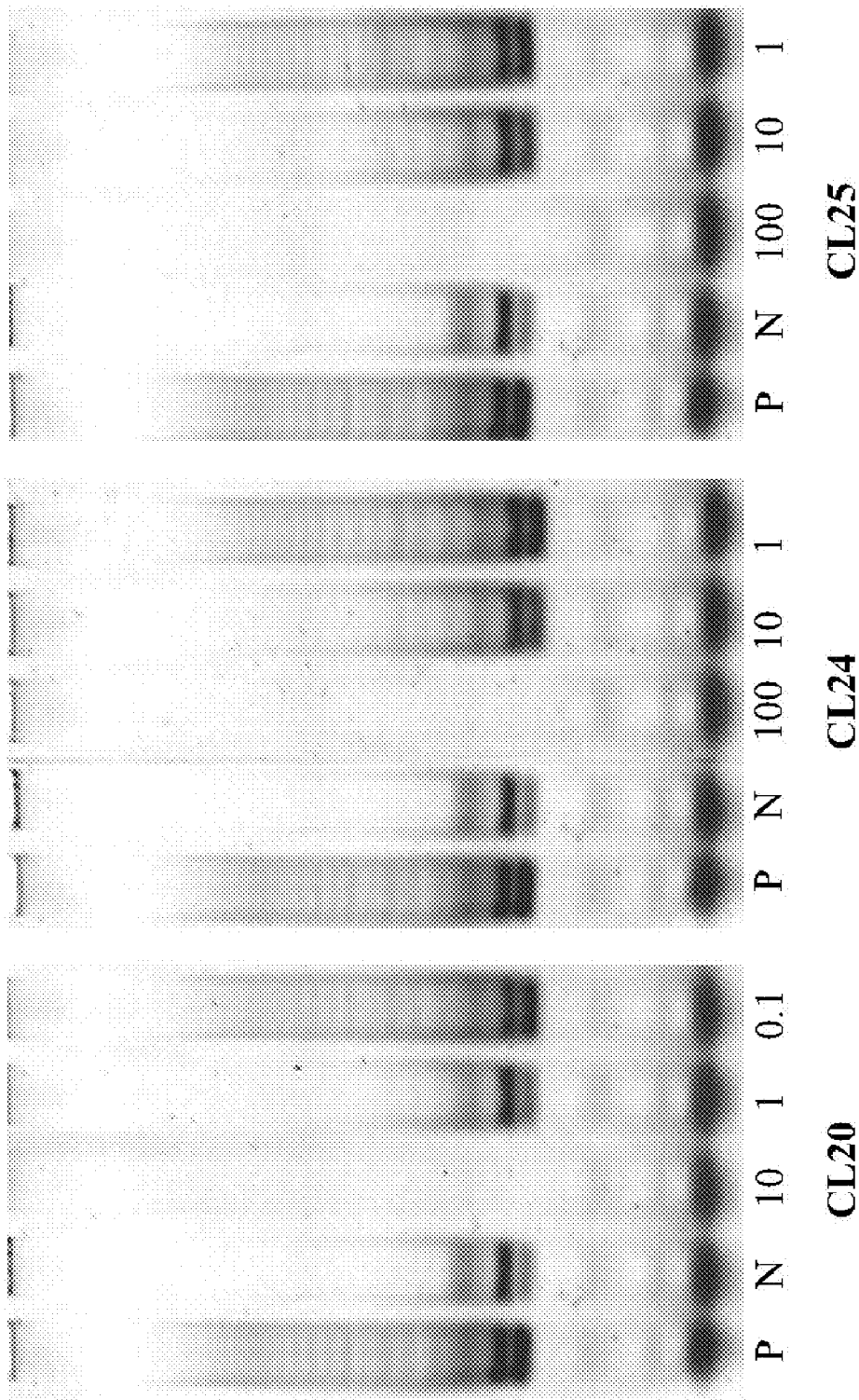
FIG. 4 depicts the result of the compound CL20, CL24 and CL25 in TRAP assay under different dosage (X axis: concentration, μM); P represents positive control, N represents negative control.
Figure 5:
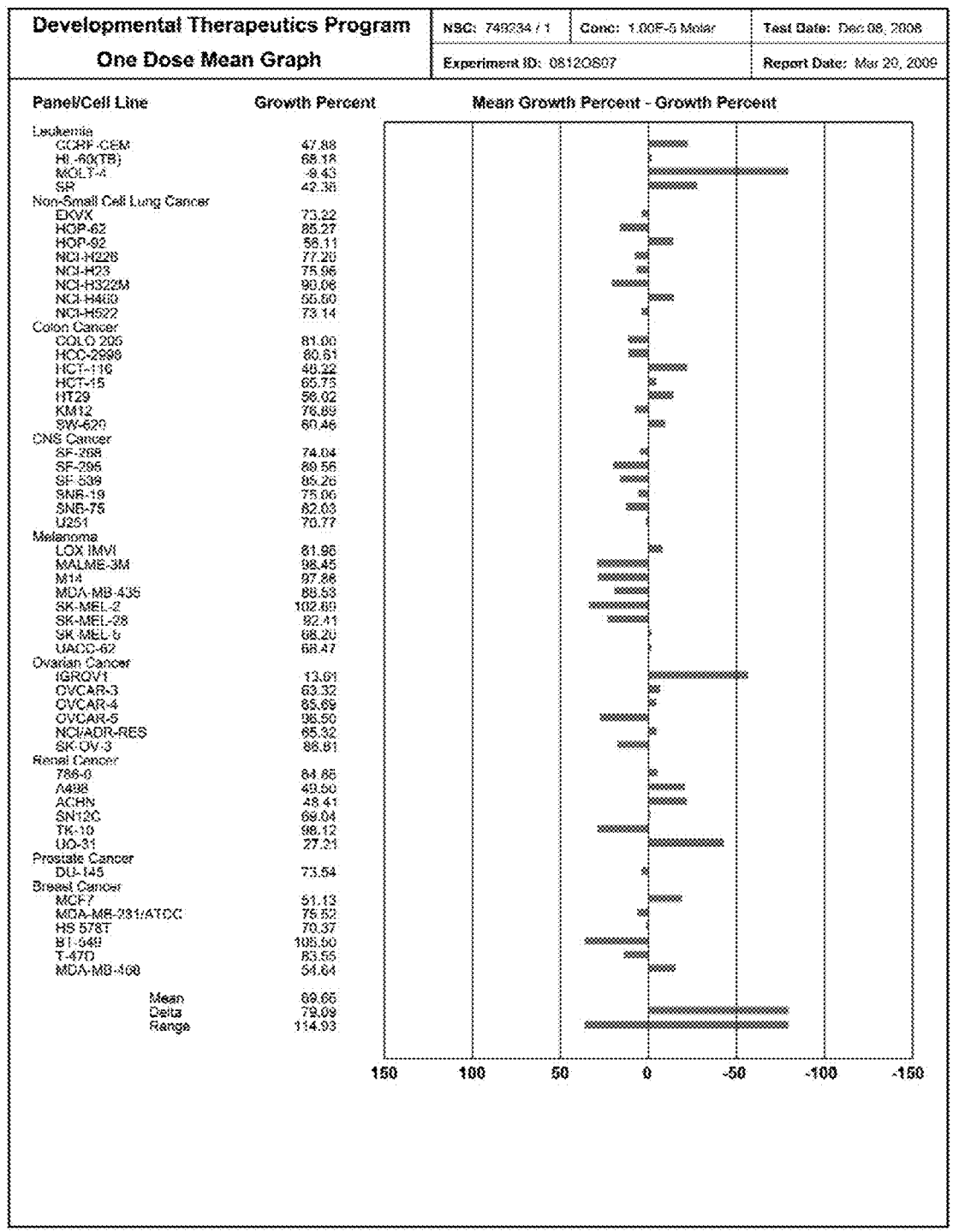
FIG. 5 to FIG. 10 depict the NCI result of compounds CL-04, CL-07, CL-16, CL-24, CL-27 and CL-28, respectively.
Figure 6:
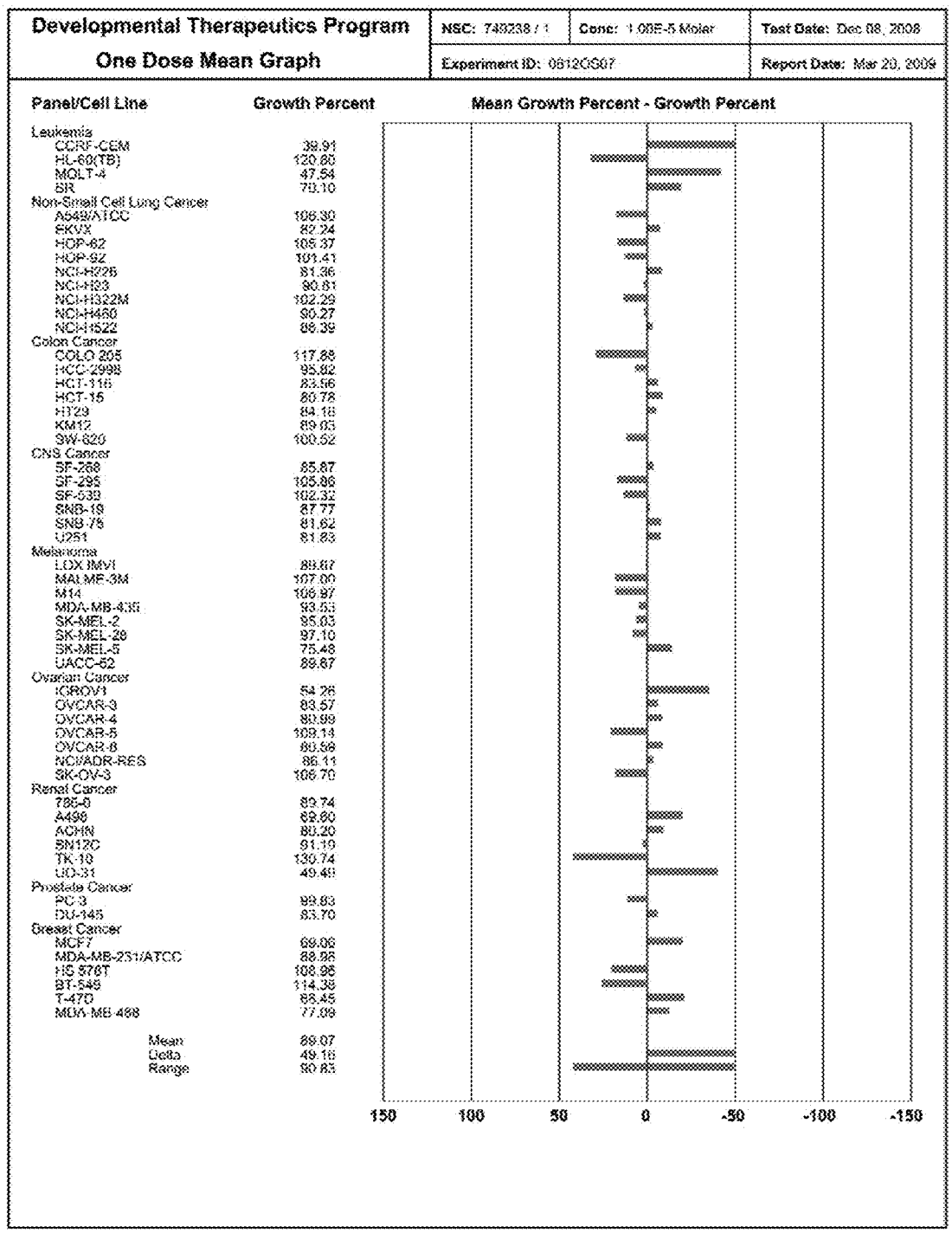
Figure 7:
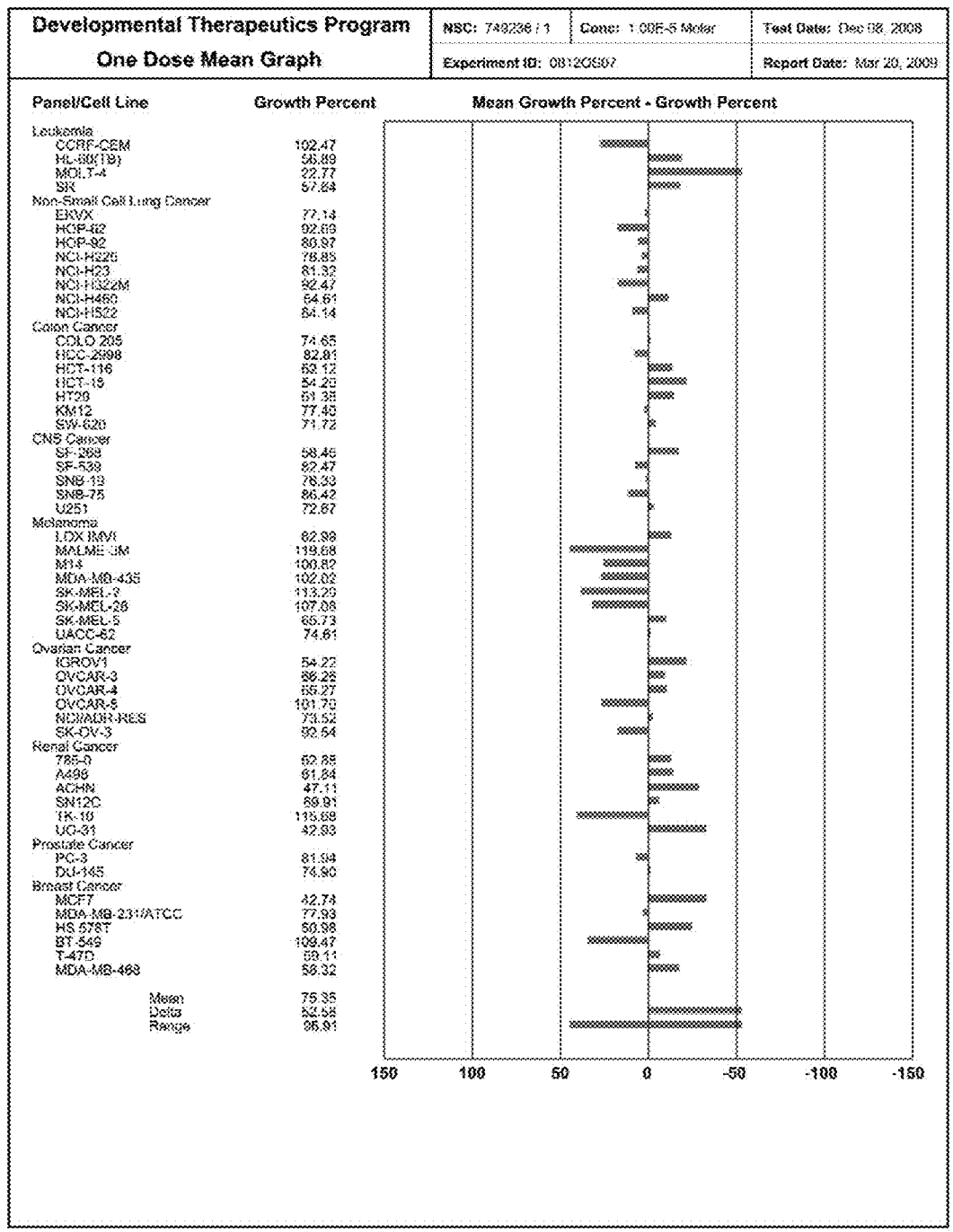
Figure 8:
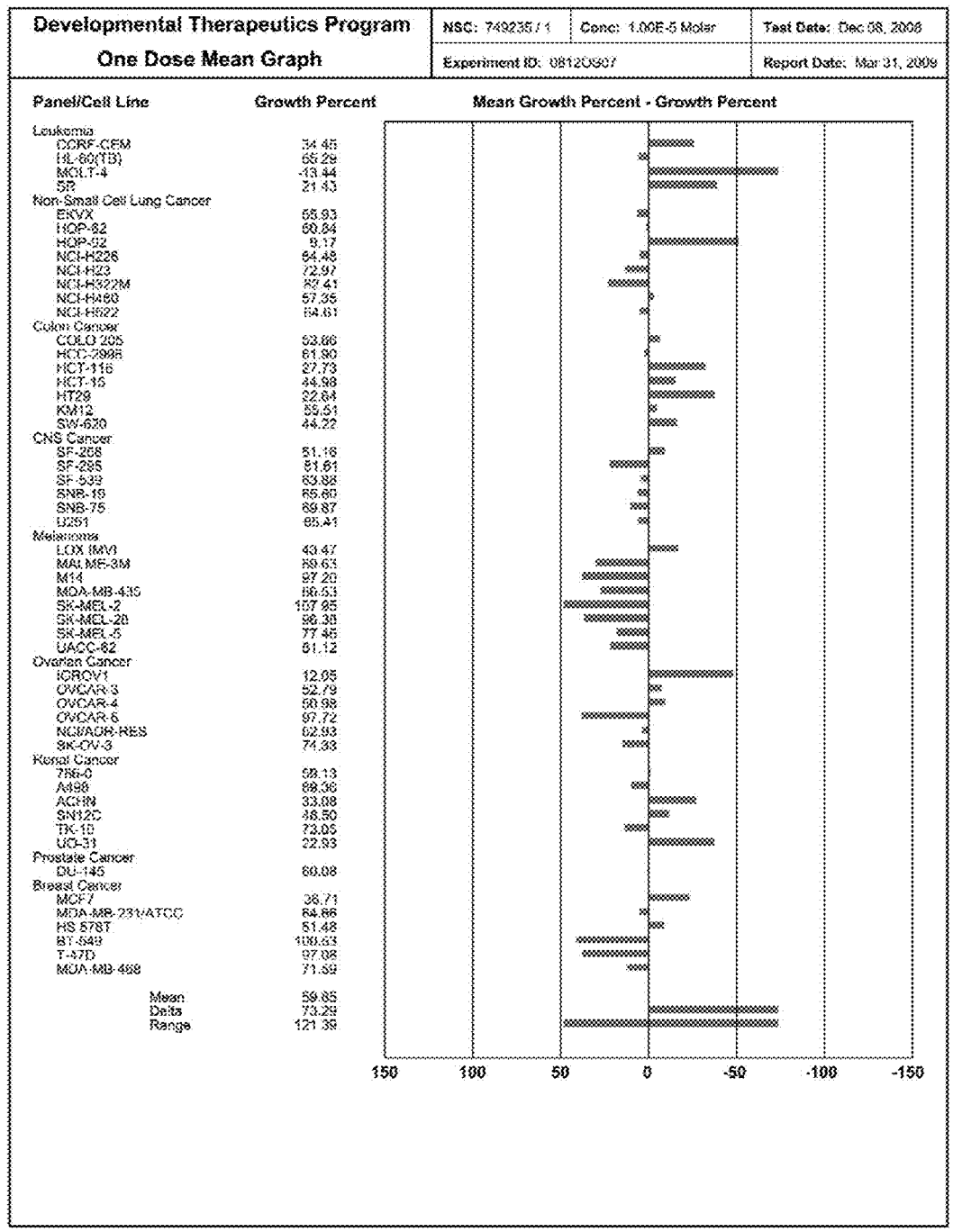
Figure 9:
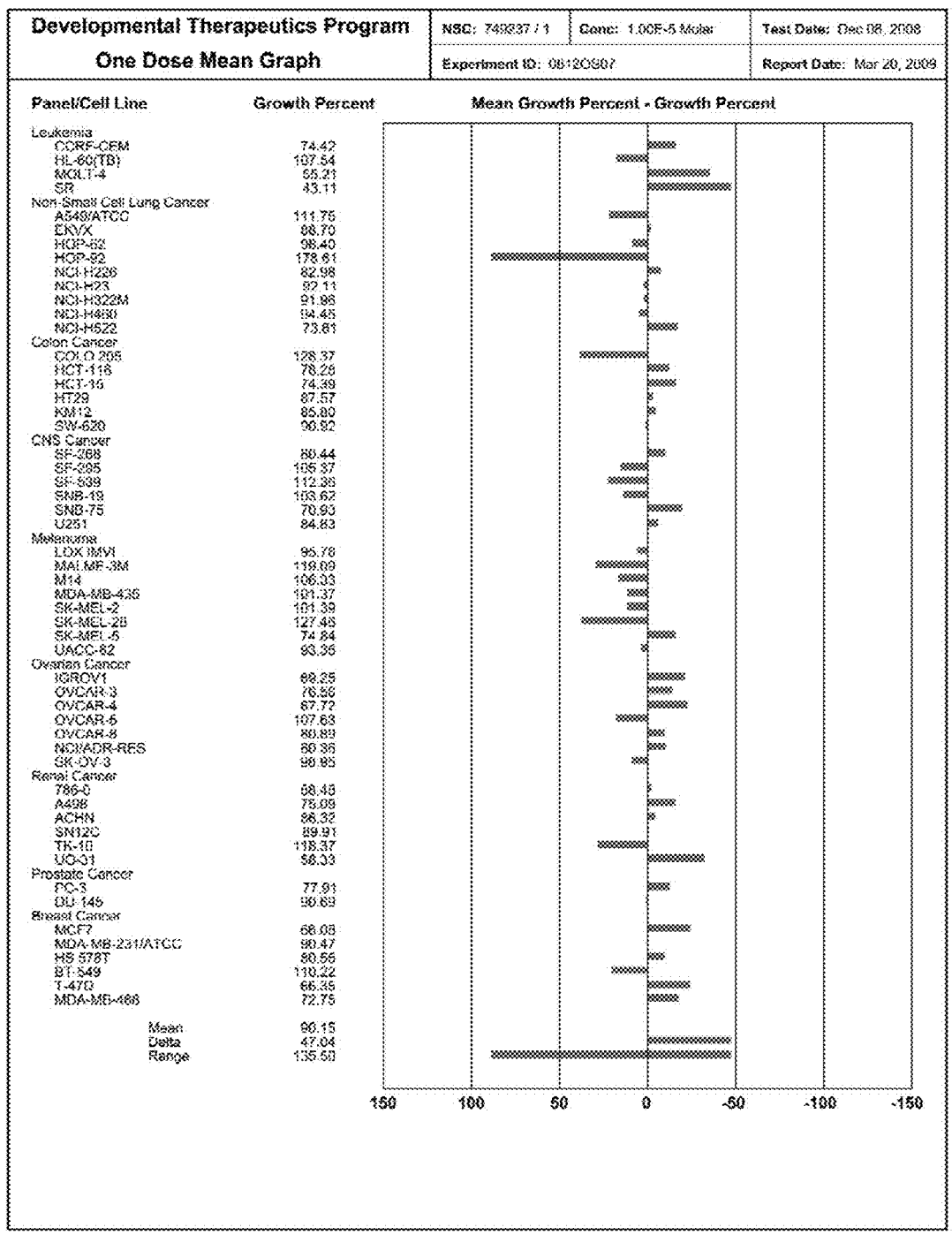
Figure 10:
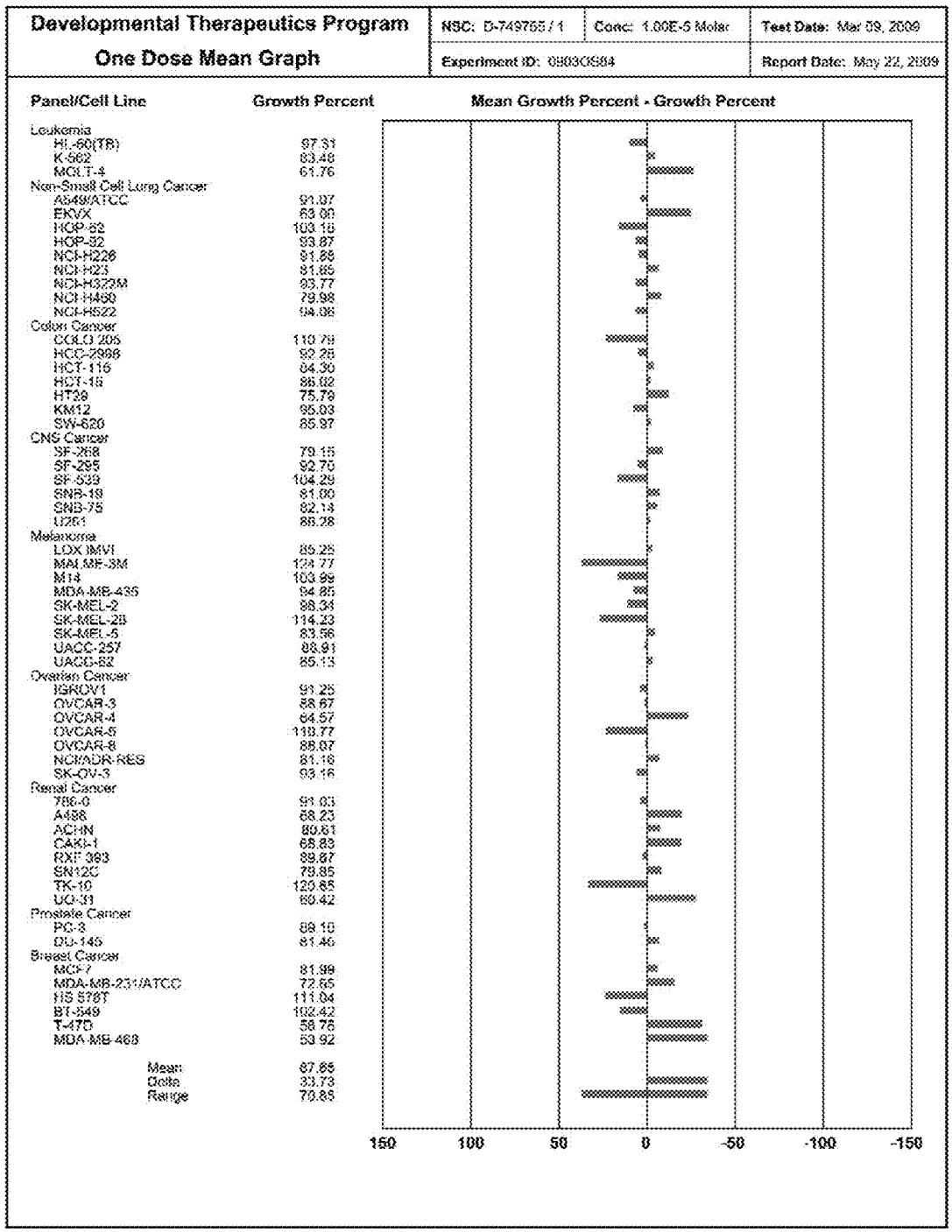

Screening Telomerase Inhibitor by Telomere Repeat Amplification Protocol (TRAP) Assay In the FIGS. 3A, 3B and FIG. 4, a positive control group (P) used water that had been sterilized three times in the assay; while a negative control group (N) used RNase A (CLONTECH) (5 μL, 0.1 mg/mL) in the assay.

In the positive control group (P), due to the absence of inhibitor, the telomerase could extend the telomere, such that some longer telomere fragments could be observed; while there was not observed in the negative control group (N). In the result of TRAP assay (FIG. 3A to 3B), compounds with a concentration of 10 μM was used as the preliminary screening. In the gel, standard compound A was 1,2-diaminoanthraquinone, D was doxorubicin, and M was mitoxantrone. It could find that compound CL20, CL24, and CL25 exhibited more significant inhibition effect/activity of telomerase. Three compounds that exhibited inhibition effect in the preliminary assay were subjected to further assay at different concentrations (1 μM, 10 μM, 100 μM) (FIG. 4). According to the compound CL20 exhibited the highest inhibition effect/activity of telomerase, it was assayed at concentrations of 10, 1, and 0.1 μM; while compounds CL24 and CL25 were assayed at concentrations of 100, 10, and 1 μM.

In conjunction with the result of MTT assay for testing the cell survival rate, it could find that a very high cell survival rate could be obtained in the case of compound CL20 at a concentration of 1 μM, no acute cell toxicity could be observed in the short term assay, and the telomerase inhibiting effect could be observed still at the concentration of 1 μM. In the light of a telomerase inhibitor, compound CL20 is a potential compound of telomerase inhibitor. Therefore, in future drug design of this kind of derivative, longer side chain used as substituent can be attached like that of compound CL20, or performing further modification on substituent of compound CL20.

EXAMPLE 44

Result of MTT Assay and SEAP Assay

A non-small cell lung cancer cell strain H1299 was used in the cell toxicity assay of compounds CL01 to CL40 together with standards 1,2-diaminoanthraquinone, mitoxantrone, and doxorubicin. After being subjected to different compound treatments for 72 hours, cells were treated with a fixed amount of MTT solution for 28 hours. Then, DMSO was used to dissolve back formazan, an O. D. value was detected at wavelength in the range of 550/670 nm, and calculated accordingly the cell survival rate (as shown in Table 1).

The screening result indicated that, among compounds CL01 to CL40 at the concentration of 100 μM and after substrated the effect of DMSO, compounds CL11, CL13, CL17, CL35, CL37, and CL38 exhibited higher relative cell survival rate (40%) and possessed inhibition effect as revealed by P$_{hTERT}$ expression, while other compounds exhibited very high cell toxicity and inhibition effect as revealed by P$_{hTERT}$ expression. Under this high concentration, selectivity of compounds could not be differentiated. Whereas compounds CL01 to CL40 with low concentration of 1 μM, relative cell survival rates were higher than 70%, no significant cell toxicity and inhibition effect as revealed by P$_{hTERT}$ expression could be observed (as shown in Table 1).

Under concentration of 10 μM, compounds CL01, CL06, CL10, CL20, CL24, CL25, CL34, and CL36 exhibited higher cell toxicity, and possessed a relative cell survival rate of less than 50%. Among theses compounds, compound CL20 exhibited further a very high telomerase inhibition effect that could also be observed in the TRAP assay. Compounds CL02, CL03, CL04, CL05, CL07, CL16, CL32, CL33, CL39, and CL40 possessed a relative cell survival rate of higher than 50% and inhibition effect as revealed by P$_{hTERT}$ expression (SEAP assay <50%). It could be suggested that smaller side chain substituent could result into better ratio for inhibition effect on P$_{hTERT}$ expression and cell toxicity, and these kinds of compounds were evaluated as the higher developing potential drug (as shown in Table 1).

The Substituents of Formula I:

The inventive compound is represented by structural formula I:

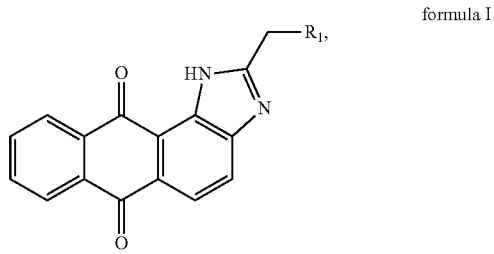

formula I wherein R$_1$ is as defined in CL01 to CL33, and CL35 to CL40 in Table 1;

wherein CL34 compound is represented by structural formula II:

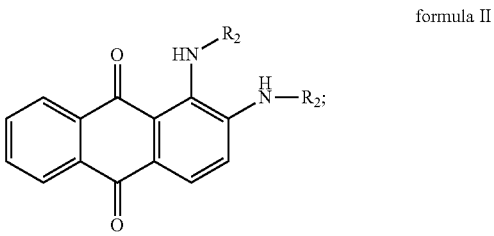

formula II wherein R$_2$ is represented by formula III:

formula III

TABLE 1

Results of screening by MTT and SEAP assays

| Compd. | R₁ | Conc. (μM) | P_{hTERT}-SEAP (H1299) | |
| --- | --- | --- | --- | --- |
| | | | Relative MTT viability (%) | Relative SEAP activity (%) |
| 1,2-diamino anthraquinone | | 1 | 104.66 ± 9.37 | 98.55 ± 11.68 |
| | | 10 | 95.47 ± 3.75 | 77.32 ± 11.57 |
| | | 100 | 39.32 ± 8.84 | 18.16 ± 4.45 |
| | | DMSO | 64.54 ± 8.32 | 32.22 ± 6.29 |
| mitoxantrone | | 1 | 23.68 ± 8.06 | 20.83 ± 1.56 |
| | | 10 | −8.51 ± 1.13 | 9.92 ± 4.80 |
| | | 100 | −0.44 ± 1.01 | 7.19 ± 1.59 |
| | | DMSO | 64.54 ± 8.32 | 32.22 ± 6.29 |
| doxorubicin | | 1 | 17.14 ± 5.37 | 33.78 ± 3.22 |
| | | 10 | −9.79 ± 2.78 | 13.55 ± 3.56 |
| | | 100 | −11.38 ± 4.34 | 5.18 ± 4.01 |
| | | DMSO | 56.36 ± 13.09 | 32.14 ± 5.05 |
| CL01 | —Cl | 1 | 82.27 ± 6.19 | 69.19 ± 1.89 |
| | | 10 | −3.43 ± 1.70 | −0.58 ± 1.16 |
| | | 100 | −5.28 ± 1.13 | 2.87 ± 1.42 |
| | | DMSO | 58.65 ± 4.22 | 39.37 ± 0.88 |
| CL02 |  | 1 | 98.92 ± 6.37 | 83.56 ± 8.52 |
| | | 10 | 64.39 ± 3.07 | 45.12 ± 1.47 |
| | | 100 | −3.87 ± 1.97 | −2.26 ± 0.92 |
| | | DMSO | 58.65 ± 4.22 | 39.37 ± 0.88 |
| CL03 | 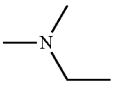 | 1 | 98.92 ± 3.64 | 97.09 ± 11.97 |
| | | 10 | 65.14 ± 3.49 | 38.70 ± 0.23 |
| | | 100 | −2.91 ± 0.24 | −2.69 ± 1.07 |
| | | DMSO | 58.65 ± 4.22 | 39.37 ± 0.88 |
| CL04 | 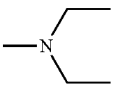 | 1 | 101.40 ± 6.67 | 91.24 ± 4.38 |
| | | 10 | 55.20 ± 4.16 | 32.41 ± 3.73 |
| | | 100 | −1.96 ± 0.27 | 0.13 ± 0.99 |
| | | DMSO | 58.65 ± 4.22 | 39.37 ± 0.88 |
| CL05 | 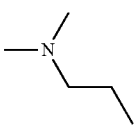 | 1 | 93.48 ± 7.25 | 95.96 ± 6.58 |
| | | 10 | 79.90 ± 4.00 | 34.06 ± 4.31 |
| | | 100 | −2.61 ± 0.90 | −0.38 ± 1.13 |
| | | DMSO | 70.05 ± 4.59 | 41.82 ± 2.66 |
| CL06 | 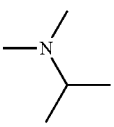 | 1 | 95.90 ± 4.54 | 76.82 ± 2.59 |
| | | 10 | 22.81 ± 2.92 | 1.23 ± 1.34 |
| | | 100 | −2.68 ± 0.86 | −0.52 ± 1.55 |
| | | DMSO | 70.05 ± 4.59 | 41.82 ± 2.66 |
| CL07 | 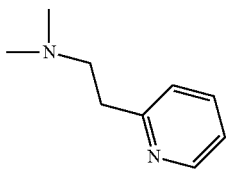 | 1 | 104.35 ± 0.96 | 96.46 ± 5.53 |
| | | 10 | 98.56 ± 6.93 | 51.37 ± 2.23 |
| | | 100 | −0.03 ± 0.65 | −3.16 ± 1.31 |
| | | DMSO | 70.05 ± 4.59 | 41.82 ± 2.66 |
| CL08 | 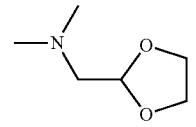 | 1 | 103.82 ± 3.91 | 90.40 ± 2.87 |
| | | 10 | 89.79 ± 2.11 | 68.68 ± 1.77 |
| | | 100 | 28.32 ± 1.44 | 6.78 ± 0.89 |
| | | DMSO | 70.05 ± 4.59 | 41.82 ± 2.66 |
| CL09 | 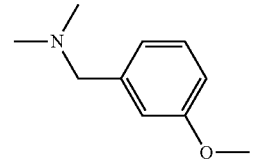 | 1 | 96.62 ± 5.02 | 105.10 ± 3.38 |
| | | 10 | 97.59 ± 2.18 | 78.13 ± 2.34 |
| | | 100 | 9.24 ± 4.62 | −3.01 ± 1.54 |
| | | DMSO | 57.43 ± 4.76 | 44.24 ± 3.18 |

TABLE 1-continued

Results of screening by MTT and SEAP assays

| Compd. | R₁ | Conc. (μM) | P$_{hTERT}$-SEAP (H1299) Relative MTT viability (%) | Relative SEAP activity (%) |
|---|---|---|---|---|
| CL10 | -N(CH₂-2-pyridyl)₂ (methyl) | 1<br>10<br>100<br>DMSO | 100.52 ± 5.98<br>12.89 ± 2.31<br>−2.20 ± 1.66<br>57.43 ± 4.76 | 86.46 ± 3.63<br>−6.44 ± 1.41<br>−7.58 ± 1.71<br>44.24 ± 3.18 |
| CL11 | -CH₂-(9-anthracenyl) with N(CH₃)₂ | 1<br>10<br>100<br>DMSO | 98.03 ± 4.48<br>83.80 ± 5.64<br>42.13 ± 6.80<br>57.43 ± 4.76 | 101.69 ± 5.82<br>77.46 ± 6.40<br>11.72 ± 2.21<br>44.24 ± 3.18 |
| CL12 | -NH-CH₂-(2-CF₃-phenyl) | 1<br>10<br>100<br>DMSO | 98.55 ± 5.49<br>96.34 ± 6.05<br>6.32 ± 2.03<br>57.43 ± 4.76 | 87.27 ± 3.26<br>81.24 ± 6.67<br>−1.71 ± 0.77<br>44.24 ± 3.18 |
| CL13 | -NH-CH₂-(3-CF₃-phenyl) | 1<br>10<br>100<br>DMSO | 114.21 ± 3.31<br>110.28 ± 1.01<br>32.26 ± 2.68<br>74.26 ± 4.04 | 87.11 ± 2.04<br>89.45 ± 2.12<br>4.27 ± 1.03<br>51.58 ± 0.68 |
| CL14 | -NH-CH₂-(4-CF₃-phenyl) | 1<br>10<br>100<br>DMSO | 74.26 ± 4.04<br>10.64 ± 2.42<br>−2.84 ± 1.06<br>74.26 ± 4.04 | 51.58 ± 0.68<br>78.48 ± 7.35<br>2.56 ± 1.14<br>51.58 ± 0.68 |
| CL15 | -NH-CH₂-(3,4-methylenedioxyphenyl) | 1<br>10<br>100<br>DMSO | 109.13 ± 2.02<br>102.85 ± 3.65<br>14.19 ± 2.96<br>74.26 ± 4.04 | 74.55 ± 14.32<br>74.57 ± 17.38<br>1.32 ± 0.84<br>51.58 ± 0.68 |
| CL16 | -N(piperidinyl) | 1<br>10<br>100<br>DMSO | 110.70 ± 8.66<br>79.00 ± 6.13<br>19.57 ± 2.70<br>74.26 ± 4.04 | 75.85 ± 26.86<br>43.80 ± 16.18<br>6.78 ± 2.68<br>51.58 ± 0.68 |
| CL17 | -N(4-methylpiperidinyl) | 1<br>10<br>100<br>DMSO | 114.21 ± 3.31<br>110.28 ± 1.01<br>32.26 ± 2.68<br>73.72 ± 3.85 | 102.27 ± 4.81<br>97.32 ± 5.33<br>25.55 ± 4.89<br>67.99 ± 6.94 |
| CL18 | -N(azepanyl) | 1<br>10<br>100<br>DMSO | 104.00 ± 6.82<br>85.13 ± 1.24<br>−4.48 ± 0.86<br>73.72 ± 3.85 | 106.60 ± 5.16<br>66.49 ± 3.59<br>3.79 ± 0.28<br>67.99 ± 6.94 |
| CL19 | -N(1,4-dioxa-8-azaspiro[4.5]decyl) | 1<br>10<br>100<br>DMSO | 102.72 ± 2.09<br>79.24 ± 5.94<br>14.81 ± 2.64<br>73.72 ± 3.85 | 97.03 ± 1.84<br>95.53 ± 1.11<br>14.09 ± 1.83<br>67.99 ± 6.94 |

TABLE 1-continued

Results of screening by MTT and SEAP assays

| | | | $P_{hTERT}$-SEAP (H1299) | |
|---|---|---|---|---|
| Compd. | $R_1$ | Conc. (μM) | Relative MTT viability (%) | Relative SEAP activity (%) |
| CL20 | piperidine-CH2CH2-piperidine (NH, HN) | 1<br>10<br>100<br>DMSO | 96.95 ± 4.74<br>−5.74 ± 0.50<br>−2.05 ± 1.07<br>73.72 ± 3.85 | 96.04 ± 5.48<br>7.52 ± 0.28<br>3.08 ± 0.59<br>67.99 ± 6.94 |
| CL21 | morpholine | 1<br>10<br>100<br>DMSO | 89.85 ± 2.58<br>70.79 ± 4.43<br>13.45 ± 5.65<br>82.62 ± 4.58 | 102.27 ± 4.81<br>97.32 ± 5.33<br>25.55 ± 4.89<br>90.20 ± 0.53 |
| CL22 | thiomorpholine | 1<br>10<br>100<br>DMSO | 91.80 ± 3.61<br>77.46 ± 3.93<br>0.93 ± 0.72<br>82.62 ± 4.58 | 115.23 ± 2.45<br>76.66 ± 2.30<br>4.62 ± 0.64<br>90.20 ± 0.53 |
| CL23 | thiazolidine | 1<br>10<br>100<br>DMSO | 89.27 ± 4.79<br>75.54 ± 7.26<br>5.18 ± 2.04<br>82.62 ± 4.58 | 106.11 ± 3.01<br>85.58 ± 0.76<br>11.89 ± 0.74<br>90.20 ± 0.53 |
| CL24 | 4-methylpiperazine | 1<br>10<br>100<br>DMSO | 87.39 ± 5.52<br>35.20 ± 3.89<br>−3.02 ± 0.78<br>82.62 ± 4.58 | 105.62 ± 2.94<br>23.22 ± 0.76<br>6.23 ± 0.60<br>90.20 ± 0.53 |
| CL25 | 4-ethylpiperazine | 1<br>10<br>100<br>DMSO | 86.23 ± 5.18<br>35.26 ± 4.07<br>−2.01 ± 0.74<br>51.94 ± 4.72 | 91.79 ± 3.00<br>13.62 ± 1.28<br>−4.43 ± 0.94<br>32.50 ± 8.12 |
| CL26 | 4-allylpiperazine | 1<br>10<br>100<br>DMSO | 86.01 ± 3.37<br>44.84 ± 4.24<br>−1.06 ± 0.60<br>51.94 ± 4.72 | 87.20 ± 1.82<br>16.71 ± 3.61<br>−6.77 ± 0.91<br>32.50 ± 8.12 |
| CL27 | 4-phenylpiperazine | 1<br>10<br>100<br>DMSO | 90.19 ± 3.86<br>54.41 ± 4.18<br>18.14 ± 4.07<br>51.94 ± 4.72 | 92.23 ± 0.78<br>76.74 ± 6.32<br>5.83 ± 3.88<br>32.50 ± 8.13 |
| CL28 | 4-(2-pyridyl)piperazine | 1<br>10<br>100<br>DMSO | 90.54 ± 4.34<br>69.47 ± 4.26<br>19.82 ± 1.69<br>51.94 ± 4.72 | 91.21 ± 2.69<br>57.15 ± 1.19<br>1.12 ± 1.22<br>32.50 ± 8.13 |
| CL29 | 4-(2-pyrimidinyl)piperazine | 1<br>10<br>100<br>DMSO | 85.47 ± 3.17<br>73.70 ± 2.25<br>28.16 ± 1.88<br>72.02 ± 6.50 | 111.34 ± 3.55<br>92.24 ± 3.20<br>19.36 ± 2.47<br>34.16 ± 9.78 |
| CL30 | 4-(2-fluorophenyl)piperazine | 1<br>10<br>100<br>DMSO | 88.38 ± 2.16<br>76.69 ± 2.25<br>14.78 ± 2.25<br>72.02 ± 6.50 | 102.97 ± 3.44<br>78.25 ± 3.65<br>−0.29 ± 0.83<br>34.16 ± 9.78 |
| CL31 | 4-(2-cyanophenyl)piperazine | 1<br>10<br>100<br>DMSO | 78.32 ± 5.02<br>61.68 ± 5.79<br>21.63 ± 1.16<br>72.02 ± 6.50 | 106.16 ± 4.67<br>56.73 ± 8.14<br>5.59 ± 1.33<br>34.16 ± 9.78 |
| CL32 | 4-(3-methoxyphenyl)piperazine | 1<br>10<br>100<br>DMSO | 81.32 ± 9.72<br>58.05 ± 6.70<br>23.93 ± 3.22<br>72.02 ± 6.50 | 105.21 ± 5.64<br>30.49 ± 6.58<br>3.33 ± 0.46<br>34.16 ± 9.78 |

TABLE 1-continued

Results of screening by MTT and SEAP assays

| Compd. | $R_1$ | Conc. (μM) | P$_{hTERT}$-SEAP (H1299) | |
|---|---|---|---|---|
| | | | Relative MTT viability (%) | Relative SEAP activity (%) |
| CL33 | —N(piperazine)N—CH$_2$—phenyl | 1<br>10<br>100<br>DMSO | 92.61 ± 1.56<br>50.61 ± 8.05<br>12.65 ± 2.56<br>52.98 ± 4.74 | 97.78 ± 7.20<br>10.77 ± 1.43<br>−2.70 ± 0.48<br>28.36 ± 3.78 |
| CL34 | formula II | 1<br>10<br>100<br>DMSO | 94.09 ± 3.21<br>34.06 ± 4.63<br>5.85 ± 2.10<br>52.98 ± 4.74 | 87.40 ± 4.51<br>12.47 ± 4.35<br>−2.74 ± 0.61<br>28.36 ± 3.78 |
| CL35 | —CH$_2$CH$_2$Cl | 1<br>10<br>100<br>DMSO | 91.08 ± 5.56<br>85.63 ± 3.22<br>40.27 ± 1.32<br>52.98 ± 4.74 | 94.73 ± 9.12<br>82.76 ± 5.38<br>7.62 ± 4.08<br>28.36 ± 3.78 |
| CL36 | Et-N(piperazine)N-Me | 1<br>10<br>100<br>DMSO | 87.16 ± 6.98<br>32.26 ± 6.14<br>−1.78 ± 0.49<br>52.98 ± 4.74 | 73.91 ± 3.20<br>7.10 ± 4.67<br>−3.06 ± 0.58<br>28.36 ± 3.78 |
| CL37 | Et-N(piperazine)N-phenyl | 1<br>10<br>100<br>DMSO | 94.04 ± 0.98<br>96.47 ± 13.72<br>64.15 ± 8.75<br>64.86 ± 11.76 | 103.79 ± 4.96<br>92.66 ± 5.37<br>36.58 ± 2.44<br>26.24 ± 3.58 |
| CL38 | Et-N(piperazine)N-(2-pyridyl) | 1<br>10<br>100<br>DMSO | 97.97 ± 7.72<br>92.83 ± 8.10<br>57.03 ± 10.76<br>64.86 ± 11.76 | 87.57 ± 8.63<br>62.88 ± 2.52<br>1.49 ± 3.34<br>26.24 ± 3.58 |
| CL39 | Et-N(piperazine)N-(2-pyrimidyl) | 1<br>10<br>100<br>DMSO | 90.71 ± 5.81<br>83.99 ± 7.67<br>−1.52 ± 2.33<br>64.86 ± 11.76 | 82.96 ± 3.61<br>34.78 ± 2.99<br>−8.09 ± 0.65<br>26.24 ± 3.58 |
| CL40 | Et-N(piperazine)N-CH$_2$-phenyl | 1<br>10<br>100<br>DMSO | 95.60 ± 8.22<br>53.67 ± 8.69<br>6.65 ± 3.34<br>64.86 ± 11.76 | 72.97 ± 8.24<br>5.05 ± 4.62<br>−7.29 ± 0.95<br>26.24 ± 3.58 |

In the invention, compounds having stronger cell toxicity were used in the following examples to investigate their selectivity and specificity with respect to the toxicity of different cancer cells. These compounds were, such as compounds CL04, CL07, CL16, CL24, CL27, and CL28 screened by The United State National Cancer Institute (NCI).

EXAMPLE 45

The Cytotoxicity Result of National Cancer Institute's Anticancer Drug Screen The screening system in United State National Cancer Institute (NCI) consists of 60 kinds of different human cancer cells, which can be used to assay the growth-inhibiting ability or cell toxicity of a compound against various cancer and tumor at a certain concentration. The NCI had selected 6 compounds synthesized above, and performed cell toxicity assay against 60 kinds of cancer cell strains (Table 2) (DTP Human Tumor Cell Line Screen), in which each compound was assayed at a certain concentration to observe its inhibition ability or cell toxicity against various kinds of cancer and tumor.

Compounds CL04, CL07, CL16, CL24, CL27, and CL28 were listed as test compounds ((FIG. 2, and Table 2) in the NCI's screen. The results (Table 3 and FIG. 5 to FIG. 10) indicated that compounds CL04 and CL24 exhibited very strong inhibition effect on the cell growth of Leukemia cell strain MOLT-4, and hence was quite suitable to be used as a chemotherapy drug. In addition, in the assay against human multiple drug-resistant breast cancer cell NCI/ADR-RES (derived from ovarian cancer), compounds CL24 possessed drug-resistance against adriamycin (ADR).

TABLE 2

The list of tested compounds in NCI's screen (One Dose Mean Graph)

| No | Formula | Compound info. | Code | NSC no. |
|---|---|---|---|---|
| 1 | | 2-((diethylamino)methyl)-1H-anthra[1,2-d]imidazole-6,11-dione<br>Chemical Formula: $C_{20}H_{19}N_3O_2$<br>Molecular Weight : 333.3838 | CL04 | 749234<br>(FIG. 5) |
| 2 | | 2-((N-methyl-2-(pyridin-2-yl)ethanamino)methyl)-1H-anthra[1,2-d]imidazole-6,11-dione<br>Chemical Formula: $C_{24}H_{20}N_4O_2$<br>Molecular Weight : 396.4412 | CL07 | 749238<br>(FIG. 6) |
| 3 | | 2-((piperidin-1-yl)methyl)-1H-anthra[1,2-d]imidazole-6,11-dione<br>Chemical Formula: $C_{21}H_{19}N_3O_2$<br>Molecular Weight : 345.3945 | CL16 | 749236<br>(FIG. 7) |
| 4 | | 2-((4-methylpiperazin-1-yl)methyl)-1H-anthra[1,2-d]imidazole-6,11-dione<br>Chemical Formula: $C_{21}H_{20}N_4O_2$<br>Molecular Weight : 360.4091 | CL24 | 749235<br>(FIG. 8) |
| 5 | | 2-((4-phenylpiperazin-1-yl)methyl)-1H-anthra[1,2-d]imidazole-6,11-dione<br>Chemical Formula: $C_{26}H_{22}N_4O_2$<br>Molecular Weight : 422.4785 | CL27 | 749237<br>(FIG. 9) |

TABLE 2-continued

The list of tested compounds in NCI's screen (One Dose Mean Graph)

| No | Formula | Compound info. | Code | NSC no. |
|---|---|---|---|---|
| 6 | [structure] | 2-((4-(pyridin-2-yl)piperazin-1-yl)methyl)-1H-anthra[1,2-d]imidazole-6,11-dione<br>Chemical Formula: $C_{25}H_{21}N_5O_2$<br>Molecular Weight: 423.4665 | CL28 | 749765 (FIG. 10) |

*The tested concentration of compounds is 1.00E−5 Molar.

TABLE 3

Cytotoxicity of selected compounds in the NCI drug screen

Compound/Growth Percent[a]

| Panel/Cell Line | CL04 749234 | CL07 749238 | CL16 749236 | CL24 749235 | CL27 749237 | CL28 749765 |
|---|---|---|---|---|---|---|
| Leukemia | | | | | | |
| CCRF-CEM | 47.88 | 39.91 | 102.47 | 34.45 | 74.42 | — |
| HL-60(TB) | 68.18 | 120.08 | 56.89 | 65.29 | 107.54 | 97.31 |
| MOLT-4 | −9.43 | 47.54 | 22.77 | −13.44 | 55.21 | 61.76 |
| SR | 42.38 | 70.10 | 57.64 | 21.48 | 43.11 | — |
| K562 | — | — | — | — | — | 83.48 |
| Non-Small Cell Lung Cancer | | | | | | |
| EKVX | 73.22 | 82.24 | 77.14 | 65.93 | 88.70 | 63.00 |
| HOP-62 | 85.27 | 105.37 | 92.69 | 60.84 | 98.40 | 103.18 |
| HOP-92 | 56.11 | 101.41 | 80.97 | 9.17 | 178.61 | 93.87 |
| NCI-H226 | 77.20 | 81.36 | 78.85 | 64.48 | 82.98 | 91.88 |
| NCI-H23 | 75.96 | 90.81 | 81.32 | 72.97 | 92.11 | 81.65 |
| NCI-H322M | 90.06 | 102.29 | 92.47 | 82.41 | 91.96 | 93.77 |
| NCI-H460 | 55.50 | 90.27 | 64.61 | 57.35 | 94.45 | 79.98 |
| NCI-H522 | 73.14 | 86.39 | 84.14 | 64.61 | 73.61 | 94.06 |
| A549/ATCC | — | 106.30 | — | — | 111.76 | 91.07 |
| Colon Cancer | | | | | | |
| COLO 205 | 81.00 | 117.88 | 74.65 | 53.66 | 128.37 | 110.79 |
| HCC-2998 | 80.61 | 95.82 | 82.81 | 61.90 | — | 92.28 |
| HCT-116 | 48.22 | 83.56 | 62.12 | 27.73 | 78.28 | 84.30 |
| HCT-15 | 65.75 | 80.78 | 54.20 | 44.98 | 74.39 | 86.02 |
| HT29 | 56.02 | 84.18 | 61.38 | 22.64 | 87.57 | 75.79 |
| KM12 | 76.89 | 89.03 | 77.40 | 55.51 | 85.80 | 95.03 |
| SW-620 | 60.46 | 100.52 | 71.72 | 44.22 | 90.92 | 85.97 |
| CNS Cancer | | | | | | |
| SF-268 | 74.04 | 85.87 | 58.46 | 51.16 | 80.44 | 79.15 |
| SF-295 | 89.56 | 105.86 | — | 81.61 | 105.37 | 92.70 |
| SF-539 | 85.26 | 102.32 | 82.47 | 63.88 | 112.36 | 104.29 |
| SNB-19 | 75.06 | 87.77 | 76.33 | 65.60 | 103.62 | 81.00 |
| SNB-75 | 82.03 | 81.62 | 86.42 | 69.87 | 70.93 | 82.14 |
| U251 | 70.77 | 81.83 | 72.67 | 65.41 | 84.83 | 86.28 |
| Melanoma | | | | | | |
| LOX IMVI | 61.98 | 89.67 | 62.99 | 43.47 | 95.76 | 82.25 |
| MALME-3M | 98.45 | 107.00 | 119.68 | 89.63 | 119.09 | 124.77 |
| M14 | 97.86 | 106.97 | 100.82 | 97.20 | 106.33 | 103.99 |
| MDA-MB-435 | 88.53 | 93.53 | 102.02 | 86.53 | 101.37 | 94.85 |
| SK-MEL-2 | 102.69 | 95.03 | 113.29 | 107.95 | 101.39 | 98.34 |
| SK-MEL-28 | 92.41 | 97.01 | 107.08 | 96.38 | 127.46 | 114.23 |
| SK-MEL-5 | 68.20 | 75.48 | 65.73 | 77.46 | 74.84 | 83.56 |
| UACC-62 | 68.47 | 89.67 | 74.61 | 81.12 | 93.36 | 85.13 |
| UACC-257 | — | — | — | — | — | 88.91 |
| Ovarian Cancer | | | | | | |
| IGROV1 | 13.61 | 54.26 | 54.22 | 12.05 | 69.25 | 91.25 |
| OVCAR-3 | 63.32 | 83.57 | 66.26 | 52.79 | 76.56 | 88.67 |
| OVCAR-4 | 65.69 | 80.99 | 65.27 | 50.98 | 67.72 | 64.57 |
| OVCAR-5 | 96.50 | 109.14 | 101.70 | 97.72 | 107.63 | 110.77 |
| OVCAR-8 | — | 80.59 | — | — | 80.89 | 88.07 |
| NCI/ADR-RES | 65.32 | 86.11 | 73.52 | 62.93 | 80.36 | 81.16 |
| SK-OV-3 | 86.81 | 106.7 | 92.54 | 74.33 | 98.95 | 93.16 |
| Renal Cancer | | | | | | |
| 786-0 | 64.88 | 89.74 | 62.88 | 59.13 | 88.48 | 91.03 |
| A489 | 49.50 | 69.60 | 61.84 | 69.36 | 75.09 | 68.23 |
| ACHN | 48.41 | 80.20 | 47.11 | 33.08 | 86.32 | 80.61 |
| SN12C | 69.04 | 91.19 | 96.96 | 48.50 | 89.91 | 79.85 |
| TK-10 | 98.12 | 130.74 | 115.68 | 73.05 | 118.37 | 120.65 |
| UO-31 | 27.21 | 49.49 | 42.93 | 22.93 | 58.33 | 60.42 |
| CAKI-1 | — | — | — | — | — | 68.83 |
| RXF 393 | — | — | — | — | — | 89.67 |
| Prostate Cancer | | | | | | |
| DU145 | 73.54 | 83.70 | 74.90 | 60.08 | 90.69 | 81.46 |
| PC-3 | — | 99.83 | 81.94 | — | 77.91 | 89.10 |
| Breast Cancer | | | | | | |
| MCF7 | 51.13 | 69.06 | 42.74 | 36.71 | 66.08 | 81.99 |
| MDA-MB-231/ATCC | 75.52 | 88.98 | 77.93 | 61.66 | 90.47 | 72.65 |
| HS 578-T | 70.37 | 108.96 | 50.98 | 51.48 | 80.56 | 111.04 |
| BT-549 | 105.50 | 114.38 | 109.47 | 100.53 | 110.22 | 102.42 |
| T-47D | 83.55 | 68.45 | 69.11 | 97.08 | 66.35 | 56.78 |
| MDA-MB-468 | 54.46 | 77.09 | 58.32 | 71.59 | 72.75 | 53.92 |
| Mean | 69.66 | 89.07 | 75.35 | 59.85 | 90.15 | 87.65 |
| Delta | 79.09 | 49.16 | 52.58 | 73.29 | 47.04 | 33.73 |
| Range | 114.93 | 90.83 | 96.91 | 121.39 | 135.50 | 70.85 |

[a]Data obtained from NCI in vitro 60-cell Drug Screen program at 1.00E−5 Molar concentration.
"—" represent "not test".

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A compound selected from the group consisting of:
2-((dimethylamino)methyl)-1H-anthra[1,2-d]imidazole-6,11-dione, 2-((ethylmethylamino)methyl)-1H-anthra[1,2-d]imidazole-6,11-dione,
2-((diethylamino)methyl)-1H-anthra[1,2-d]imidazole-6,11-dione,
2-((methylpropylamino)methyl)-1H-anthra[1,2-d]imidazole-6,11-dione,
2-((ethylisopropylamino)methyl)-1H-anthra[1,2-d]imidazole-6,11-dione,
2-((N-methyl-2-(pyridin-2-yl)ethanamino)methyl)-1H-anthra[1,2-d]imidazole-6,11-dione,
2-(((1,3-dioxolan-2-yl)-N-methylmethanamino)methyl)-1H-anthra[1,2-d]imidazole-6,11-dione,
2-(((3-methoxy-N-methybenzylamino)methyl)-1H-anthra[1,2-d]imidazole-6,11-dione,
2-((di-(2-picolyl)amino)methyl)-1H-anthra[1,2-d]imidazole-6,11-dione,
2-(((anthracen-10-yl)-N-methylmethanamino)methyl)-1H-anthra[1,2-d]imidazole-6,11-dione,
2-((2-(trifluoromethyl)benzylamino)methyl)-1H-anthra[1,2-d]imidazole-6,11-dione,
2-((3-(trifluoromethyl)benzylamino)methyl)-1H-anthra[1,2-d]imidazole-6,11-dione,
2-((4-(trifluoromethyl)benzylamino)methyl)-1H-anthra[1,2-d]imidazole-6,11-dione,
2-((piperonylamino)methyl)-1H-anthra[1,2-d]imidazole-6,11-dione,
2-((piperidin-1-yl)methyl)-1H-anthra[1,2-d]imidazole-6,11-dione,
2-((4-methylpiperidin-1-yl)methyl)-1H-anthra[1,2-d]imidazole-6,11-dione,
2-((azepan-1-yl)methyl)-1H-anthra[1,2-d]imidazole-6,11-dione,
2-((1,4-dioxa-8-azaspiro[4.5]decane-8-yl)methyl)-1H-anthra[1,2-d]imidazole-6,11-dione,
2-((4-(3-(piperidin-4-yl)propyl)piperidin-1-yl)methyl)-1H-anthra[1,2-d]imidazole-6,11-dione,
2-(thiomorpholinomethyl)-1H-anthra[1,2-d]imidazole-6,11-dione,
2-((thiazolidin-3-yl)methyl)-1H-anthra[1,2-d]imidazole-6,11-dione,
2-((4-methylpiperazin-1-yl)methyl)-1H-anthra[1,2-d]imidazole-6,11-dione,
2-((4-ethylpiperazin-1-yl)methyl)-1H-anthra[1,2-d]imidazole-6,11-dione,
2-((4-allylpiperazin-1-yl)methyl)-1H-anthra[1,2-d]imidazole-6,11-dione,
2-((4-phenylpiperazin-1-yl)methyl)-1H-anthra[1,2-d]imidazole-6,11-dione,
2-((4-(pyridin-2-yl)piperazin-1-yl)methyl)-1H-anthra[1,2-d]imidazole-6,11-dione,
2-((4-(pyrimidin-2-yl)piperazin-1-yl)methyl)-1H-anthra[1,2-d]imidazole-6,11-dione,
2-((4-(2-fluorophenyl)piperazin-1-yl)methyl)-1H-anthra[1,2-d]imidazole-6,11-dione,
2-((4-(2-cyanophenyl)piperazin-1-yl)methyl)-1H-anthra[1,2-d]imidazole-6,11-dione,
2-((4-(3-methoxyphenyl)piperazin-1-yl)methyl)-1H-anthra[1,2-d]imidazole-6,11-dione,
2-((4-benzylpiperazin-1-yl)methyl)-1H-anthra[1,2-d]imidazole-6,11-dione,
1,2-bis(3-chloropropionamido)anthraquinone,
2-(2-chloroethyl)-1H-anthra[1,2-d]imidazole-6,11-dione,
2-(2-(4-methylpiperazin-1-yl)ethyl)-1H-anthra[1,2-d]imidazole-6,11-dione,
2-(2-(4-phenylpiperazin-1-yl)ethyl)-1H-anthra[1,2-d]imidazole-6,11-dione,
2-(2-(4-(pyridin-2-yl)piperazin-1-yl)ethyl)-1H-anthra[1,2-d]imidazole-6,11-dione,
2-(2-(4-(pyrimidin-2-yl)piperazin-1-yl)ethyl)-1H-anthra[1,2-d]imidazole-6,11-dione, and
2-(2-(4-benzylpiperazin-1-yl)ethyl)-1H-anthra[1,2-d]imidazole-6,11-dione.

2. A method for preparing the compound as recited in claim 1, which comprises steps 1-2 or steps 3-5, wherein:

step 1:
dissolving 1,2-diaminoanthraquinone in N—N-dimethylformamide; adding thereto with chloroacetyl chloride under stirring; after complete of the reaction, cooling down the mixed solution; filtering to collect the precipitate; and finally, rinsing the precipitate with ethanol to obtain 2-(chloromethyl)-1H-anthra[1,2-d]imidazole-6,11-dione; and step 2:
stirring said 2-(chloromethyl)-1H-anthra[1,2-d]imidazole-6,11-dione and N,N-Diisopropylethylamine or triethylamine in tetrahydrofuran; adding thereto with an amine; heating the mixed solution under reflux; after completion of the reaction, concentrating the mixed solution under reduced pressure; extracting the concentrated mixture with ethyl acetate; drying the extract by MgSO$_4$; concentrating the extract; recrystallizing the concentrated extract in ethyl acetate/n-hexane; filtering the ethyl acetate/n-hexane mixture to collect crystal; rinsing the crystal with acetone to obtain the compound 2-((dimethylamino)methyl)-1H-anthra[1,2-d]imidazole-6,11-dione,
2-((ethylmethylamino)methyl)-1H-anthra[1,2-d]imidazole-6,11-dione,
2-((diethylamino)methyl)-1H-anthra[1,2-d]imidazole-6,11-dione,
2-((methylpropylamino)methyl)-1H-anthra[1,2-d]imidazole-6,11-dione,
2-((ethylisopropylamino)methyl)-1H-anthra[1,2-d]imidazole-6,11-dione,
2-((N-methyl-2-(pyridin-2-yl)ethanamino)methyl)-1H-anthra[1,2-d]imidazole-6,11-dione,
2-(((1,3-dioxolan-2-yl)-N-methylmethanamino)methyl)-1H-anthra[1,2-d]imidazole-6,11-dione,
2-((3-methoxy-N-methybenzylamino)methyl)-1H-anthra[1,2-d]imidazole-6,11-dione,
2-((di-(2-picolyl)amino)methyl)-1H-anthra[1,2-d]imidazole-6,11-dione,
2-(((anthracen-10-yl)-N-methylmethanamino)methyl)-1H-anthra[1,2-d]imidazole-6,11-dione,
2-((2-(trifluoromethyl)benzylamino)methyl)-1H-anthra[1,2-d]imidazole-6,11-dione,
2-((3-(trifluoromethyl)benzylamino)methyl)-1H-anthra[1,2-d]imidazole-6,11-dione,
2-((4-(trifluoromethyl)benzylamino)methyl)-1H-anthra[1,2-d]imidazole-6,11-dione,
2-((piperonylamino)methyl)-1H-anthra[1,2-d]imidazole-6,11-dione,
2-((piperidin-1-yl)methyl)-1H-anthra[1,2-d]imidazole-6,11-dione,
2-((4-methylpiperidin-1-yl)methyl)-1H-anthra[1,2-d]imidazole-6,11-dione,
2-((azepan-1-yl)methyl)-1H-anthra[1,2-d]imidazole-6,11-dione,
2-((1,4-dioxa-8-azaspiro[4.5]decane-8-yl)methyl)-1H-anthra[1,2-d]imidazole-6,11-dione,
2-((4-(3-(piperidin-4-yl)propyl)piperidin-1-yl)methyl)-1H-anthra[1,2-d]imidazole-6,11-dione, 2-(thiomorpholinomethyl)-1H-anthra[1,2-d]imidazole-6,11-dione,
2-((thiazolidin-3-yl)methyl)-1H-anthra[1,2-d]imidazole-6,11-dione,
2-((4-methylpiperazin-1-yl)methyl)-1H-anthra[1,2-d]imidazole-6,11-dione,
2-((4-ethylpiperazin-1-yl)methyl)-1H-anthra[1,2-d]imidazole-6,11-dione,
2-((4-allylpiperazin-1-yl)methyl)-1H-anthra[1,2-d]imidazole-6,11-dione,
2-((4-phenylpiperazin-1-yl)methyl)-1H-anthra[1,2-d]imidazole-6,11-dione,
2-((4-(pyridin-2-yl)piperazin-1-yl)methyl)-1H-anthra[1,2-d]imidazole-6,11-dione,
2-((4-(pyrimidin-2-yl)piperazin-1-yl)methyl)-1H-anthra[1,2-d]imidazole-6,11-dione,
2-((4-(2-fluorophenyl)piperazin-1-yl)methyl)-1H-anthra[1,2-d]imidazole-6,11-dione,
2-((4-(2-cyanophenyl)piperazin-1-yl)methyl)-1H-anthra[1,2-d]imidazole-6,11-dione,
2-((4-(3-methoxyphenyl)piperazin-1-yl)methyl)-1H-anthra[1,2-d]imidazole-6,11-dione, or
2-((4-benzylpiperazin-1-yl)methyl)-1H-anthra[1,2-d]imidazole-6,11-dione; or step 3:
  dissolving compound 1,2-diaminoanthraquinone in N—N-dimethylformamide; adding thereto successively with triethylamine and 3-chloropropionyl chloride under stirring; after completion of reaction, cooling down the mixed solution; filtering to collect the precipitate; and finally, rinsing the precipitate with ethanol to obtain 1,2-bis(3-chloropropionamido)anthraquinone;

step 4:
  dissolving said 1,2-bis(3-chloropropionamido)anthraquinone in 50% sulfuric acid at 0° C.; reacting by stirring in an oil bath at a temperature of about 110° C.; after completion of the reaction, extracting the mixed solution with dichloromethane; drying the extract by MgSO$_4$; then concentrating the extract under reduced pressure to obtain a crude produce; rinsing the crude product with acetone to obtain 2-(2-chloroethyl)-1H-anthra[1,2-d]imidazole-6,11-dione; and step 5:
  stirring said 2-(2-chloroethyl)-1H-anthra[1,2-d]imidazole-6,11-dione, N,N-Diisopropylethylamine and an amine in tetrahydrofuran (THF); reacting the mixed solution by heating under reflux; after completion of reaction, concentrating the mixed solution under reduced pressure; extracting the concentrated mixture with ethyl acetate; drying the extract by MgSO$_4$; concentrating the extract under reduced pressure to obtain a crude product; recrystallizing the crude product in ethyl acetate/n-hexane; filtering to collect the crystal; rinsing the crystal with acetone to obtain the compound 2-(2-(4-methylpiperazin-1-yl)ethyl)-1H-anthra[1,2-d]imidazole-6,11-dione,
2-(2-(4-phenylpiperazin-1-yl)ethyl)-1H-anthra[1,2-d]imidazole-6,11-dione,
2-(2-(4-(pyridin-2-yl)piperazin-1-yl)ethyl)-1H-anthra[1,2-d]imidazole-6,11-dione,
2-(2-(4-(pyrimidin-2-yl)piperazin-1-yl)ethyl)-1H-anthra[1,2-d]imidazole-6,11-dione, or
2-(2-(4-benzylpiperazin-1-yl)ethyl)-1H-anthra[1,2-d]imidazole-6,11-dione.

3. A method as recited in claim 2, wherein said amine in said step 2 is one selected from the group consisting of:
  (1) dimethylamine, (2) N-ethylmethylamine, (3) diethylamine, (4) N-methylpropylamine, (5) N-ethylisopropylamino, (6) 2-(2-methylaminoethyl)pyridine, (7) 2-methylaminomethyl-1,3dioxolane, (8) 3-methoxy-N-methybenzylamine, (9) di-(2-picolyl)amine, (10) 9-(methylaminomethyl)anthracene, (11) 2-(trifluoromethyl)benzylamine, (12) 3-(trifluoromethyl)benzylamine, (13) 4-(trifluoromethyl)benzylamine, (14) piperonylamine, (15) piperidine , (16) 4-methylpiperidine, (17) hexamethyleneimine, (18) 1,4-dioxa-8-azaspiro[4.5]decane, (19) 4,4'-trimethylenebis-(1-methylpiperidine), (21) thiomorpholine, (22) thiazolidine, (23) N-methylpiperazine, (24) 1-ethylpiperazine, (25) 1-allylpiperazine, (26) N-phenylpiperazine, (27) 1-(2-pyridyl)piperazine, (28) 1-(2-pyrimidyl)piperazine, (29) 1-(2-fluorophenyl)piperazine, (30) 1-(2-cyanophenyl)piperazine, (31) 1-(3-methoxyphenyl)piperazine, and (32) 1-benzylpiperazine;
and wherein said amine in said step 5 is one selected from the group consisting of:
  (1) N-methylpiperazine, (2) N-phenylpiperazine, (3) 1-(2-pyridyl)piperazine, (4) 1-(2-pyrimidyl)piperazine, and (5) 1-benzylpiperazine.

4. A pharmaceutical composition for treating cancer, comprising a therapeutically effective amount of at least one compound as recited in claim 1 and a pharmaceutically acceptable excipient.

5. A pharmaceutical composition as recited in claim 4, wherein said pharmaceutical composition comprises at least one compound selected from the group consisting of
2-((dimethylamino)methyl)-1H-anthra[1,2-d]imidazole-6,11-dione,
2-((ethylmethylamino)methyl)-1H-anthra[1,2-d]imidazole-6,11-dione,
2-((diethylamino)methyl)-1H-anthra[1,2-d]imidazole-6,11-dione,
2-((methylpropylamino)methyl)-1H-anthra[1,2-d]imidazole-6,11-dione,
2-((N-methyl-2-(pyridin-2-yl)ethanamino)methyl)-1H-anthra[1,2-d]imidazole-6,11-dione,
2-(((anthracen-10-yl)-N-methylmethanamino)methyl)-1H-anthra[1,2-d]imidazole-6,11-dione,
2-((3-(trifluoromethyl)benzylamino)methyl)-1H-anthra[1,2-d]imidazole-6,11-dione,
2-((piperidin-1-yl)methyl)-1H-anthra[1,2-d]imidazole-6,11-dione,
2-((4-methylpiperidin-1-yl)methyl)-1H-anthra[1,2-d]imidazole-6,11-dione,
2-((4-(3-methoxyphenyl)piperazin-1-yl)methyl)-1H-anthra[1,2-d]imidazole-6,11-dione,
2-((4-benzylpiperazin-1-yl)methyl)-1H-anthra[1,2-d]imidazole-6,11-dione,
2-(2-chloroethyl)-1H-anthra[1,2-d]imidazole-6,11-dione,
2-(2-(4-methylpiperazin-1-yl)ethyl)-1H-anthra[1,2-d]imidazole-6,11-dione,
2-(2-(4-phenylpiperazin-1-yl)ethyl)-1H-anthra[1,2-d]imidazole-6,11-dione,
2-(2-(4-(pyridin-2-yl)piperazin-1-yl)ethyl)-1H-anthra[1,2-d]imidazole-6,11-dione,
2-(2-(4-(pyrimidin-2-yl)piperazin-1-yl)ethyl)-1H-anthra[1,2-d]imidazole-6,11-dione, and
2-(2-(4-benzylpiperazin-1-yl)ethyl)-1H-anthra[1,2-d]imidazole-6,11-dione.

6. A pharmaceutical composition as recited in claim 4, wherein said pharmaceutical composition comprises at least one compound selected from the group consisting of 2-((diethylamino)methyl)-1H-anthra[1,2-d]imidazole-6,11-dione and 2-((4-methylpiperazin-1-yl)methyl)-1H-anthra[1,2-d]imidazole-6,11-dione.

7. A pharmaceutical composition as recited in claim 6, wherein said said amount of said compound is effective to inhibit the growth of leukemia cell.

8. A pharmaceutical composition as recited in claim 4, wherein said pharmaceutical composition comprises 2-((4-methylpiperazin-1-yl)methyl)-1H-anthra[1,2-d]imidazole-6,11-dione, said pharmaceutical composition possesses drug-resistance against adriamycin (ADR).

9. A compound as recited in claim 1, selected from the group consisting of:

2-((diethylamino)methyl)-1H-anthra[1,2-d]imidazole-6,11-dione, 2-((N-methyl-2-(pyridin-2-yl)ethanamino)methyl)-1H-anthra[1,2-d]imidazole-6,11-dione, 2-((piperidin-1-yl)methyl)-1H-anthra[1,2-d]imidazole-6,11-dione, 2-((4-methylpiperazin-1-yl)methyl)-1H-anthra[1,2-d]imidazole-6,11-dione, 2-((4-phenylpiperazin-1-yl)methyl)-1H-anthra[1,2-d]imidazole-6,11-dione, and 2-((4-(pyridin-2-yl)piperazin-1-yl)methyl)-1H-anthra[1,2-d]imidazole-6,11-dione.

* * * * *